(12) United States Patent
Trost et al.

(10) Patent No.: US 8,032,244 B2
(45) Date of Patent: Oct. 4, 2011

(54) METHOD AND SYSTEM FOR CONCRETE QUALITY CONTROL BASED ON THE CONCRETE'S MATURITY

(75) Inventors: Steven M. Trost, Stillwater, OK (US); Michael Fox, Glencoe, OK (US)

(73) Assignee: Engius, Inc., Stillwater, OK (US)

( * ) Notice: Subject to any disclaimer, the term of this patent is extended or adjusted under 35 U.S.C. 154(b) by 0 days.

(21) Appl. No.: 12/109,165

(22) Filed: Apr. 24, 2008

(65) Prior Publication Data

US 2008/0221815 A1 Sep. 11, 2008

Related U.S. Application Data

(63) Continuation of application No. 11/714,628, filed on Mar. 6, 2007, now Pat. No. 7,398,131, which is a continuation of application No. 11/227,708, filed on Sep. 15, 2005, now abandoned, which is a continuation of application No. 10/631,532, filed on Jul. 31, 2003, now abandoned.

(60) Provisional application No. 60/400,284, filed on Jul. 31, 2002, provisional application No. 60/439,904, filed on Jan. 13, 2003, provisional application No. 60/438,860, filed on Jan. 8, 2003.

(51) Int. Cl.
 *G06F 19/00* (2011.01)
(52) U.S. Cl. ........ 700/109; 700/108; 700/110; 204/426; 73/19.08; 73/54.03; 73/803
(58) Field of Classification Search .......... 700/108–110; 204/426; 73/19.08, 54.03, 803
See application file for complete search history.

(56) References Cited

U.S. PATENT DOCUMENTS

| | | | |
|---|---|---|---|
| 4,186,592 A | | 2/1980 | Eirich et al. |
| 4,480,929 A | | 11/1984 | Hanson |
| 4,566,806 A | | 1/1986 | DeBondt |
| 4,615,215 A | | 10/1986 | Sugimoto et al. |
| 4,943,930 A | * | 7/1990 | Radjy .............................. 702/33 |
| 5,041,987 A | | 8/1991 | Kuwahara et al. |
| 5,262,967 A | | 11/1993 | Jaber et al. |
| 5,396,790 A | | 3/1995 | Koelliker et al. |
| 5,541,855 A | | 7/1996 | Enzler et al. |

(Continued)

OTHER PUBLICATIONS

"Investigation into Improved Pavement Curing Materials and Techniques: Part I (Phases I and II)", Iowa DOT Project TR-451, Apr. 2002.*

(Continued)

*Primary Examiner* — Michael D Masinick
(74) *Attorney, Agent, or Firm* — McAfee & Taft

(57) ABSTRACT

A method and system for controlling and monitoring the quality of concrete based on the concrete's maturity (which is a function of its time-temperature profile, or temperature history). Five different applications or embodiments of the present invention are discussed, namely, Enhanced Maturity, Moisture-Loss Maturity, Improved Maturity, SPC Maturity, Loggers, Readers, and Software. Enhanced Maturity involves a maturity calibration method to account for the water-to-cementitious-materials ratio, air content, and gross unit weight of the concrete. Moisture-Loss Maturity is a method for determining the appropriate time to terminate moisture-loss protection of concrete and concrete structures. Improved Maturity is a method and system for determining the strength of curing concrete using improved maturity calculations. SPC Maturity is a method that beneficially couples maturity measurements and calculations with Statistical Process Control (SPC) methods to enable rapid recognition of changes to the concrete mix and/or incompatibilities between the various components of the concrete mix. Loggers, Readers, and Software represent the preferred embodiment for automating and simplifying the implementations of Enhanced Maturity, Moisture-Loss Maturity, Improved Maturity, and SPC Maturity.

5 Claims, 20 Drawing Sheets

U.S. PATENT DOCUMENTS

| | | | |
|---|---|---|---|
| 5,939,889 | A | 8/1999 | Zoughi et al. |
| 6,690,182 | B2 | 2/2004 | Kelly et al. |
| 6,865,515 | B2 * | 3/2005 | Fox et al. .................... 702/187 |
| 6,913,384 | B2 | 7/2005 | Park et al. |
| 7,034,660 | B2 * | 4/2006 | Watters et al. ............. 340/10.41 |
| 7,038,470 | B1 * | 5/2006 | Johnson ........................ 324/664 |
| 7,398,131 | B2 * | 7/2008 | Trost et al. ................... 700/109 |
| 7,551,058 | B1 * | 6/2009 | Johnson et al. ............ 340/10.41 |
| 2002/0154029 | A1 * | 10/2002 | Watters et al. ........... 340/870.07 |
| 2003/0235306 | A1 * | 12/2003 | Fox et al. ...................... 380/255 |
| 2004/0083057 | A1 * | 4/2004 | Trost et al. ........................ 702/6 |
| 2007/0046479 | A1 * | 3/2007 | Hines ............................ 340/584 |

OTHER PUBLICATIONS

"Properties of early age concrete—Experiments and Modelling", A.-W. Gutsch, Institute for Building Materials, Structural Concrete and Fire Protection, TU Braunschweig, Germany, Mar. 12, 2001.*

"Nonresident Training Course: Builder 3&2, vol. 1", NAVEDTRA 14043, Mar. 1993, United States Navy.*

MoDOT Section 507, "Strength of Concrete using the Maturity Method", date unkown.*

"Concrete Property Test", National Concrete Pavement Technology Center, Apr. 2008.*

"The Maturity Method: From Theory to Application", Carino & Lew, Building and Fire Research Laboratory, NIST, 2001 Structures Congress & Exposition, May 21-23, 2001.*

"Concrete Technology Today: Portland Cement, Concrete, and Heat of Hydration", Portland Cement Association, vol. 18/No. 2, Jul. 1997.*

American Concrete Institute Committee 308, Standard Specification for Curing Concrete (ACI 308.1-98), Apr. 1, 1998, Published by American Concrete Institute.

* cited by examiner

METHOD AND SYSTEM FOR CONCRETE QUALITY CONTROL BASED ON THE CONCRETE'S MATURITY

CROSS-REFERENCE TO RELATED APPLICATIONS

The present application is a continuation of U.S. Ser. No. 11/714,628, filed on Mar. 6, 2007 now U.S. Pat. No. 7,398, 131, which claims priority to the following utility patent application filed Sep. 15, 2005, now abandoned and identified by U.S. Ser. No. 11/227,708 and utility patent application: METHOD AND SYSTEM FOR CONCRETE QUALITY CONTROL BASED ON THE CONCRETE'S MATURITY, filed Jul. 31, 2003, now abandoned and identified by U.S. Ser. No. 10/631,532; and provisional patent applications: METHOD FOR DEVELOPING PREDICTION MODELS FOR CONCRETE STRENGTH BASED ON THE CONCRETE'S MATURITY, filed on Jul. 31, 2002 and identified by U.S. Ser. No. 60/400,284; TERMINATION OF MOISTURE-LOSS PROTECTION OF CONCRETE BASED ON MATURITY METHODS, filed on Jan. 13, 2003 and identified by U.S. Ser. No. 60/439,904; and METHOD AND SYSTEM FOR DETERMINING CONCRETE STRENGTH USING IMPROVED MATURITY CALCULATIONS, filed on Jan. 8, 2003 and identified by U.S. Ser. No. 60/438,860. The entire content of each of the above-referenced patent applications is hereby incorporated herein by reference. The present application also specifically refers to Disclosure Document Number 498,054, submitted by Steven M. Trost of Stillwater, Okla. on Jul. 31, 2001 and received by the United States Patent and Trademark Office on Aug. 3, 2001. The Disclosure Document was entitled "Method for Quality Control of Concrete using Early-Strength Predictions in Conjunction with Statistical Process Control Charting."

STATEMENT REGARDING FEDERALLY SPONSORED RESEARCH AND DEVELOPMENT

Not Applicable.

BACKGROUND OF THE INVENTION

Conventional methods for determining the strength of concrete placed into a structure require casting, curing and breaking test specimens. The specimens, typically cured at a constant temperature in a 100% humidity environment, are assumed to be representative of the concrete in the structure itself. However, the curing conditions for the concrete within the structure are rarely, if ever, the same as the conditions seen by the test specimens. Furthermore, conventional methods for estimating the compressive and/or flexural strengths of concrete are expensive and lack the desired levels of precision often required for quality control and acceptance applications.

The maturity method for estimating concrete strength produces an estimate of strength based on the actual temperature history experienced by the in-place concrete. As such, the maturity method attempts to reduce the incongruity resulting from differing hydration rates experienced by lab-cured specimens compared to the in-place concrete. Even so, the maturity method requires development of a strength-maturity relationship curve (also called a calibration curve) that is specific to the mixture components contained in the calibration test batch. Any significant change in the relative amounts of the individual mixture components can render the calibration curve biased or unreliable.

The use of maturity methods as a means for concrete quality control and acceptance will be hindered until methods are demonstrated to adequately and easily account for the variations in mixture components that commonly occur between various concrete batches under normal field conditions. Air and water content represent two concrete mixture components that [1] greatly influence the final strength of the concrete and [2] can vary considerably from batch-to-batch, day-to-day and week-to-week even for a given concrete mix design.

Brief History of the Maturity Method

The maturity method for measuring concrete strength has been in use for over fifty years and became an ASTM (American Society for Testing and Materials) standard in 1987 (ASTM C 1074). The heart of the method lies in the scientific relationship between chemical reaction rates and the energy (i.e. temperature) of the molecules involved in the reaction. Almost without exception, chemical reactions proceed more quickly at elevated temperatures. The application of this law to the complex chemical reactions in concrete has been demonstrated time and again both in the laboratory and the field over the past fifty years. A tragic display of this phenomenon occurred in 1973 in Fairfax County, Va. when a multi-story building collapsed during construction, killing fourteen and injuring 34. The National Bureau of Standards (NBS) investigated the accident at the request of the Occupational Safety and Health Administration (OSHA). NBS investigators identified a four-day-old floor slab (which had been subjected to an average ambient temperature of only 7° C.) as the most likely cause of the accident (Carino and Lew 2001). This disastrous result of the temperature-dependence of concrete strength gain and a similar accident in 1978 sparked serious examination of available methods for estimating the in-place strength of concrete during construction. As a result, the NBS identified the maturity method as a viable means for estimating the strength of concrete subjected to different curing temperatures (Carino and Lew 2001). This, in turn, led to the establishment of one of the world's first standard (ASTM C 1074) for estimating concrete strength via the maturity method. As a part of the Strategic Highway Research Program (SHRP) in the mid-1990s, the Federal Highway Administration (FHWA) recommended maturity as an available technology for estimating in-place concrete strength development in highway structures (Carino and Lew 2001). The FHWA now routinely demonstrates the application of the concrete maturity method to interested federal, state and local transportation personnel via their Mobile Concrete Laboratory.

Benefits of Using Maturity Methods

The maturity method for measuring concrete strength delivers the following benefits:

a) Provides a better representation of in-place concrete strength gain than laboratory or field-cured specimens.

b) Enables any-time in-place strength measurements.

c) Provides better timing for strength-dependent construction activities.

d) Saves time and money compared to conventional strength-testing procedures.

e) Enables in-place measurements at "lowest strength" locations.

f) Enables in-place strength measurements at "critical stress" locations.

Concerning the representation of in-place concrete strengths, the Federal Highway Administration (FHWA 1988) determined that even field-cured specimens do not accurately reflect the true rate of hydration experienced by the concrete in a structure. Hossain and Wojakowski (1994) also observed significant differences in hydration rates between in-place concrete and field-cured beam specimens. These inaccuracies are then amplified when laboratory-cured rather than field-cured specimens are used to estimate in-place concrete strength. In fact, even core specimens drilled directly from the structure do not accurately represent the strength of the concrete in the structure. The American Concrete Institute (ACI) acknowledges this fact in their well-known building code for concrete construction (ACI 318). ACI 318 recommends strength acceptance of concrete if the average of three drilled cores meets or exceeds 85% of the specified strength as long as no single core falls below 75% of the required strength. In summary, when adequate process control measures are in place for the concrete batching operations, maturity represents one of the best available method for measuring the in-place strength gain for a concrete structure.

In addition, the maturity method enables the Contractor and/or Engineer to measure strength within a structure at any time and as many times as necessary until the desired strength is achieved. Conventional strength-estimation methods require the destructive testing of cylinder, beam or core specimens and, as such, are subject to a serious "Catch-22." If all the specimens are tested too early (i.e. the measured strength is still too low), no specimens will be available to measure strength at a later time. If the specimens are tested too late (i.e. the measured strength is much higher than required), valuable construction time has been lost. This problem can be alleviated by producing extra test specimens (e.g. two or three times as many) to make sure enough specimens are available at just the right time. Casting, curing and testing extra specimens is obviously expensive and time consuming. By far, the better solution involves the use of maturity to provide anytime measurements for in-place concrete strengths.

Because the maturity method provides a better representation of the in-place strength gain for a concrete structure and can be measured at any time, better timing can be applied to construction activities that are dependent upon the concrete having attained certain minimum strength values (e.g. post-tensioning, cutting pre-stress tendons, removing formwork/falsework, backfilling, etc.). This improved timing results in maximum time savings without sacrificing safety or quality.

Given the high cost of user delays and contract overhead, the financial savings resulting from the improved timing of construction activities is sizeable. Furthermore, additional financial savings result from the reduced number of test specimens required when maturity methods are appropriately utilized. Concerning the potential savings from the use of maturity methods, the Federal Highway Administration (Crawford 1997) states, "The maturity method is a useful, easily implemented, accurate means of estimating in-place concrete strength . . . . In a time when public agencies and contractors are concerned with escalating costs and shrinking budgets, this method provides a viable means of reducing costs through testing and scheduling. Also, quality assurance costs can be reduced because the number . . . of test cylinders is reduced by using the maturity concept."

Given the fact that concrete subjected to higher temperatures will gain strength faster than concrete cured at lower temperatures, the concrete within a structure will gain strength at different rates in different locations depending upon the different temperature conditions within the structure. For instance, thinner sections will tend to generate and retain less internal heat than will adjacent sections containing more mass and/or less surface area. Similarly, portions of a structure (particularly pavement structures) can gain strength at different rates due to the effects of shading and/or direct sunlight. The maturity method for measuring in-place concrete strength enables the interested parties to take measurements at locations where the strength gain is likely to be slowest, providing additional assurance that subsequent work does not begin until adequate strength has been gained within the entire structure.

In addition, this "pinpoint" capability of measuring strength via maturity allows the engineer to specifically target strength measurements in those locations where critical stresses are expected for the anticipated loading conditions during subsequent construction activities.

Hydration of the cementitious reaction products in concrete requires water as the complementary reactant. Whereas water represents one of the major constituents of fresh concrete, the initial water within the concrete mass ignites the initial hydration reactions and allows the hydration reactions to continue until the water and/or the cementitious reaction products are completely used up. As such, the ongoing cementitious hydration of concrete tends to desiccate the concrete over time. Further loss of internal moisture in the concrete due to evaporation from the surface tends to result in drying-shrinkage cracks in the concrete mass. In addition, the concrete may experience drying-shrinkage cracking due to its own self-desiccating properties (even with minimal evaporative moisture losses).

As a result, extreme care is required to protect the concrete (after its initial placement and subsequent finishing operations) from moisture loss and/or to add moisture to the concrete (to counteract the self-desiccation tendencies of the concrete). Certain types of moisture protection, such as liquid membrane curing agents, are degraded by ultraviolet radiation (i.e. sunlight) and/or foot- or vehicular-traffic. Other types of moisture protection, such as wet burlap or fog curing, require equipment and/or materials to remain on and/or adjacent to the concrete mass until such moisture protection is no longer necessary. Determining how long to maintain protection from moisture loss and/or providing additional moisture to the concrete mass is currently based on non-quantitative and inexact methods, such as specified minimum durations (such as the minimum seven-day water-cure required for bridge decks by the State of Oklahoma's Department of Transportation). These specified minimum durations are typically based on past experience with little or no relevance to the actual project conditions and/or concrete mix design being utilized.

Current "time-based" methods (such as the minimum seven-day water-cure required for bridge decks by the State of Oklahoma's Department of Transportation) for terminating moisture-loss protection of concrete are subject to numerous limitations. Two primary limitations are as follows:

1. Whereas the cementitious materials in concrete hydrate faster at higher temperatures, the use of a time-based method for determining protection from moisture loss experiences the same limitations as time-based strength-determinations. The disasters mentioned above highlight the inadequacies of such determinations. In essence, concrete subjected to higher temperatures will tend to require protection from moisture loss for a shorter duration than if it were subjected to lower temperatures. As such, the time should be "adjusted" based on the temperature-time history of the concrete. Properly applied, maturity methods can be used to meet this need.

2. Whereas the amount of cementitious material, types of cementitious materials, ratio of water to cementitious materials, etc. within a concrete mixture can have profound impacts on the hydration rate and self-desiccation properties of the concrete, a time-based approach simply cannot efficiently accommodate all the possibilities. A mix-specific calibration using maturity or enhanced maturity methods can be used to overcome this limitation.

As such, an approach is desperately needed that can "adjust" the time requirement based on the properties of the concrete mix itself as well as the environmental conditions to which the concrete mass is ultimately subjected. Maturity and enhanced maturity methods (as discussed herein) can be employed to overcome these limitations.

The American Society for Testing and Materials (ASTM) developed a standard calibration procedure (ASTM C 1074) for predicting the compressive strength of concrete using strength-maturity relationship information and subsequent maturity calculations based on periodic temperature measurements. Each calibration curve is specific to a given mix design (i.e. the specific proportions and sources of the raw materials such as portland cement, fly ash, coarse aggregate, fine aggregate, etc.). As a part of the ASTM C 1074 standard practice, ASTM recommends two different methods for determining strength from maturity-Nurse-Saul and Arrhenius. The Nurse-Saul method relies upon a "datum temperature" as the basis for the maturity calculation, whereas the Arrhenius method relies upon an "apparent activation energy" value. ASTM C 1074 also provides recommended procedures for experimentally determining the datum temperature and/or apparent activation energy for the specific mix design for which strength-by-maturity determinations are desired.

The accuracy, repeatability and reproducibility of the ASTM C 1074 methods for determining datum temperature and apparent activation energy are less than optimum. In addition, whereas the cementitious hydration reactions occurring within a concrete mass result from many different cementitious reaction products, each of which has its own unique activation energy, the use of a single apparent activation energy and/or a single datum temperature to characterize the mix for all curing conditions may, at times, provide very unconservative prediction results. This is particularly so with the Arrhenius method, which is based on an exponential model for the maturity calculation as follows:

$$M = \sum_0^t \left[ e^{-\frac{E_a}{R}\left(\frac{1}{T+273} - \frac{1}{T_{ref}+273}\right)} \cdot \Delta t \right]$$

where
M=concrete maturity expressed as equivalent age (in hours or days)
e=natural logarithm constant (=2.7183)
$E_a$=apparent activation energy (in J/mole)
R=universal gas constant (=8.3144 J/(mole×K))
T=average temperature (in ° C.) during time interval $\Delta$t
$T_{ref}$=reference temperature (in ° C.)
$\Delta$t=length of time interval (in hours or days)
(NOTE: Sometimes the ratio $E_a$/R is replaced by the term Q, which is simply the apparent activation energy divided by the gas constant, in Kelvin units.)

Because the maturity calculation for the Arrhenius method relies upon an exponential model and because the apparent activation energy of the concrete mix is a part of the exponent, small variations in apparent activation energy can effectuate large changes in the calculated maturity value. This, in turn, can lead to substantial variations in the predicted strength values. At times, these variations may err on the conservative side. However, at other times these variations may be unconservative and, as such, may lead to unsafe conditions (e.g. removal of formwork or falsework before the concrete has achieved the necessary strength to support its own weight). Unfortunately, the apparent activation energy for the mix cannot be precisely determined ahead of time and the apparent activation energy can vary throughout the curing process (as different cementitious reaction products are used up and others are created) and/or throughout the life of a project (as cementitious materials with differing chemical compositions and/or other quality characteristics may be used throughout the life of a construction project, even when the materials are received from the same supplier and same manufacturing facility). This uncertainty about the "true" apparent activation energy of the mix creates a situation wherein one cannot know whether the corresponding maturity calculations are conservative or unconservative and, subsequently, whether the strength predictions based on those maturity calculations are conservative or unconservative.

In a similar, but less severe, fashion, the Nurse-Saul method can, at times, be unconservative. The impact is usually less severe due to the fact that the Nurse-Saul method assumes a linear rather than exponential relationship between temperature and cementitious reaction rates. The Nurse-Saul equation is as follows:

$$M = \sum_0^t [(T - T_o) \cdot \Delta t]$$

where
M=concrete maturity expressed as temperature-time factor (TTF) (in ° C.-Hours)
T=average temperature (in ° C.) during time interval $\Delta$t.
$T_o$=datum temperature (in ° C.)
$\Delta$t=length of time interval (in hours)

The unconservative potential of conventional maturity calculations both for Arrhenius and Nurse-Saul methods is shown in Table 1 (where unconservative is defined as having an equivalent age factor, or EAF, higher than the "true" EAF).

Equivalent age represents the "age" of a mass of concrete expressed in terms of the actual age (in actual hours or days) of a separate, but similar, mass of concrete cured at a reference temperature. Two concrete masses having the same equivalent age are said to be equivalent in terms of the degree of cementitious hydration that has occurred within each mass. This expression of concrete maturity is most commonly associated with the Arrhenius method for determining concrete strength from maturity. However, the Nurse-Saul equation can be rearranged so as to equate the Nurse-Saul maturity value to an equivalent age or equivalent age factor (Carino and Lew 2001). Equivalent Age Factor, or EAF, refers to the factor, or multiplication value, necessary to convert the actual age of a mass of concrete, cured at temperatures other than the reference temperature, to its equivalent age. If the mass of concrete has been constantly cured at the reference temperature, its equivalent age factor will be one and its equivalent age will equal its actual age. If, on the other hand, the concrete has been cured at temperatures higher than the reference temperature, the equivalent age factor will be greater than one and its equivalent age will be greater than its actual age. For instance, if EAF=2.0, the concrete is presumed to be gaining strength twice as fast as concrete cured at the reference temperature. As such, if a concrete mass is cured at a constant temperature corresponding to an EAF=2.0, it is presumed to have reached two days' strength in one day, where "two days' strength" is the strength achieved in two days by similar concrete cured at the reference temperature.

As can be seen in Table 6, if the "true" apparent activation energy of the mix is relatively high (e.g. Q=6500 K, corresponding to $E_a$=54 kJ/mol), Arrhenius maturity calculations performed using lower activation energies are unconservative at lower temperatures (as shown graphically in FIG. 11), as is the Nurse-Saul method in this instance (where the reference temperature $T_{ref}$ is 50° C. and a datum temperature $T_o$ of −10° C. is utilized) (as shown graphically in FIG. 12). Table 6 further demonstrates that, if the "true" apparent activation energy is relatively low (e.g. Q=3500 K, corresponding to $E_a$=29 kJ/mol), then Arrhenius maturity calculations performed using higher activation energies are unconservative at higher temperatures (as shown graphically in FIG. 13). Whereas the "true" apparent activation energy for a given mix is difficult to measure and can possibly change over time, it can be potentially dangerous to rely upon conventional maturity calculations (whether based on Arrhenius or Nurse-Saul) across the range of temperatures and conditions to which a mass of curing concrete might be exposed. Improved Maturity, as discussed herein, overcomes this limitation.

DETAILED DESCRIPTION OF THE INVENTION

Figure 1:
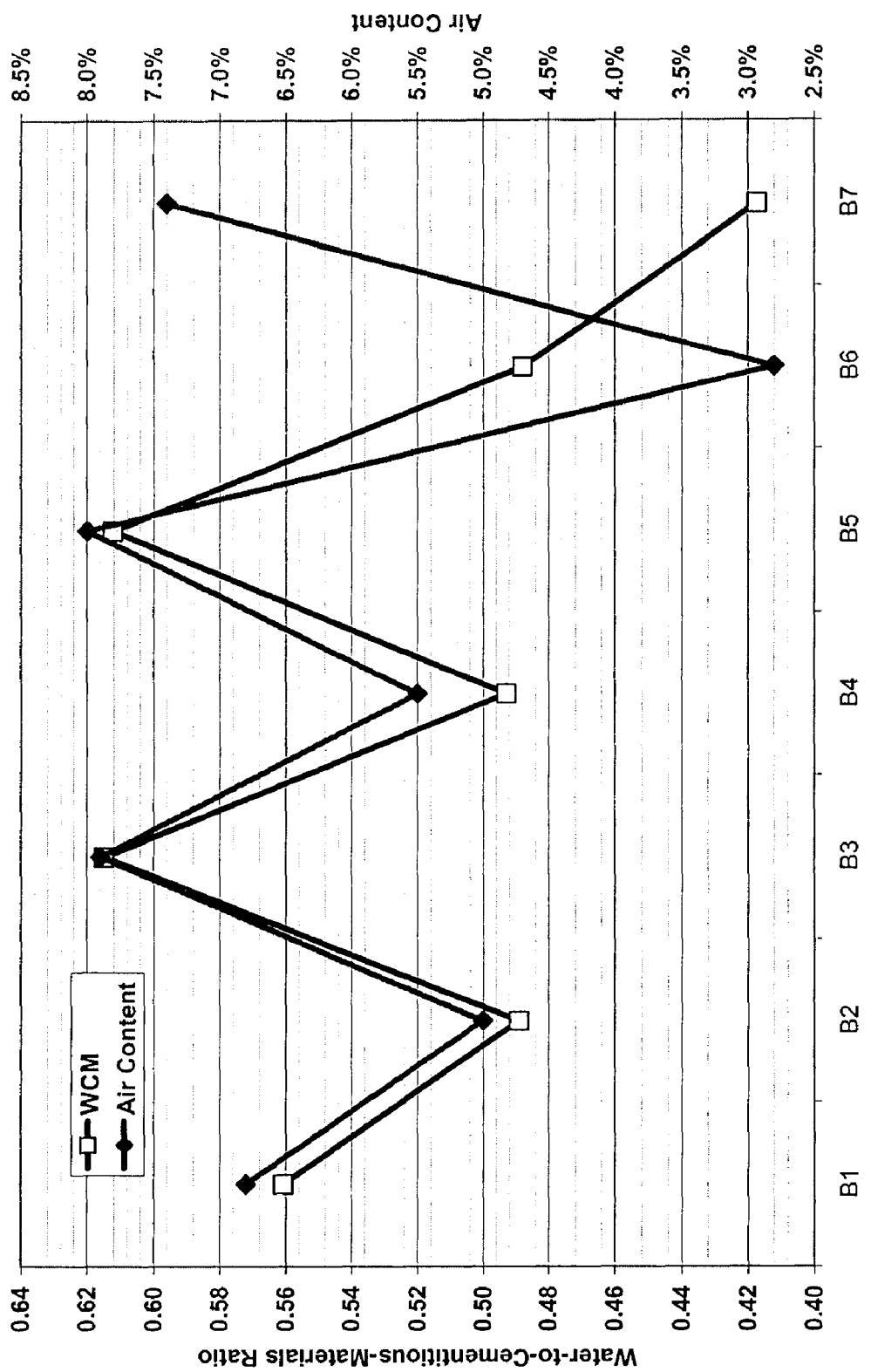
FIG. 1—Shows the air contents and water-to-cementitious-materials ratios for the seven Enhanced Maturity calibration batches performed in accordance with the present invention on a "Mix B" batch of concrete.

Despite their tremendous benefits to the construction industry, conventional maturity methods as currently implemented face a significant limitation in that they rely upon a mix-specific (or, it can be argued, a batch-specific) calibration curve to establish a relationship between the time-temperature history of the concrete (i.e. its "maturity") and the compressive and/or flexural strength of the concrete. The American Society for Testing and Materials (ASTM) developed a standard calibration procedure (ASTM C 1074) for predicting the compressive strength of concrete using cylinder specimens and maturity readings. Each calibration curve is specific to a given mix design (i.e. the specific proportions and sources of the raw materials such as portland cement, fly ash, coarse aggregate, fine aggregate, etc.). Each calibration curve is technically only applicable when certain other batch-specific characteristics of the mix are held constant, such as water-to-cementitious-materials ratio and air content. As such, the calibration curves developed by conventional methods lack precision and accuracy as an estimator of concrete strength whenever the characteristics of the concrete mentioned above are not strictly controlled. However, these characteristics are difficult to measure accurately and precisely and even more difficult to control accurately and precisely.

The present invention (referred to herein as "Enhanced Maturity") involves a calibration method to account for the characteristics mentioned above, namely water-to-cementitious-materials ratio (wcm), air content and gross unit weight. The calibration method will ensure a more precise and accurate estimate of concrete strength than can be currently achieved using maturity methods alone. In addition, the precision and accuracy of the new calibration method may very well rival or best the current levels available via destructive testing.

Enhanced Maturity represents a novel method and system for developing prediction models for concrete strength based on the concrete's maturity (which is a function of its time-temperature profile, or temperature history), air content and water-to-cementitious-materials ratio. The method employs a design of experiments (DOE) and response surface methodology (RSM) approach to quantitatively account for the effect on strength of each of the factors mentioned as well as any interaction effects between the factors. An extension of Enhanced Maturity involves the use of full- and/or fractional-factorial DOE and/or RSM experimentation to perform mix design optimizations including additional factors that influence concrete strength (such as cement content, fly ash replacement percentage, silica fume, accelerating admixtures, etc.) A further extension then involves the re-optimization of mix designs in real time (during actual concrete production) by conducting early-age strength tests and applying classical and Bayesian regression techniques that combine the new data with the original DOE and RSM mix design optimization data, thus developing new quantitative strength models. This same "re-optimization" technique can be applied to standard maturity data such that maturity curves can be revised and updated in real time as additional maturity vs. strength data become available.

Another aspect of the present invention (referred to herein as "Moisture-Loss Maturity" or "hydration maturity") represents a novel method and system that involves a calibration procedure to determine the relationship between concrete maturity and its overall degree of hydration. As such, a maturity index value (expressed as a temperature-time factor, equivalent age, or other appropriate measure of maturity) can be used to ultimately measure the degree of hydration of a concrete mass. This allows specifying agencies (such as State Highway Agencies, federal, state and local governments, or any other organization responsible for funding and/or designing facilities that incorporate concrete as a building material) to specify the degree of hydration required (for termination of moisture-loss protection activities) rather than simply specifying a time period. As such, Moisture-Loss Maturity utilizes the maturity method to determine the critical times for protecting a given concrete mass from moisture loss and/or for providing additional moisture to the concrete mass. Moisture-Loss Maturity incorporates a calibration procedure to relate degree of hydration to the maturity of the concrete (usually expressed as a temperature-time factor or equivalent age). Once the calibration has been performed for a given concrete mix design, degree of hydration can be accurately predicted by measuring the concrete's maturity. The predicted degree of hydration can then be used to determine if moisture-loss protection can be "safely" terminated.

Yet another aspect of the present invention (referred to herein as "Improved Maturity") represents a novel method and system to ensure conservatism when using maturity methods to determine the strength of concrete. The method can be implemented as a protocol for use with the Arrhenius maturity method and, similarly, as a protocol for use with the Nurse-Saul maturity method. The benefits of Improved Maturity are derived from the fact that a conservative maturity calculation is guaranteed, irrespective of the "true" apparent activation energy of the concrete's constituent cementitious and pozzolanic materials. Improved Maturity can be readily applied to the Arrhenius method for determining strength from maturity or to the Nurse-Saul method, or to some variant thereof, or to any similar methods. The application of Improved Maturity to the Arrhenius method results in an Improved Arrhenius method and, separately, the application of Improved Maturity to the Nurse-Saul method results in an Improved Nurse-Saul method. A protocol for applying the invention to the Arrhenius method generally involves determining the reference temperature for a given calibration batch, then performing subsequent Arrhenius maturity calculations using a "high" apparent activation energy value (e.g. 54 kJ/mole) at temperatures below the reference temperature and using a "low" apparent activation energy value (e.g. 29 kJ/mole) at temperatures above the reference temperature, creating a dichotomous exponential model relating the rate of cementitious hydration to variations in temperature for a given concrete mix design. This dichotomous model remains conservative for strength predictions irrespective of the "true" apparent activation energy of the concrete mix design and irrespective of the curing temperature of the concrete. A protocol for applying Improved Maturity to the Nurse-Saul method closely follows the Improved Arrhenius protocol. The resulting Improved Nurse-Saul model is a dichotomous straight-line (rather than exponential) model wherein each portion of the model is tangential or nearly tangential (at the reference temperature) to its respective portion of the dichotomous Arrhenius model. Various Improved Nurse-Saul protocols are also presented that simplify the end use of the Improved Nurse-Saul method.

A further aspect of the present invention (referred to herein as "SPC Maturity") represents a novel method and system that beneficially couples maturity measurements and calculations with Statistical Process Control (SPC) methods to enable rapid recognition of changes to the concrete mix and/or incompatibilities between the various components of the concrete mix.

Enhanced Maturity

Enhanced Maturity involves conducting a design of experiments (DOE) with three factors (maturity, water-to-cementitious-materials ratio and air content) to establish a single equation to predict concrete strength. The equation will be applicable to all batches of the given concrete mix design, not just those with a specific water-to-cementitious-materials ratio and air content. The equation will generally be based on a 3×2×2, 4×2×2 or 5×2×2 full-factorial experiment on maturity, water-to-cementitious-materials ratio (wcm) and air content and may take the following form:

$$\text{EstimatedStrength} = B_1 + B_2 * \text{Maturity} + B_3 * \text{WCM} + B_4 * \text{AirContent} + B_5 * \text{Maturity} * \text{WCM} + B_6 * \text{Maturity} * \text{AirContent} + B_7 * \text{WCM} * \text{AirContent} + B_8 * \text{Maturity}^2 + B_9 * \text{Maturity}^3$$

where $B_i$=calibration constants to be determined by the experimentation

In most circumstances, it is advisable to run one or more "center point" batches during the full-factorial DOE. A center point batches represents a middle level for all the factors at once. Furthermore, under certain conditions, it may be advisable to use a 3×3×3, 4×3×3 or 5×3×3 factorial experiment on maturity, water-to-cementitious-materials ratio and air content to enable estimation of the squared terms for wcm and/or air content. In that case, the prediction equation may take the following form:

$$\text{EstimatedStrength} = B_1 + B_2 * \text{Maturity} + B_3 * \text{WCM} + B_4 * \text{AirContent} + B_5 * \text{Maturity} * \text{WCM} + B_6 * \text{Maturity} * \text{AirContent} + B_7 * \text{WCM} * \text{AirContent} + B_8 * \text{Maturity}^2 + B_9 * \text{Maturity}^3 + B_{10} * \text{WCM}^2 + B_{11} * \text{AirContent}^2$$

where $B_i$=calibration constants to be determined by the experimentation

Variations in the above equations may be necessary to satisfy the assumptions required for statistical analysis and prediction-model development. As such, transformations of the variables via square root functions, logarithmic or power transformations, etc. may be necessary or beneficial. Furthermore, inclusion of other variables in the DOE, such as aggregate contents, coarse-to-fine aggregate ratios, cement type, etc., may be advisable to create a strength-from-maturity prediction model with broader applications and/or to optimize the mix design. In such circumstances it may also be advisable to employ fractional-factorial experimentation and/or central composite designs (CCD) or other response surface methodologies (RSM). Even with the full-factorial DOE experiment, analysis of the data is best done using response surface regression techniques rather than conventional DOE analysis procedures. This stems from the fact that DOE analysis assumes (and requires) that the "equivalent" levels for a given factor be the same with different treatment combinations. For instance, if the high and low levels for wcm are 0.32 and 0.42 and the high and low levels for air content are 1.0% and 9.0%, DOE analysis would assume (and require) that the air content level be the same in the high wcm/high air treatment combination as with the low wcm/high air combination (e.g. 9.0%). However, controlling air content to 0.1% (or even 0.5%) with experimental batches is difficult, if not impossible (at least from a practical standpoint). Response surface regression techniques do not require the same levels across different treatment combinations and, as such, make use of those subtle (or not-so-subtle) deviations in determining the appropriate calibration constants.

The water-to-cementitious-materials ratio (wcm) can be measured by a plurality of methods that are known in the art. Examples include the following:

Calculations based on batch weights of the raw materials. This method typically uses a moisture-correction factor to separate the weight of each aggregate source into two components—[1] the weight of aggregate at saturated-surface-dry (SSD) conditions and [2] the weight of the excess water contributed to the mix by the aggregate. The resulting wcm can then be calculated as the total weight of the water (batched water plus "excess" water from each aggregate source) divided by the total weight of the cementitious materials. Many conventional batch plants automatically perform these calculations and print the resulting wcm directly on the batch ticket.

Use of a rapid-drying technique to measure the free moisture in the fresh concrete, such as the AASHTO TP-23 Provisional Standard Test Method for Water Content of Freshly Mixed Concrete using Microwave Oven Drying, then dividing the total water mass by the total mass of cementitious materials.

Use of a nuclear-gauge instrument such as the Troxler 4430 Water Cement Gauge as manufactured by Troxler Electronic Laboratories, Inc of Research Triangle Park, N.C.

However, under certain conditions, the water-to-cementitious-materials ratio may be difficult to measure with the required levels of precision and accuracy. For example, Method #1 (calculation from batch weights) is unreliable whenever the true aggregate moisture is changing from batch to batch and/or is not known. Concerning Method #2 (microwave oven-drying), a study commissioned by the Wisconsin Department of Transportation (Dowell and Cramer 2002) stated the "accuracy of the method is borderline useful largely because of the small sample size." That same report commented on Method #3 (nuclear gauge) by stating "[g]iven the NRC [Nuclear Regulatory Commission] training and certification and labor-intensive calibration procedure, it does not appear that the method meets the needs of the concrete pavement industry." In those instances where conventional methods prove unreliable and/or impractical, gross unit weight can be substituted for water-to-cementitious-materials ratio in either of the above procedures (or used as a supplemental measure for wcm). As such, the resulting equations will include inputs related to GrossUnitWeight (i.e. as per ASTM C 138) rather than WCM. Alternatively, a novel method is herein disclosed wherein wcm can be "backcalculated" from the measures of air content and gross unit weight when combined with the specific gravities and batch weights for the remaining constituents in the concrete batch (e.g. cement, fly ash, coarse aggregate and fine aggregate). This "backcalculation" can be performed by simultaneously solving the following seven equations having seven unknowns:

$$V_{Coarse} + V_{Fine} + V_{Water} + V_{Air} + V_{Cement} + V_{FlyAsh} = V_{Concrete}$$

$$V_{Coarse} = \frac{\frac{W_{Coarse} + W_{CoarseWater}}{W_{Solids}} \cdot \left(\frac{V_{Concrete}}{\gamma_{Concrete}} - \frac{V_{Water}}{\gamma_{Water}}\right)}{\gamma_{Coarse}}$$

$$V_{Fine} = \frac{\frac{W_{Fine} + W_{FineWater}}{W_{Solids}} \cdot \left(\frac{V_{Concrete}}{\gamma_{Concrete}} - \frac{V_{Water}}{\gamma_{Water}}\right)}{\gamma_{Fine}}$$

$$V_{Cement} = \frac{\frac{W_{Cement}}{W_{Solids}} \cdot \left(\frac{V_{Concrete}}{\gamma_{Concrete}} - \frac{V_{Water}}{\gamma_{Water}}\right)}{\gamma_{Cement}}$$

$$V_{FlyAsh} = \frac{\frac{W_{FlyAsh}}{W_{Solids}} \cdot \left(\frac{V_{Concrete}}{\gamma_{Concrete}} - \frac{V_{Water}}{\gamma_{Water}}\right)}{\gamma_{FlyAsh}}$$

$$W_{Solids} = W_{Coarse} + W_{CoarseWater} + W_{Fine} + W_{FineWater} + W_{Cement} + W_{FlyAsh}$$

$$WCM = \frac{V_{Water}/\gamma_{Water}}{(V_{Cement}/\gamma_{Cement}) + (V_{FlyAsh}/\gamma_{FlyAsh})}$$

where, $V_{Coarse}$=Volume of the coarse aggregate (in the unit-weight bucket) at saturated surface dry (SSD) conditions (unknown), $V_{Fine}$=Volume of the fine aggregate (in the unit-weight bucket) at SSD conditions (unknown), $V_{Water}$=Volume of all the water in the concrete (in the unit-weight bucket) that is above and beyond the water in the aggregates (with the aggregates at SSD) (unknown), $V_{Air}$=Volume of total air in the concrete (in the unit-weight bucket) (known by separate measurement, such as via ASTM C 231 or ASTM C 173), $V_{Cement}$=Volume of cement in the concrete (in the unit-weight bucket) (unknown), $V_{FlyAsh}$=Volume of the fly ash in the concrete (in the unit-weight bucket) (unknown), $V_{Concrete}$=Volume of the concrete (in the unit-weight bucket) (known via use of a unit weight measurement bucket (or other container) of precisely known volume), $W_{coarse}+W_{CoarseWater}$=Weight of the coarse aggregate in the entire batch (includes the weight of excess water above and beyond SSD conditions) (known by measurements typically performed during batching operations—the data are usually printed on the batch ticket), $W_{Solids}$=Weight of the coarse aggregate, fine aggregate, cement, and fly ash in the entire batch, includes the excess water from the aggregates (unknown), $\gamma_{Concrete}$=Bulk specific gravity of the concrete (known from the weight of the unit-weight bucket full minus empty, then divided by the known internal volume of the bucket, i.e. as per ASTM C 138), $\gamma_{Water}$=Specific gravity of the water (a known physical constant), $\gamma_{Coarse}$=Bulk specific gravity of the coarse aggregate at SSD or, if possible, near the as-batched moisture content (known by previous measurement), $W_{Fine}+W_{FineWater}$=Weight of the fine aggregate in the entire batch (includes the weight of excess water above and beyond SSD conditions) (known by measurements typically performed during batching operations—the data are usually printed on the batch ticket), $\gamma_{Fine}$=Bulk specific gravity of the fine aggregate at SSD or, if possible, near the as-batched moisture content (known by previous measurement), $W_{Cement}$=Weight of the cement in the entire batch (known by measurements typically performed during batching operations—the data are usually printed on the batch ticket), $\gamma_{Cement}$=Specific gravity of the cement (known by previous measurement), $W_{FlyAsh}$=Weight of the fly ash in the entire batch (known by measurements typically performed during batching operations—the data are usually printed on the batch ticket), $\gamma_{FlyAsh}$=Specific gravity of the fly ash (known by previous measurement).

WCM=Water-to-cementitious-materials ratio (unknown).

The preferred embodiment of Enhanced Maturity uses the Nurse-Saul method for calculating concrete maturity (as described in ASTM C 1074). However, the Arrhenius calculation method (as described in ASTM C 1074) as well as other methods (see Carino and Lew 2001) can be used for calculating concrete maturity values as implemented with Enhanced Maturity. In addition, other methods for calculating concrete maturity may be developed and are easily incorporated into the present invention without departing from the spirit of the present invention.

Figure 2:
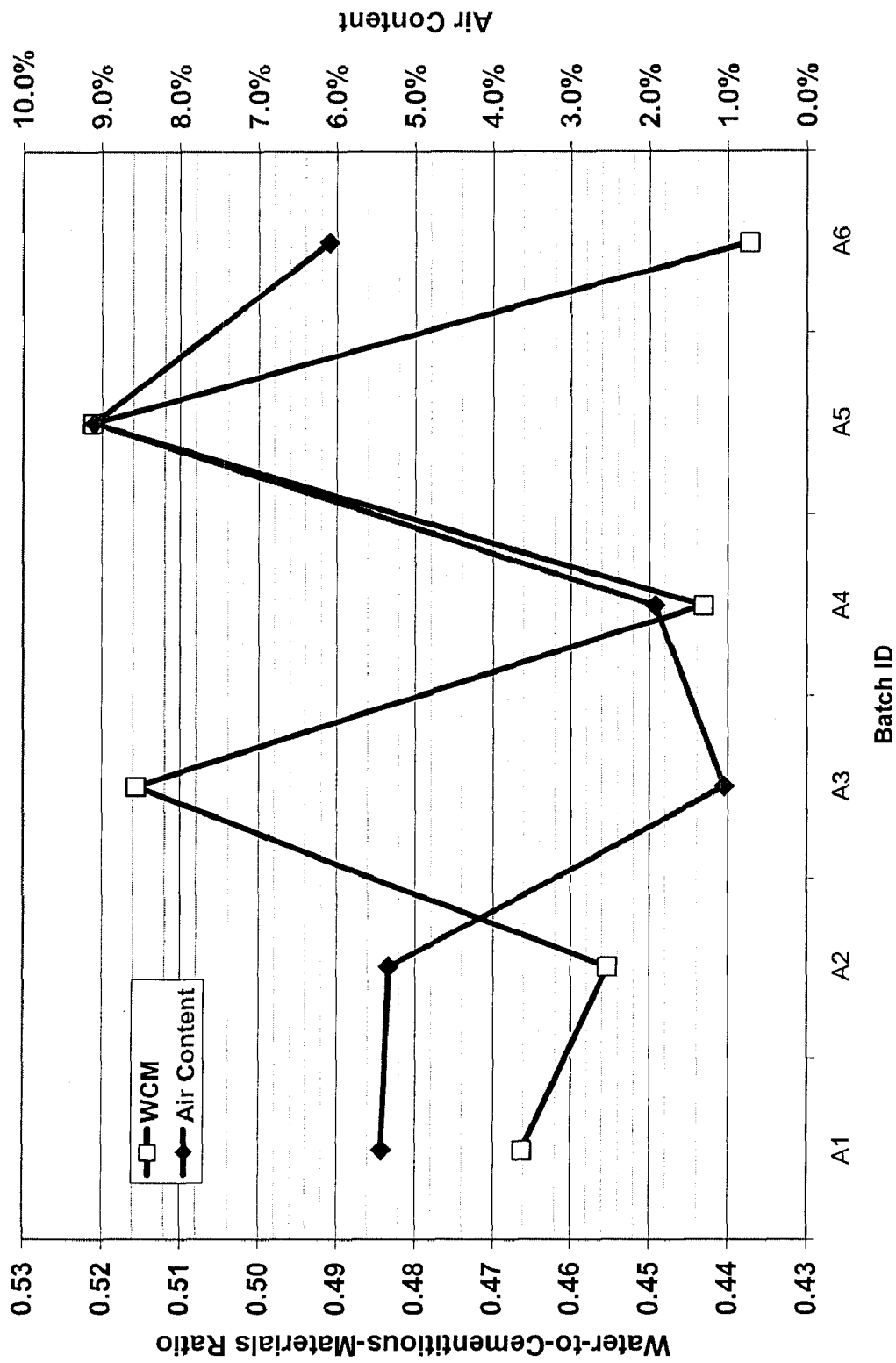
FIG. 2—Shows the air contents and water-to-cementitious-materials ratios for the six Enhanced Maturity calibration batches performed in accordance with the present invention on a "Mix A" batch of concrete.
Figure 3:
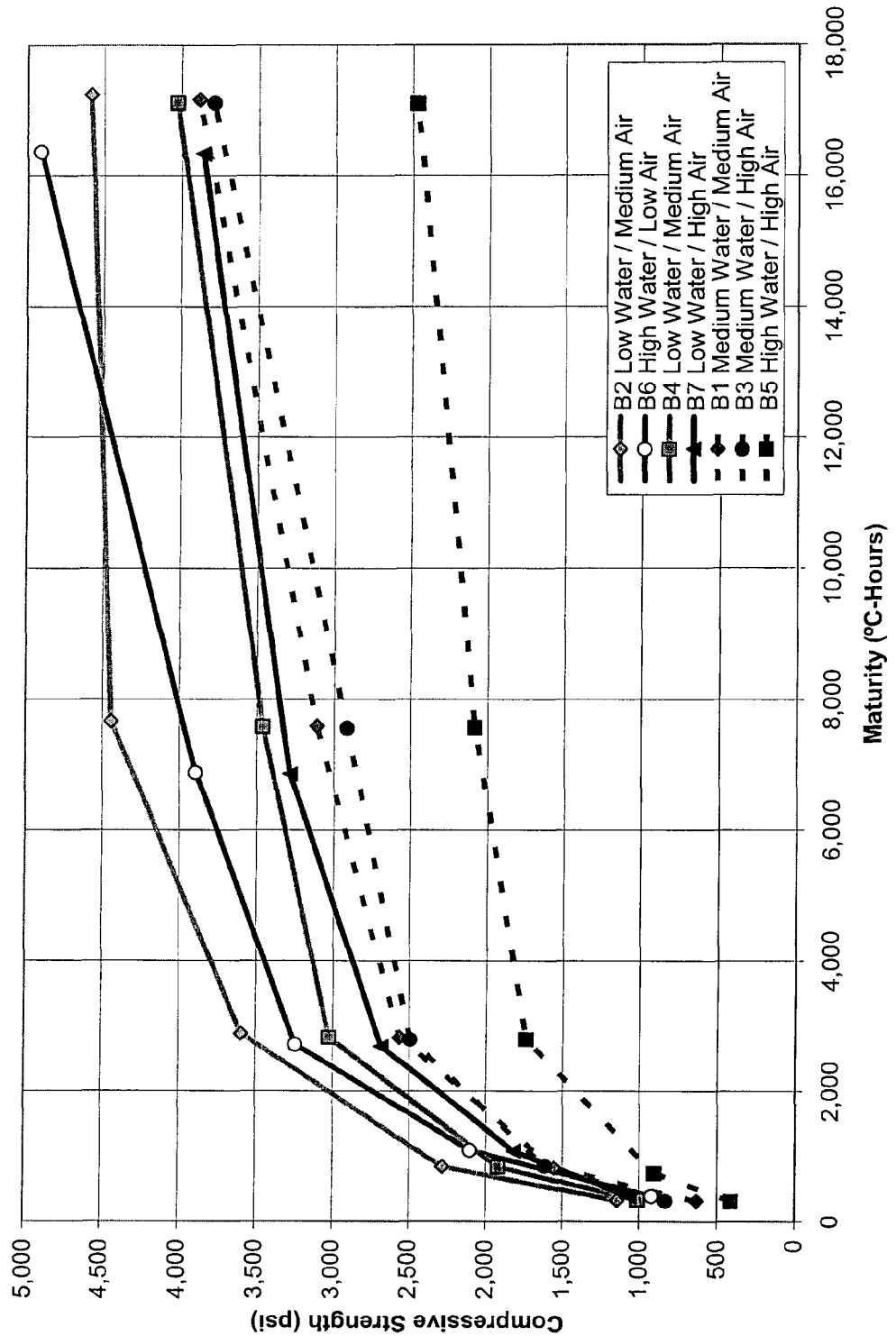
FIG. 3—Shows the strength-versus-maturity curves for the seven Enhanced Maturity calibration batches FIG. 4—Shows the strength-versus-maturity curves for the six Enhanced Maturity calibration batches.
Figure 4:
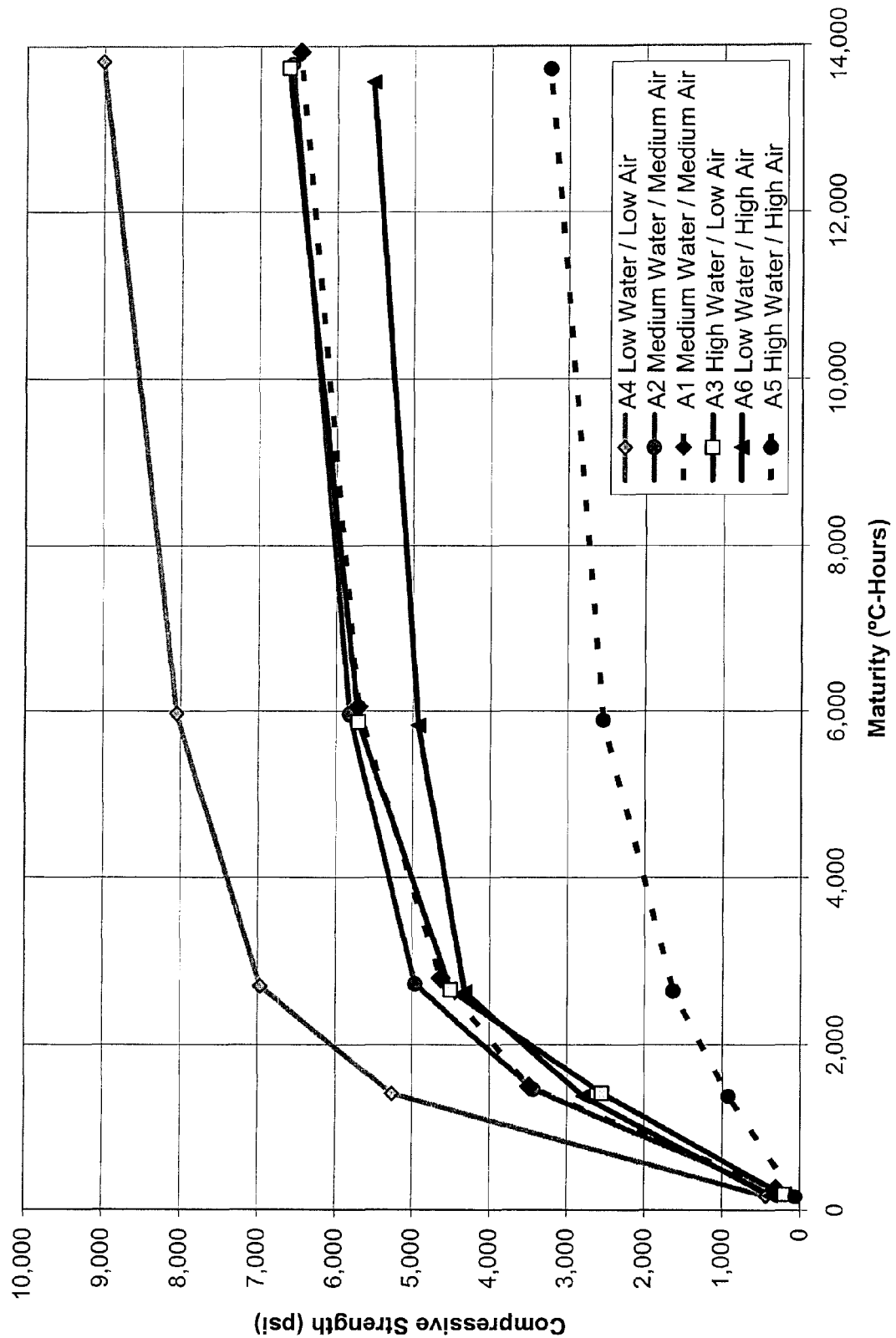
Figure 5:
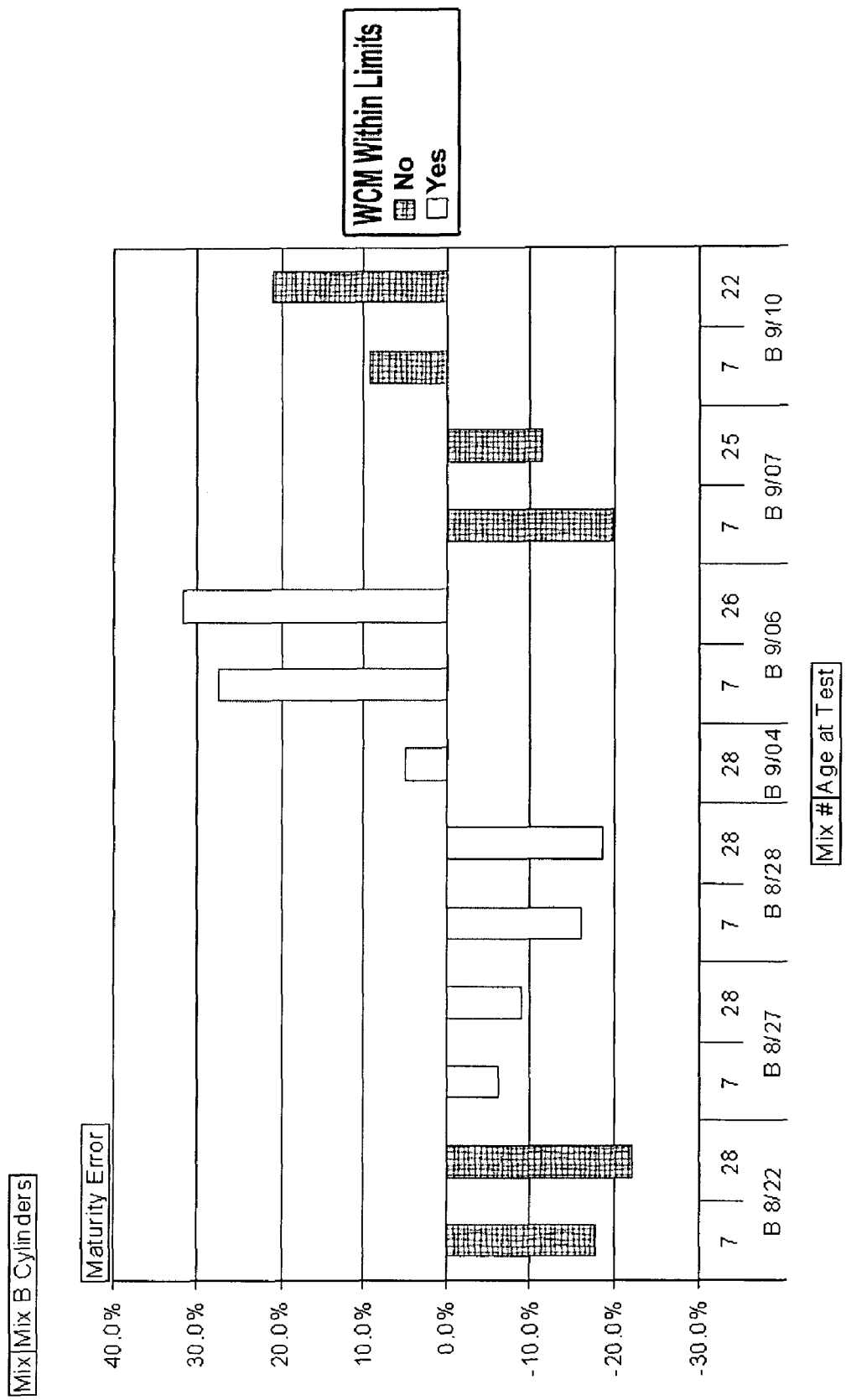
FIG. 5—Shows the prediction errors associated with predicting compressive strengths using standard maturity. The assumed "true" strengths are based on cylinders cast using Mix B concrete.
Figure 6:
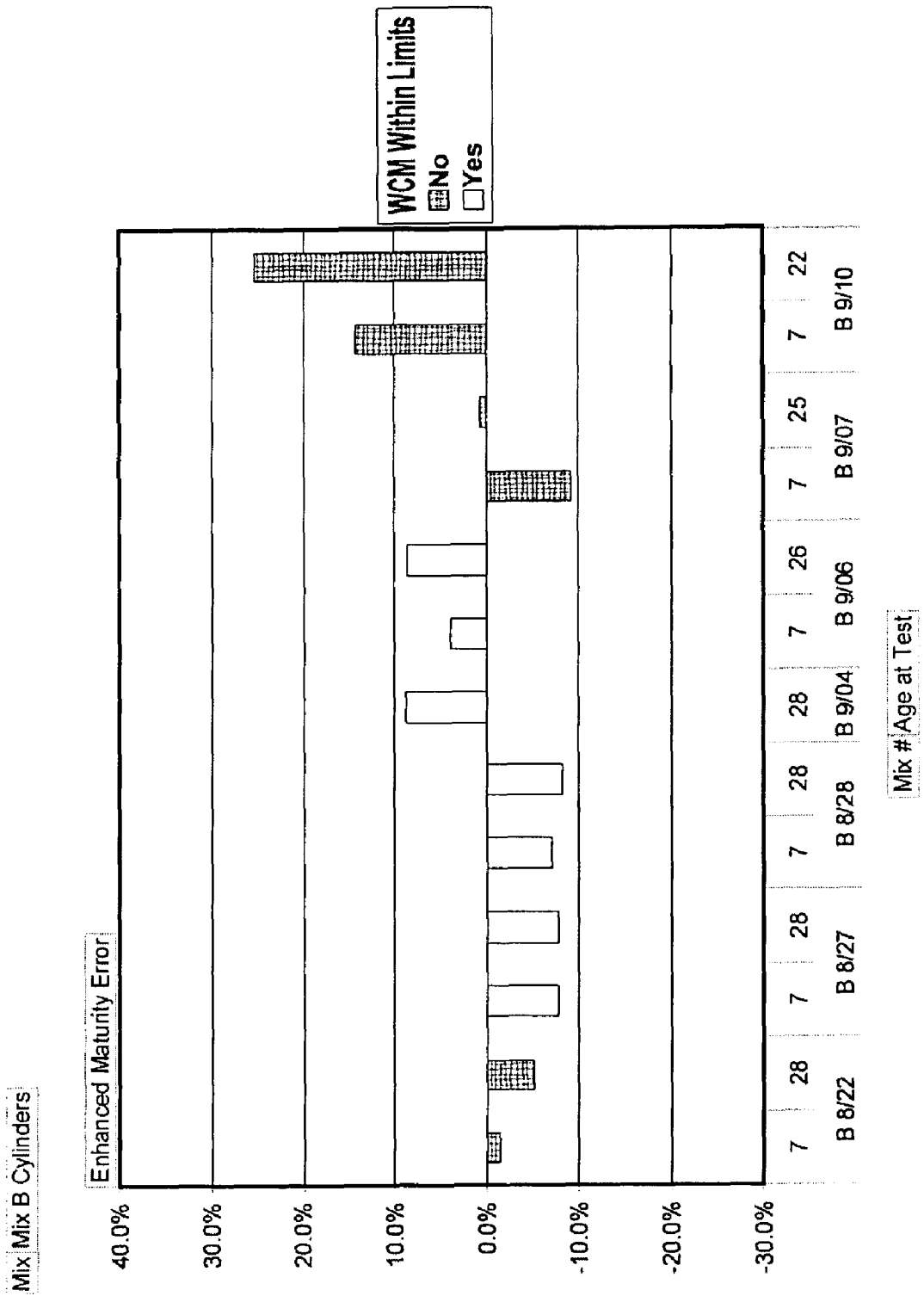
FIG. 6—Shows the prediction errors associated with predicting compressive strengths using Enhanced Maturity in accordance with the present invention. The assumed "true" strengths are based on cylinders cast using Mix B concrete.
Figure 7:
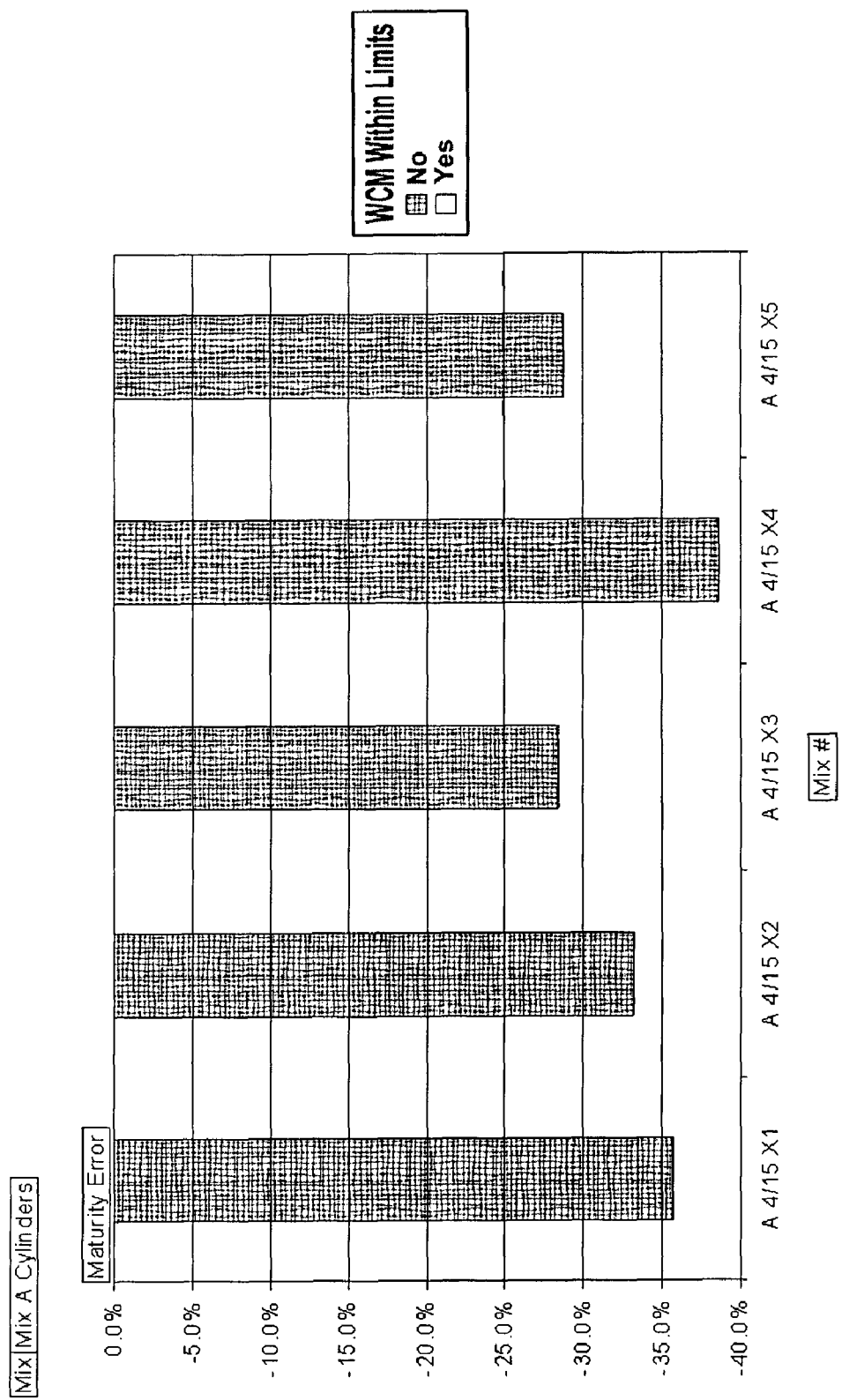
FIG. 7—Shows the prediction errors associated with predicting compressive strengths using standard maturity. The assumed "true" strengths are based on cylinders cast using Mix A concrete.
Figure 8:
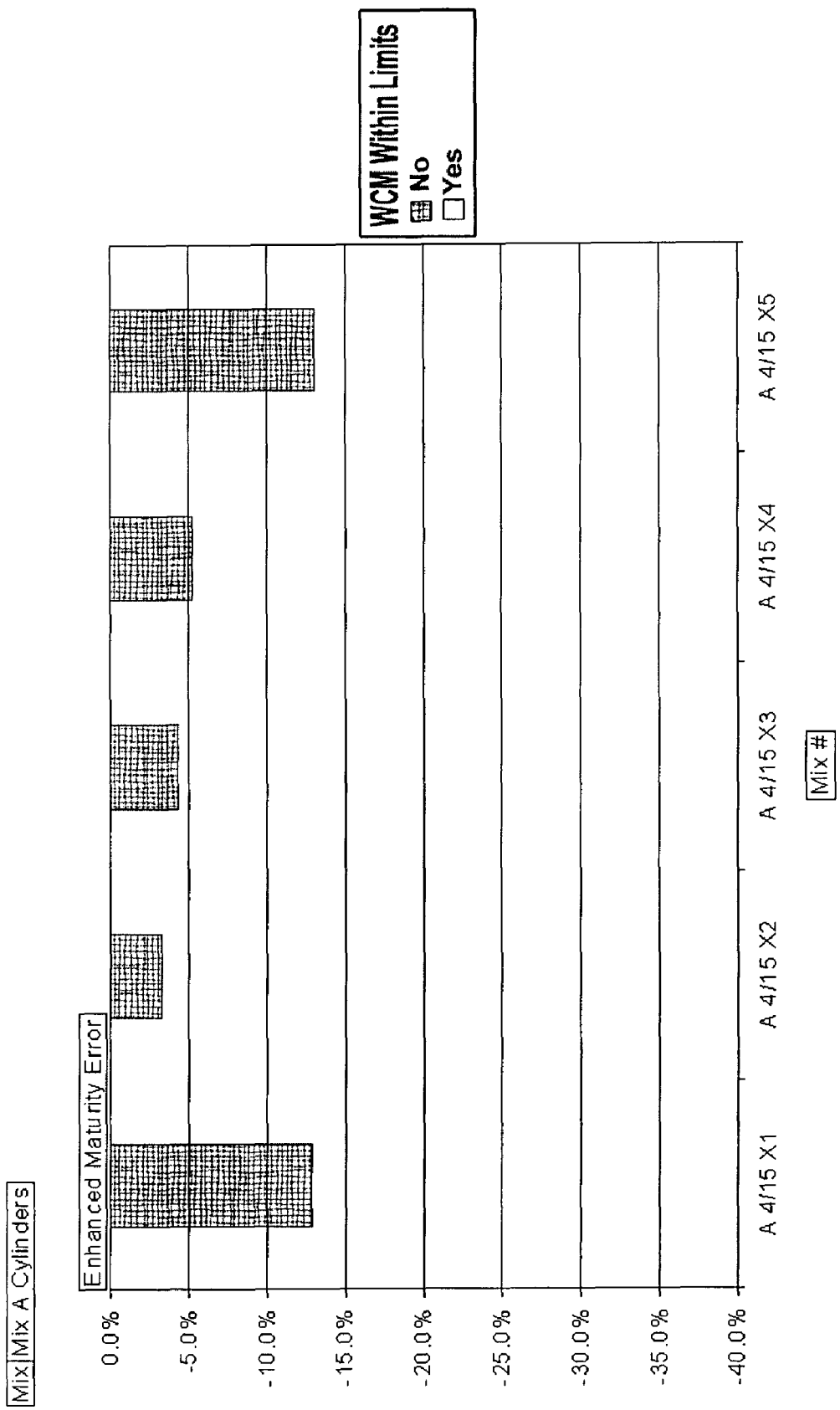
FIG. 8—Shows the prediction errors associated with predicting compressive strengths using Enhanced Maturity in accordance with the present invention. The assumed "true" strengths are based on cylinders cast using Mix A concrete.
Figure 9:
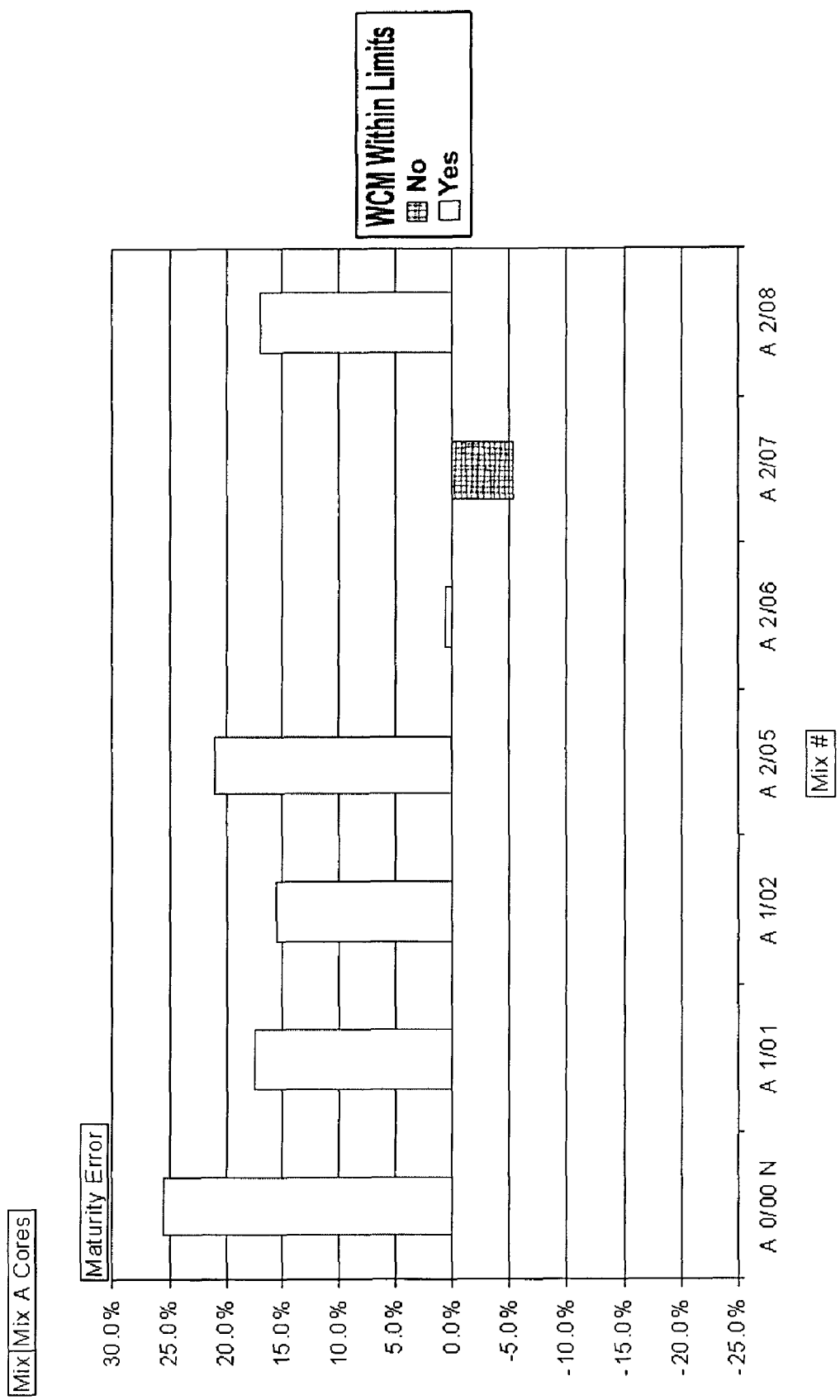
FIG. 9—Shows the prediction errors associated with predicting compressive strengths using standard maturity. The assumed "true" strengths are based on cores taken from pavement consisting of Mix A concrete.
Figure 10:
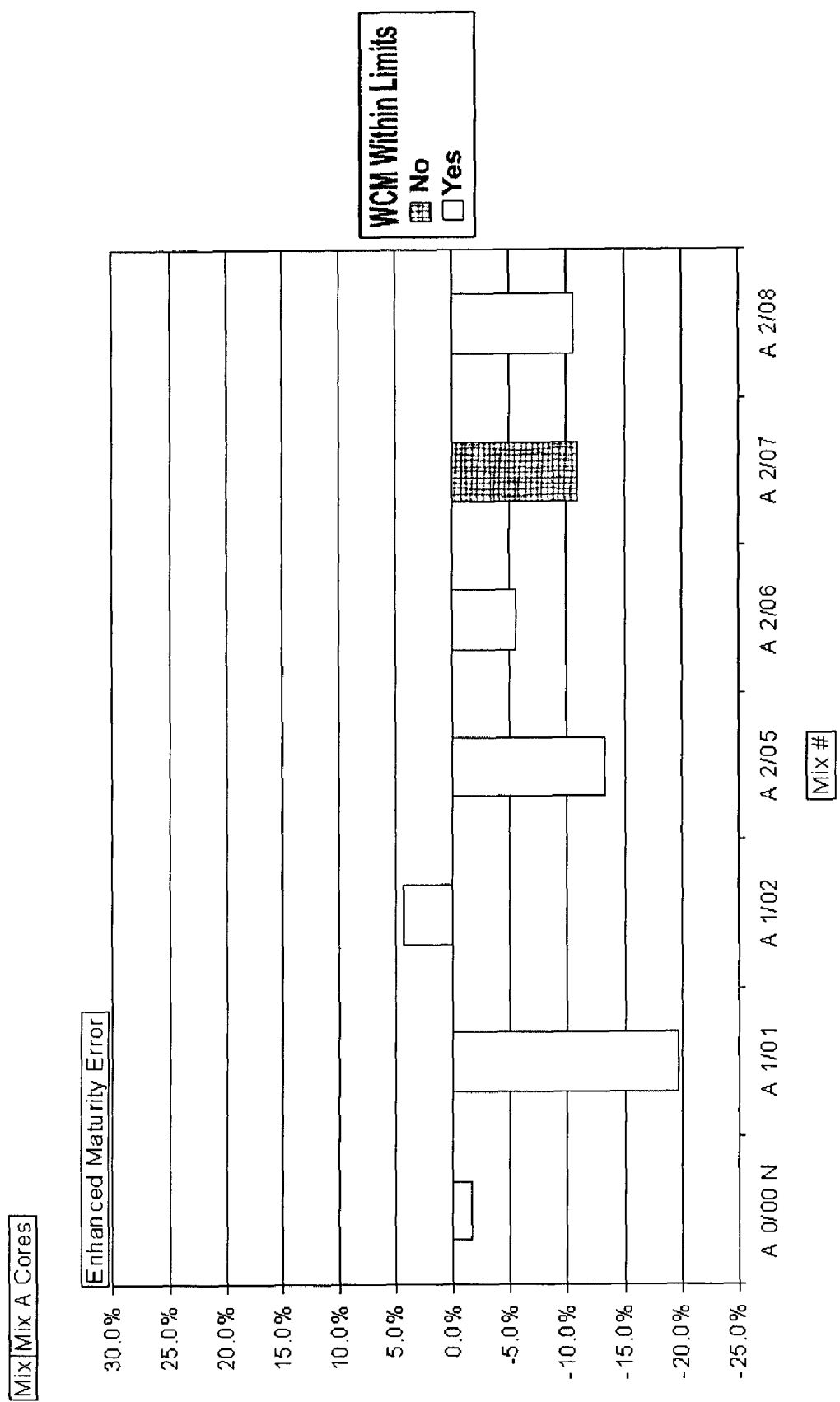
FIG. 10—Shows the prediction errors associated with predicting compressive strengths using Enhanced Maturity in accordance with the present invention. The assumed "true" strengths are based on cores taken from pavement consisting of Mix A concrete.
Figure 11:
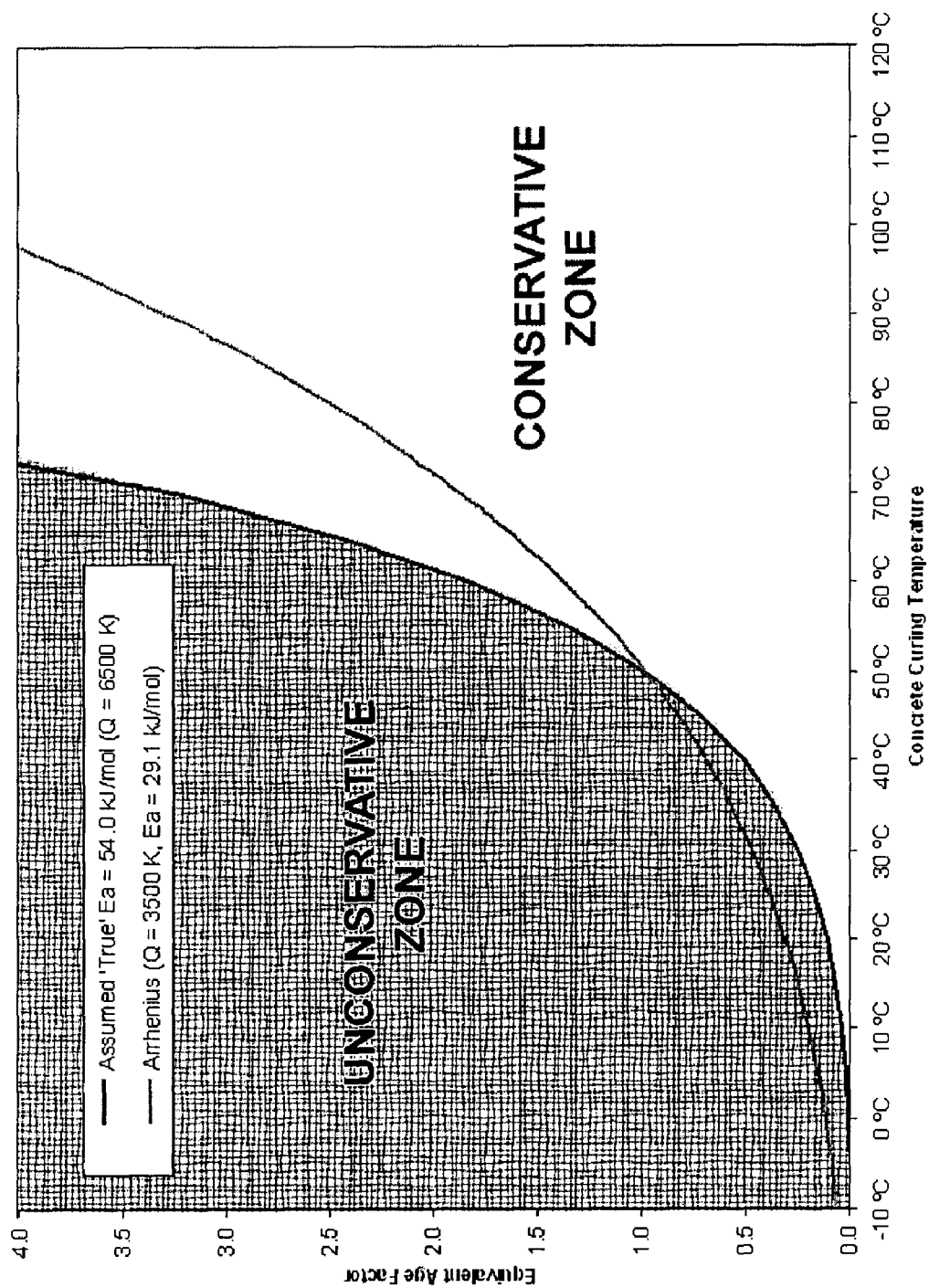
FIG. 11—Shows the unconservative potential of conventional Arrhenius maturity calculations when the calibration specimens are cured at a reference temperature of 50° C. and the in-place concrete temperatures are below 50° C.
Figure 12:
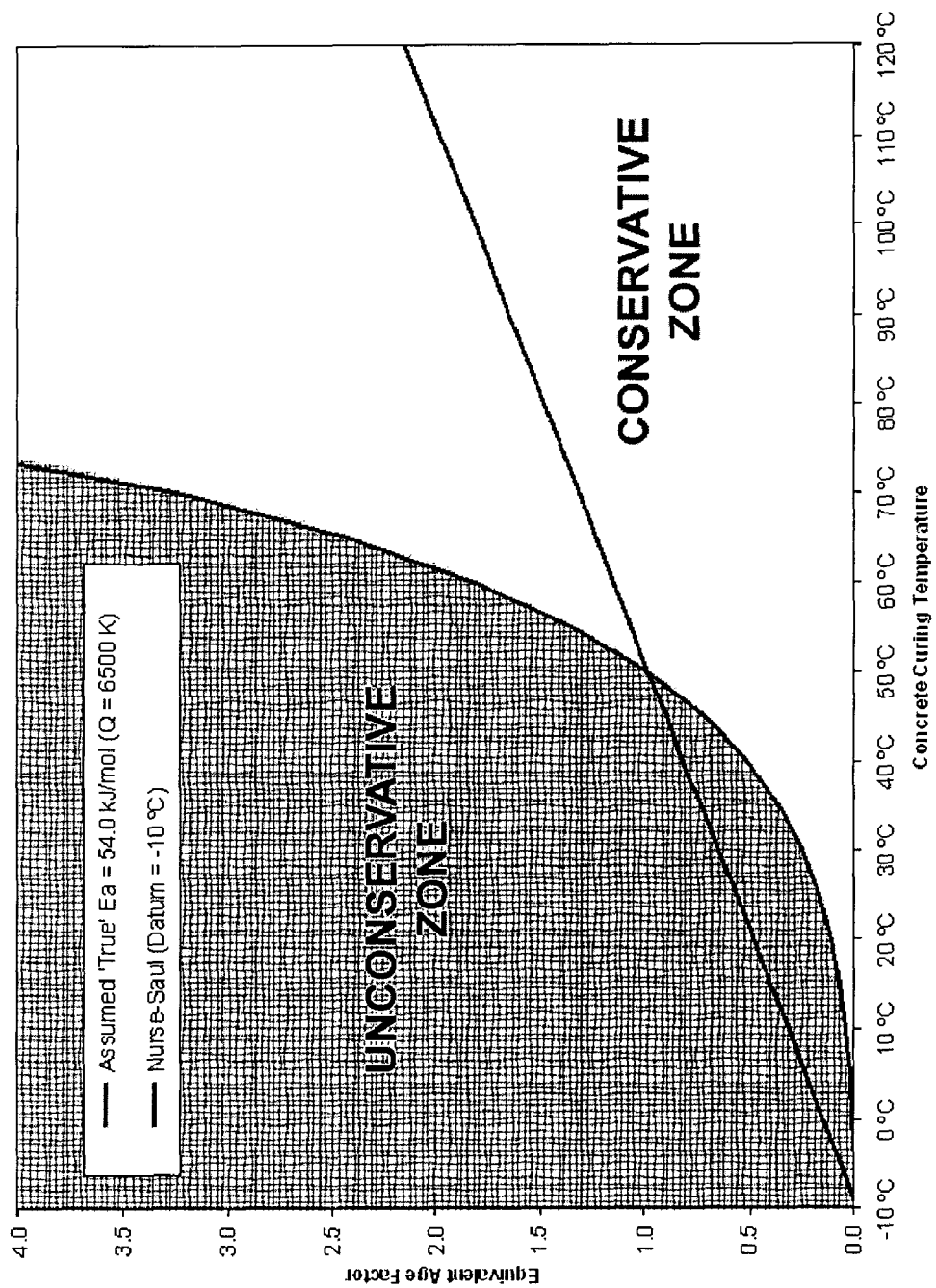
FIG. 12—Shows the unconservative potential of conventional Nurse-Saul maturity calculations when the calibration specimens are cured at a reference temperature of 50° C. and the in-place concrete temperatures are below 50° C.
Figure 13:
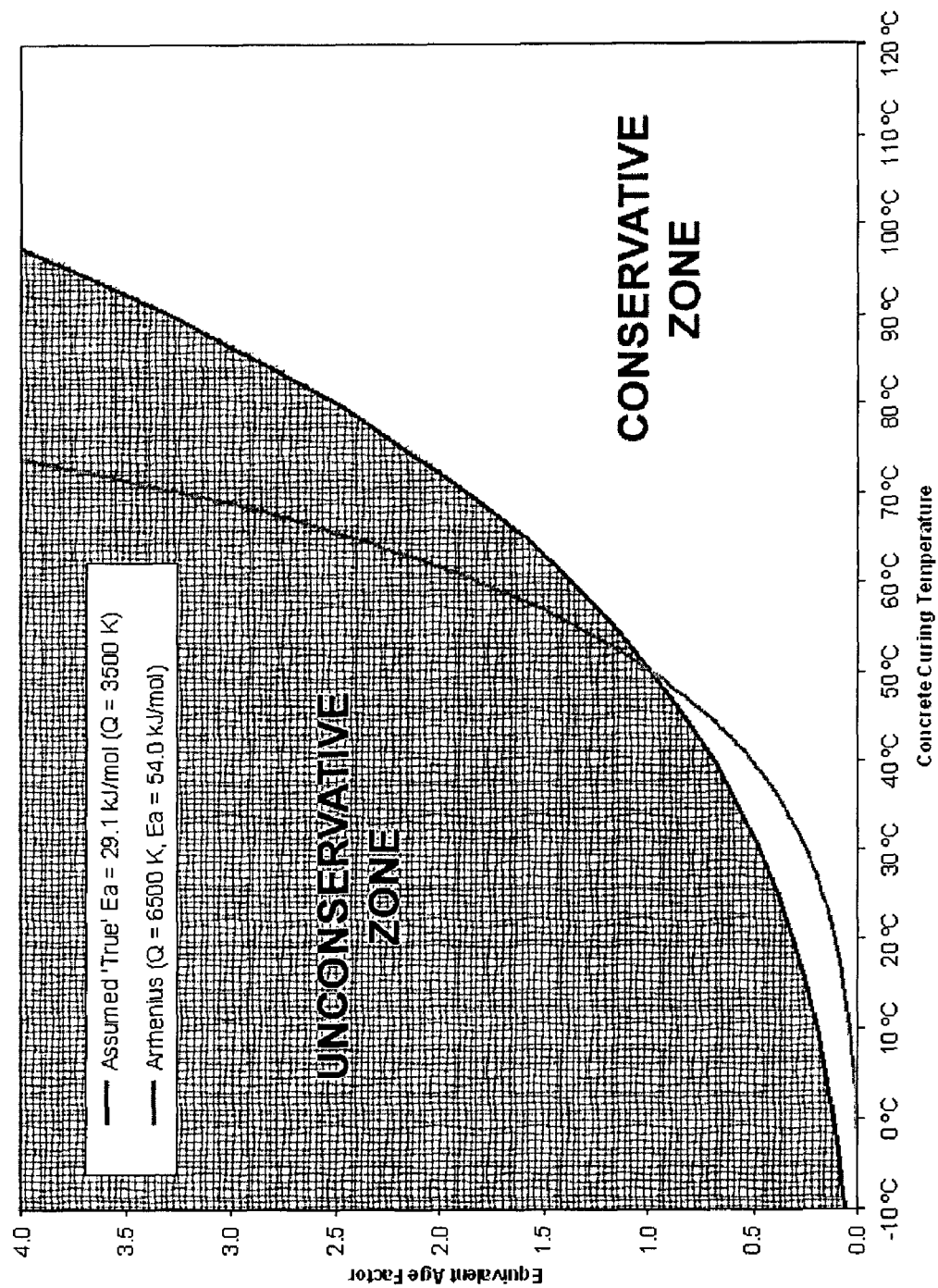
FIG. 13—Shows the unconservative potential of conventional Arrhenius maturity calculations when the calibration specimens are cured at a reference temperature of 50° C. and the in-place concrete temperatures are above 50° C.

FIGS. 1 and 2 show the treatment combinations for air and wcm for an actual implementation of the preferred embodiment of Enhanced Maturity. In addition, FIGS. 3 and 4 show the resulting strength vs. maturity data and Tables 2-5 show the standard and enhanced maturity prediction models. FIGS. 5-10 show the prediction errors associated with standard maturity and enhanced maturity methods for this particular implementation of Enhanced Maturity.

TABLE 1

Sample Treatment Combinations for Design of Experiments (DOE)

| log(Maturity) log(degrees C. - Hours) | Maturity (degrees C. - Hours) | WCM (lbs./lb.) | Air Content (%) |
|---|---|---|---|
| 2.5 | 316 | 0.32 | 1.0% |
| 3 | 1000 | 0.32 | 1.0% |
| 3.5 | 3162 | 0.32 | 1.0% |
| 4 | 10000 | 0.32 | 1.0% |
| 4.5 | 31623 | 0.32 | 1.0% |
| 2.5 | 316 | 0.32 | 9.0% |
| 3 | 1000 | 0.32 | 9.0% |
| 3.5 | 3162 | 0.32 | 9.0% |
| 4 | 10000 | 0.32 | 9.0% |
| 4.5 | 31623 | 0.32 | 9.0% |
| 2.5 | 316 | 0.42 | 1.0% |
| 3 | 1000 | 0.42 | 1.0% |
| 3.5 | 3162 | 0.42 | 1.0% |
| 4 | 10000 | 0.42 | 1.0% |
| 4.5 | 31623 | 0.42 | 1.0% |
| 2.5 | 316 | 0.42 | 9.0% |

TABLE 1-continued

Sample Treatment Combinations for Design of Experiments (DOE)

| log(Maturity) log(degrees C. - Hours) | Maturity (degrees C. - Hours) | WCM (lbs./lb.) | Air Content (%) |
|---|---|---|---|
| 3 | 1000 | 0.42 | 9.0% |
| 3.5 | 3162 | 0.42 | 9.0% |
| 4 | 10000 | 0.42 | 9.0% |
| 4.5 | 31623 | 0.42 | 9.0% |
| 2.5 | 316 | 0.37 | 5.0% |
| 3 | 1000 | 0.37 | 5.0% |
| 3.5 | 3162 | 0.37 | 5.0% |
| 4 | 10000 | 0.37 | 5.0% |
| 4.5 | 31623 | 0.37 | 5.0% |

TABLE 2

Standard Maturity for Mix B: Regression Coefficients for $(STRENGTH)^{0.5}$
Mix B [Sqrt(STRENGTH) = ]

| Term | Coefficient | p-value |
|---|---|---|
| Intercept | −100.851 | <0.0001 |
| $\log_{10}$ (MATURITY) | 70.308 | <0.0001 |
| $\log^2_{10}$ (MATURITY) | −7.532 | 0.0258 |
| Adjusted $R^2$ | 82.4% | |
| Centerpoint Prediction | 2,625 psi | |
| 95% Centerpoint Limits | 1,550 psi | 3,275 psi |
| 95% Centerpoint Range | 1,725 psi | |
| Range as % of Prediction | 66% | |

TABLE 3

Enhanced Maturity for Mix B: Regression Coefficients for $(STRENGTH)^{0.5}$
Mix B [Sqrt(STRENGTH) = ]

| Term | Coefficient | p-value |
|---|---|---|
| Intercept | −158.126 | <0.0001 |
| $\log_{10}$ (MATURITY) | 64.360 | <0.0001 |
| AIR | 1053.207 | 0.0020 |
| WCM | 158.066 | 0.6004 |
| $\log^2_{10}$ (MATURITY) | −6.667 | 0.0042 |
| AIR * WCM | −2449.238 | 0.2508 |
| Adjusted $R^2$ | 92.2% | |
| Centerpoint Prediction | 3,025 psi | |
| 95% Centerpoint Limits | 2,175 psi | 4,175 psi |
| 95% Centerpoint Range | 2,000 psi | |
| Range as % of Prediction | 66% | |

TABLE 4

Standard Maturity for Mix A: Regression Coefficients for $(STRENGTH)^{0.5}$
Mix A [Sqrt(STRENGTH) = ]

| Term | Coefficient | p-value |
|---|---|---|
| Intercept | −58.344 | <0.0001 |
| $\log_{10}$ (MATURITY) | 34.498 | <0.0001 |
| Adjusted $R^2$ | 76.1% | |
| Centerpoint Prediction | 2,700 psi | |
| 95% Centerpoint Limits | 700 psi | 6,025 psi |
| 95% Centerpoint Range | 5,325 psi | |
| Range as % of Prediction | 197% | |

TABLE 5

Enhanced Maturity for Mix A: Regression Coefficients for $\log_{10}(STRENGTH)$
Mix A [$\log_{10}(STRENGTH)$ = ]

| Term | Coefficient | p-value |
|---|---|---|
| Intercept | 2.467 | <0.0001 |
| $\log_{10}(MATURITY)$ | 2.449 | <0.0001 |
| AIR | −4.694 | <0.0001 |
| WCM | −12.374 | <0.0001 |
| $\log^2_{10}(MATURITY)$ | −0.454 | <0.0001 |
| $\log_{10}(MATURITY) * WCM$ | 2.567 | <0.0001 |
| Adjusted $R^2$ | 99.1% | |
| Centerpoint Prediction | 2,500 psi | |
| 95% Centerpoint Limits | 1,900 psi | 3,275 psi |
| 95% Centerpoint Range | 1,375 psi | |
| Range as % of Prediction | 55% | |

Enhanced Maturity Procedures

The following is an example procedure for developing prediction models using enhanced maturity:

Develop relationship curves and prediction models based on at least five (5) calibration batches using the following water and air contents: Low Water/Low Air; High Water/Low Air; Low Water/High Air; High Water/High Air and Medium Water/Medium Air. The "Low" and "High" values should be slightly more extreme than the most extreme conditions expected during normal concrete production. [A second center point batch (Medium Water/Medium Air) is advisable (but not required) to provide an indication of anticipated levels of batch-to-batch variability during normal concrete production.] The ranges for air content for the data shown on FIGS. 1 and 2 was 1% ("Low") to 9% ("high"). Similarly, the ranges for water-to-cementitious-materials ratio was 0.42 ("low") to 0.62 ("high"). Actual ranges chosen will depend upon the specific mix designs being used and the anticipated variability in those parameters during actual production operations.

Test each batch for unit weight, air content and water-to-cementitious-materials ratio (wcm). Unit weight can be measured in accordance with ASTM C 138 or other suitable methods. Air content can be measured in accordance with ASTM C 231, C 173 or other suitable methods. Water-to-cementitious-materials can be measured in accordance with the instructions detailed previously in this specification. To increase the precision of the respective measurements, one may take multiple measurements of each characteristic for each batch and use the average values when performing the regression analysis.

Cast a minimum of twenty (20) specimens from each calibration batch. Instrument two (2) specimens from each batch with maturity sensors.

Test one-sixth of the specimens (excluding the instrumented specimens) from each batch at each maturity age and use the average strength values and the average of the two maturity specimens for each batch.

Tabulate the data by MATURITY, $\log_{10}(MATURITY)$, AIR, WCM and STRENGTH. If five calibration batches are produced, there should be 6×5 (=30) rows of data in the table.

Perform a "backward elimination" regression analysis with STRENGTH as the dependent (or response) variable and $\log_{10}(MATURITY)$, AIR, WCM, $\log^2_{10}(MATURITY)$, $\log_{10}(MATURITY)*AIR$, $\log_{10}(MATURITY)*WCM$ and AIR*WCM as the independent variables. If the plot of residual errors vs. predicted values resembles a sideways cone or funnel shape, redo the regression analysis using $STRENGTH^{0.5}$ or $\log_{10}(STRENGTH)$ as the dependent variable instead of STRENGTH.

For enhanced maturity, the prediction model developed from the above regression analysis will be used for determining in place concrete strengths. To determine concrete strength in the field, perform the following steps:

1. Develop a prediction model for STRENGTH (as a function of MATURITY, AIR and WCM) as described above.
2. Measure and record the air content and wcm for the concrete to be tested. Accurate and precise measurements of air and wcm are extremely important.
3. Place a maturity sensor into the structure. The term "maturity sensor" as used herein refers to a device for recording the temperature of a structure. Maturity sensors are known in the art. One suitable maturity sensor is sold under the trademark "Intellirock" and is obtainable from Nomadics, Inc. of Stillwater, Okla.
4. Whenever a strength measurement is desired, check the current maturity of the concrete, then calculate STRENGTH using the prediction model developed in Step 1 by plugging in the values for current MATURITY and the AIR and WCM values recorded during concrete placement. The values were plugged in without extrapolating beyond the levels of MATURITY, AIR and/or WCM. Moreover, it is strongly recommended that the values be utilized without extrapolating beyond the levels of MATURITY, AIR and/or WCM included in the calibration testing.

Moisture-Loss Maturity

Moisture-Loss Maturity utilizes the maturity method for determining the critical times for protecting a given concrete mass from moisture loss and/or for providing additional moisture to the concrete mass. Heretofore, the maturity method has been used primarily as a strength-determination method. The maturity method for estimating concrete strength produces an estimate of strength based on the actual temperature history experienced by the concrete mass.

The following is an example of the making and using of the Moisture-Loss Maturity system and method of the present invention:

1. Establish a desired degree of hydration (to be usually expressed as a percentage of complete hydration) at which moisture-loss-protection activities will be allowed to cease. The desirable degree of hydration can be determined via a correlation between measured degree of hydration and the durability property of interest (such as permeability or durability factor). Permeability can be measured in accordance with ASTM C 1202 or other suitable methods. Durability factor can be measured in accordance with ASTM C 666 or other suitable methods. Establishing the correlation involves testing multiple specimens for the desired durability property(ies) at the same time that their respective degree-of-hydration is measured. A possible embodiment of the present invention would involve a state highway agency's experimental determination of desirable degree of hydration (for example, 75%) as a specification value to be applied to all mixes throughout the state, followed by mix-specific determination of the unique degree-of-hydration versus maturity curves for the various mixes to be used.

2. Determine a mix-specific hydration-maturity relationship as follows.
   a. Cast a plurality of specimens from a single batch of concrete. For example, a minimum of twenty-three (23) specimens can be cast from a single batch of concrete according to ASTM C 31 or ASTM C 192 using the same mix design to be used in normal production operations. Instrument at least one and preferably at least two (2) of the specimens with maturity sensors such as the intelliRock™ maturity logger obtainable from Nomadics, Inc. of Stillwater, Okla.
   b. Cure the specimens in saturated limewater (preferred) or a moist room or moist cabinet in accordance with ASTM C 31 or ASTM C 192.
   c. Test a plurality of the specimens for strength (excluding the instrumented specimens). For example, when 23 samples are prepared, about one-seventh of the specimens can be tested for strength (excluding the instrumented specimens) at each maturity age (e.g. 1, 3, 7, 14, 28, 56 and 90 days) and record the average of the strength values of the three test specimens for that maturity age level and the average of the maturity values of the two instrumented specimens at the time the strength tests are performed. If the Nurse-Saul method is used for maturity determinations, the maturity values will be in units of temperature X time, such as degree-hours. If the Arrhenius method is utilized, the maturity values will be in units of equivalent age, such as days or hours. The strength at the final maturity age level can be taken as "ultimate" strength of the concrete or assumed to be some percentage of ultimate strength. For example, the specifying agency may state that the 90-day strengths will be assumed to be 95% of ultimate strength.
   d. Once the tests are completed for the final maturity age (e.g. 90-day specimens are tested for strength and maturity), compute the percentage of the average strength compared to the ultimate strength for each maturity age. (For example, if the average 90-day strength is 8,000 psi, if the specifying agency states that the 90-day strength will be assumed to be 95% of ultimate strength and if the average 3-day strength is 2,000 psi, then the maturity age represented by the 3-day specimens corresponds to 23.8% of ultimate strength. This is calculated as 8,000 divided by 95% to find ultimate strength, which in this case would be 8,421 psi. The percentage of ultimate strength at three days would then be 2,000 divided by 8,421, which would be 23.8%.) These percentage-of-ultimate-strength numbers can then be taken to represent the percent-of-hydration for each maturity age, with the "ultimate strength" value being 100% (i.e. complete hydration).
   e. Plot the hydration-maturity data on a graph (such as shown in FIG. 1) with maturity as the independent variable (x-axis) and percent-of-hydration as the dependent variable (y-axis).
3. Determine the threshold maturity value corresponding to the desired degree of hydration. This can be accomplished by interpolating between the two data points that bracket the desired hydration threshold and/or by fitting the hydration-maturity data with a best-fit curve, then calculating the threshold maturity value that matches the desired degree of hydration using the equation for the best-fit curve. The best-fit curve can be a curve drawn manually such that a roughly equal number of points lie both above and below the corresponding curve or can be accomplished mathematically using standard regression techniques (such as ordinary least squares fit with a logarithmic transformation of the maturity values) or can be accomplished using curve-fitting software (such as Microsoft Excel's "trendline" feature). If mathematical or software techniques are used, an equation can be subsequently computed or displayed. The equation may take any number of forms, such as a polynomial (e.g. PercentHydration=ConstantA+Maturity+Maturity$^2$+ Maturity$^3$+ . . . +Maturity$^n$), or a logarithmic equation (e.g. PercentHydration=ConstantB+log(Maturity)), or logarithmic polynomial (e.g. PercentHydration=ConstantC+log(Maturity)+log$^2$(Maturity)).
4. Place one or more maturity sensors into the concrete for which moisture-loss protection is to be carried out (while the concrete is in its plastic state, e.g. concurrent with the concrete being placed into its forms).
5. Activate the maturity sensor(s) to begin calculating and/or recording maturity.
6. Provide adequate protection from moisture loss and/or additional moisture to the concrete. Monitor the maturity of the concrete until the threshold value is achieved. Once the concrete has achieved the required threshold maturity (and, thus, the required threshold degree of hydration), moisture-loss protection can be terminated.

A variant of Moisture-Loss Maturity involves conducting the hydration-maturity calibration using Enhanced Maturity methods in lieu of conventional maturity methods. The embodiment of Moisture-Loss Maturity using Enhanced Maturity would involve the use of a design of experiments (DOE). An example would be performing the DOE using three factors (maturity, water-to-cementitious-materials ratio and air content) to establish a single equation to predict degree of hydration for a range of concrete batch proportions. The advantage of this variant is that the prediction equation is then equally applicable to all batches of the given concrete mix design, not just those with a specific water-to-cementitious-materials ratio and air content. The equation will generally be based on a N×2×2 full-factorial experiment on maturity, water-to-cementitious-materials ratio (wcm) and air content. (N represents the number of maturity ages tested. For strength-based degree-of-hydration measurements, the value of N is constrained by the number of test specimens cast. For non-destructive degree-of-hydration measurements, such as weight-gain (or unit-weight-gain), N theoretically has no limits.) As with the previous embodiments mentioned, this variant can be used with strength, weight, unit weight or any other suitable method for determining degree of hydration. The equations derived from Moisture-Loss Maturity using Enhanced Maturity could take any number of forms, such as:

$$\text{PercentHydration} = B_1 + B_2*\text{Maturity} + B_3*\text{WCM} + B_4*\text{AirContent} + B_5*\text{Maturity}*\text{WCM} + B_6*\text{Maturity}*\text{AirContent} + B_7*\text{WCM}*\text{AirContent} + B_8*\text{Maturity}^2 + B_9*\text{Maturity}^3$$

or $$\text{PercentHydration} = B_1 + B_2*\text{Maturity} + B_3*\text{WCM} + B_4*\text{AirContent} + B_5*\text{Maturity}*\text{WCM} + B_6*\text{Maturity}*\text{AirContent} + B_7*\text{WCM}*\text{AirContent} + B_8*\text{Maturity}^2 + B_9*\text{Maturity}^3 + B_{10}*\text{WCM}^2 + B_{11}*\text{AirContent}^2$$

where $B_i$=calibration constants to be determined by the experimentation and subsequent statistical analysis of the experimental results.

Improved Maturity

As discussed above, Improved Maturity represents a novel method and system to ensure conservatism when using maturity methods to determine the strength of concrete. The method can be implemented as a protocol for use with the Arrhenius maturity method and, similarly, as a protocol for use with the Nurse-Saul maturity method. The benefits of Improved Maturity are derived from the fact that a conservative maturity calculation is guaranteed, irrespective of the "true" apparent activation energy of the concrete's constituent cementitious and pozzolanic materials. Improved Maturity can be readily applied to the Arrhenius method for determining strength from maturity or to the Nurse-Saul method, or to some variant thereof, or to any similar methods. The application of Improved Maturity to the Arrhenius method results in an Improved Arrhenius method and, separately, the application of Improved Maturity to the Nurse-Saul method results in an Improved Nurse-Saul method. A protocol for applying the invention to the Arrhenius method generally involves determining the reference temperature for a given calibration batch, then performing subsequent Arrhenius maturity calculations using a "high" apparent activation energy value (e.g. 54 kJ/mole) at temperatures below the reference temperature and using a "low" apparent activation energy value (e.g. 29 kJ/mole) at temperatures above the reference temperature, creating a dichotomous exponential model relating the rate of cementitious hydration to variations in temperature for a given concrete mix design. This dichotomous model remains conservative for strength predictions irrespective of the "true" apparent activation energy of the concrete mix design and irrespective of the curing temperature of the concrete. A protocol for applying Improved Maturity to the Nurse-Saul method closely follows the Improved Arrhenius protocol. The resulting Improved Nurse-Saul model is a dichotomous straight-line (rather than exponential) model wherein each portion of the model is tangential or nearly tangential (at the reference temperature) to its respective portion of the dichotomous Arrhenius model. Various Improved Nurse-Saul protocols are also presented that simplify the end use of the Improved Nurse-Saul method.

TABLE 6

Unconservative Nature of Conventional Maturity Calculations (Nurse-Saul and Arrhenius) at $T_{ref}$ = 50° C.

| Temperature | | To = −10° C. | | Q = 3500 K | | Q = 5000 K | | Q = 6500 K | |
|---|---|---|---|---|---|---|---|---|---|
| (° C.) | (° F.) | EAF | % Error | EAF | % Error | EAF | % Error | EAF | % Error |
| Equivalent Age Errors (if True Q = 3500 K) | | | | | | | | | |
| −10 | 14 | 0.00 | N/A | 0.08 | 0.0% | 0.03 | −65.3% | 0.01 | −88.0% |
| −5 | 23 | 0.08 | −23.0% | 0.11 | 0.0% | 0.04 | −61.4% | 0.02 | −85.1% |
| 0 | 32 | 0.17 | 21.3% | 0.14 | 0.0% | 0.06 | −57.3% | 0.03 | −81.8% |
| 5 | 41 | 0.25 | 44.4% | 0.17 | 0.0% | 0.08 | −52.8% | 0.04 | −77.8% |
| 10 | 50 | 0.33 | 54.2% | 0.22 | 0.0% | 0.11 | −48.1% | 0.06 | −73.1% |
| 15 | 59 | 0.42 | 55.5% | 0.27 | 0.0% | 0.15 | −43.1% | 0.09 | −67.7% |
| 20 | 68 | 0.50 | 51.6% | 0.33 | 0.0% | 0.20 | −37.8% | 0.13 | −61.4% |
| 25 | 77 | 0.58 | 44.8% | 0.40 | 0.0% | 0.27 | −32.3% | 0.18 | −54.1% |
| 30 | 86 | 0.67 | 36.3% | 0.49 | 0.0% | 0.36 | −26.4% | 0.26 | −45.8% |
| 35 | 95 | 0.75 | 27.1% | 0.59 | 0.0% | 0.47 | −20.2% | 0.38 | −36.4% |
| 40 | 104 | 0.83 | 17.8% | 0.71 | 0.0% | 0.61 | −13.8% | 0.53 | −25.7% |
| 45 | 113 | 0.92 | 8.7% | 0.84 | 0.0% | 0.78 | −7.0% | 0.73 | −13.6% |
| 50 | 122 | 1.00 | 0.0% | 1.00 | 0.0% | 1.00 | 0.0% | 1.00 | 0.0% |
| 55 | 131 | 1.08 | −8.2% | 1.18 | 0.0% | 1.27 | 7.3% | 1.36 | 15.2% |
| 60 | 140 | 1.17 | −15.7% | 1.38 | 0.0% | 1.59 | 15.0% | 1.83 | 32.2% |
| 65 | 149 | 1.25 | −22.7% | 1.62 | 0.0% | 1.99 | 22.9% | 2.44 | 51.0% |
| 70 | 158 | 1.33 | −29.1% | 1.88 | 0.0% | 2.47 | 31.1% | 3.23 | 71.9% |
| 80 | 176 | 1.50 | −40.3% | 2.51 | 0.0% | 3.73 | 48.4% | 5.53 | 120.2% |
| 90 | 194 | 1.67 | −49.5% | 3.30 | 0.0% | 5.51 | 66.8% | 9.18 | 178.3% |
| 100 | 212 | 1.83 | −57.1% | 4.27 | 0.0% | 7.96 | 86.4% | 14.84 | 247.3% |
| 110 | 230 | 2.00 | −63.4% | 5.46 | 0.0% | 11.30 | 107.0% | 23.40 | 328.5% |
| 120 | 248 | 2.17 | −68.6% | 6.89 | 0.0% | 15.76 | 128.7% | 36.03 | 423.0% |
| 130 | 266 | 2.33 | −72.8% | 8.59 | 0.0% | 21.61 | 151.4% | 54.32 | 532.0% |
| Equivalent Age Errors (if True Q = 6500 K) | | | | | | | | | |
| −10 | 14 | 0.00 | N/A | 0.08 | 732.2% | 0.03 | 188.5% | 0.01 | 0.0% |
| −5 | 23 | 0.08 | 418.1% | 0.11 | 572.7% | 0.04 | 159.4% | 0.02 | 0.0% |
| 0 | 32 | 0.17 | 564.5% | 0.14 | 448.0% | 0.06 | 134.1% | 0.03 | 0.0% |
| 5 | 41 | 0.25 | 549.6% | 0.17 | 349.7% | 0.08 | 112.1% | 0.04 | 0.0% |
| 10 | 50 | 0.33 | 473.0% | 0.22 | 271.6% | 0.11 | 92.8% | 0.06 | 0.0% |
| 15 | 59 | 0.42 | 380.7% | 0.27 | 209.2% | 0.15 | 75.8% | 0.09 | 0.0% |
| 20 | 68 | 0.50 | 292.5% | 0.33 | 158.8% | 0.20 | 60.9% | 0.13 | 0.0% |
| 25 | 77 | 0.58 | 215.6% | 0.40 | 118.0% | 0.27 | 47.6% | 0.18 | 0.0% |
| 30 | 86 | 0.67 | 151.6% | 0.49 | 84.6% | 0.36 | 35.9% | 0.26 | 0.0% |
| 35 | 95 | 0.75 | 99.8% | 0.59 | 57.2% | 0.47 | 25.4% | 0.38 | 0.0% |
| 40 | 104 | 0.83 | 58.5% | 0.71 | 34.5% | 0.61 | 16.0% | 0.53 | 0.0% |
| 45 | 113 | 0.92 | 25.8% | 0.84 | 15.7% | 0.78 | 7.6% | 0.73 | 0.0% |
| 50 | 122 | 1.00 | 0.0% | 1.00 | 0.0% | 1.00 | 0.0% | 1.00 | 0.0% |
| 55 | 131 | 1.08 | −20.3% | 1.18 | −13.2% | 1.27 | −6.8% | 1.36 | 0.0% |
| 60 | 140 | 1.17 | −36.2% | 1.38 | −24.3% | 1.59 | −13.0% | 1.83 | 0.0% |
| 65 | 149 | 1.25 | −48.8% | 1.62 | −33.8% | 1.99 | −18.6% | 2.44 | 0.0% |
| 70 | 158 | 1.33 | −58.8% | 1.88 | −41.8% | 2.47 | −23.7% | 3.23 | 0.0% |
| 80 | 176 | 1.50 | −72.9% | 2.51 | −54.6% | 3.73 | −32.6% | 5.53 | 0.0% |
| 90 | 194 | 1.67 | −81.9% | 3.30 | −64.1% | 5.51 | −40.1% | 9.18 | 0.0% |
| 100 | 212 | 1.83 | −87.6% | 4.27 | −71.2% | 7.96 | −46.3% | 14.84 | 0.0% |

TABLE 6-continued

Unconservative Nature of Conventional Maturity Calculations
(Nurse-Saul and Arrhenius) at $T_{ref}$ = 50° C.

| Temperature | | To = −10° C. | | Q = 3500 K | | Q = 5000 K | | Q = 6500 K | |
|---|---|---|---|---|---|---|---|---|---|
| (° C.) | (° F.) | EAF | % Error | EAF | % Error | EAF | % Error | EAF | % Error |
| 110 | 230 | 2.00 | −91.5% | 5.46 | −76.7% | 11.30 | −51.7% | 23.40 | 0.0% |
| 120 | 248 | 2.17 | −94.0% | 6.89 | −80.9% | 15.76 | −56.3% | 36.03 | 0.0% |
| 130 | 266 | 2.33 | −95.7% | 8.59 | −84.2% | 21.61 | −60.2% | 54.32 | 0.0% |

The following is an example of the Improved Arrhenius protocol:

1. Cast a number of test specimens (e.g. 20) to be cured in a water tank, moist room or moist cabinet and subsequently destructively-tested for strength (e.g. compressive, flexural, and splitting-tensile).
2. Instrument at least one and preferably at least two (2) of the specimens with maturity sensors, e.g., temperature recording devices (such as the intelliRock TPL-01 temperature profile logger obtainable from Nomadics, Inc. of Stillwater, Okla.) to record internal concrete temperatures over the period of interest (e.g. 28 days). Begin recording internal concrete temperatures as soon as the specimens are cast.
3. Destructively test a subset of the specimens (e.g. three at a time) at different time intervals (e.g. 1, 3, 5, 7, 14 and 28 days). Record the strengths of the specimens along with the elapsed time (i.e. age) at which the specimens were broken.
4. After all the specimens have been tested for strength, determine the average (or weighted average) of the internal concrete temperatures for the entire period. The average would simply involve adding up all the evenly-spaced temperature readings for the entire period and dividing by the number of readings. Alternatively, a weighted average could be used to give more weight to those temperatures experienced early in the hydration process, since experience and historical data have shown that the early temperature history for concrete specimens has a greater impact on the ultimate strength and strength gain than temperature fluctuations experienced later in the life of the specimens. Any number of weighted-average equations could be used. An example weighted-average equation is as follows:

$$T_{WA} = \frac{\sum_{i=1}^{N}\left[T \cdot \left(\frac{\Delta t_i}{t_i}\right)^{\frac{1}{3}}\right]}{\sum_{i=1}^{N}\left[\left(\frac{\Delta t_i}{t_i}\right)^{\frac{1}{3}}\right]}$$

where
$T_{WA}$=weighted average of the recorded concrete temperatures (in ° C.)
N=number of temperature recordings throughout the curing period (in hours or days)
$\Delta t_i$=length of the time interval between temperature recording i and i−1 (in hours or days)
$t_i$=elapsed time up through temperature recording i (in hours or days)
T=recorded temperature at time $t_i$ (in ° C.)

Figure 14:
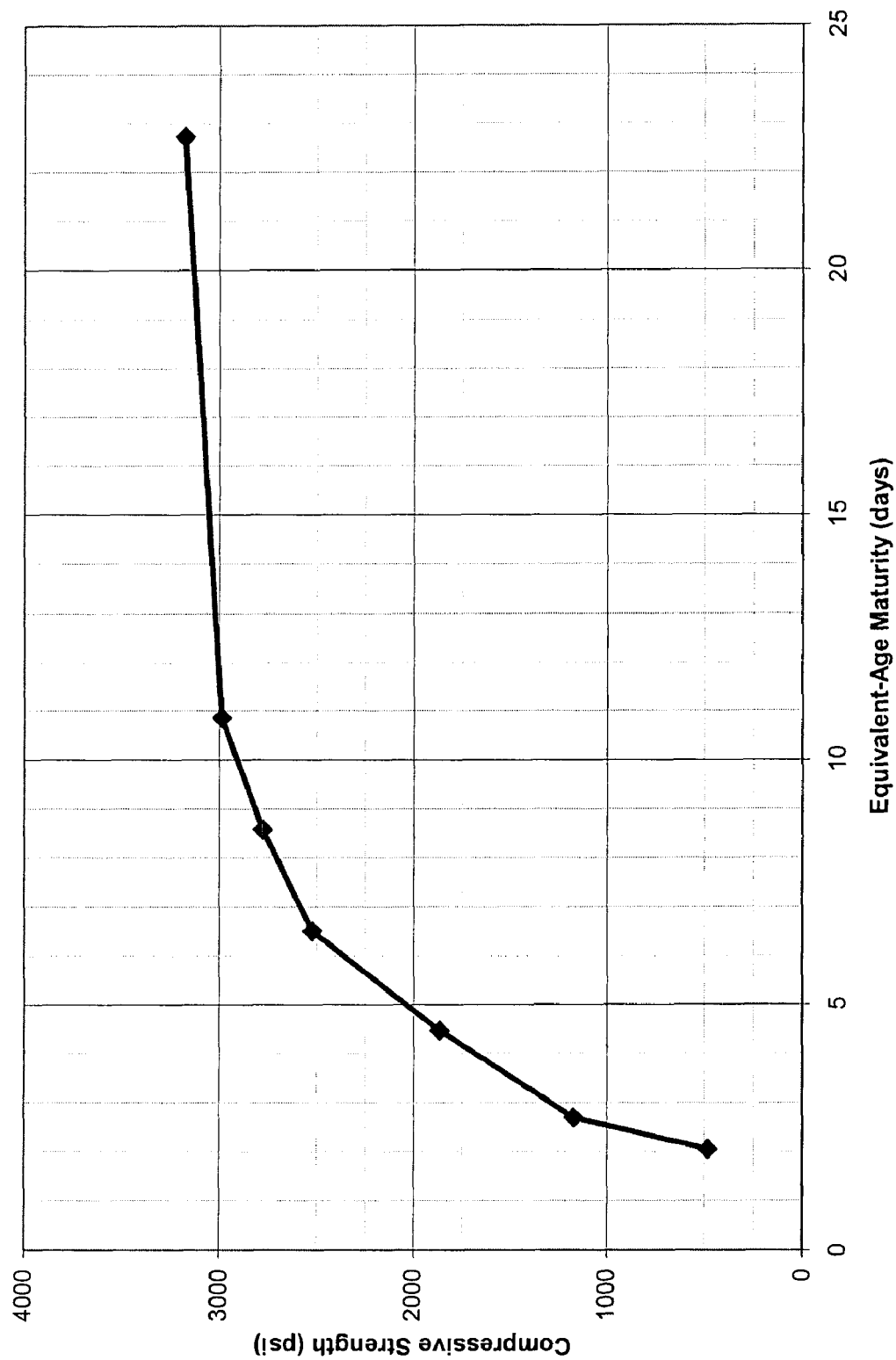
FIG. 14—Shows an example strength-maturity relationship curve based on Arrhenius maturity calculations (i.e. maturity is expressed as equivalent age).

5. Establish the "reference temperature" ($T_{ref}$) as the average (or weighted average) temperature experienced by the test specimens.
6. Establish the "first" and the "second" apparent activation energy values for the concrete mix. The "first" and "second" values should adequately bracket the highest and lowest potential apparent activation energy values for the concrete mix in question. Several different methods can be used to establish these values. For instance, the values can be chosen based on default values consistent with historical data (e.g. "first" value=54 kJ/mol; "second" value=29 kJ/mol). These default values can be established based on prediction bands and confidence levels using historical data. Alternatively, the "first" and "second" apparent activation energy values can be selected based on actual measurements of the activation energies for each of the cementitious and pozzolanic components of the concrete mix (e.g. portland cement, fly ash, blast furnace slag, etc.), then taking the highest value and the lowest value respectively as the "first" and "second" apparent activation energy values for the mix. This can be taken a step further in that the activation energies can also be determined for each of the possible blends of the cementitious and pozzolanic components comprising the mix, with these activation energies being added to the list from which the highest (i.e. "first") and lowest (i.e. "second") values are selected.
7. Retroactively calculate the maturity (using the Arrhenius equation) for each of the instrumented specimens by using the "first" apparent activation energy value (as established in Step 6 above) whenever the internal concrete temperature was below the reference temperature and using the "second" apparent activation energy value (as established in Step 6 above) whenever the internal concrete temperature was above the reference temperature. Alternatively, if the specimens were cured throughout the testing period at a nearly constant temperature, simply use the actual age of the specimens (i.e. age when destructively tested for strength) as the equivalent age (and, thus, as the maturity).
8. Tabulate and graph the strength-maturity relationship data as equivalent-age maturity (as calculated by the Arrhenius equation for each test age or as actual age) versus strength (where the maturity for each time interval is the average of the equivalent age maturity for the specimens instrumented with temperature probes or the actual ages of the tested specimens at each test age; and strength is the average strength of the specimens destructively tested for strength at each test age). FIG. 14 provides an example strength-maturity relationship curve using this protocol.
9. For all future maturity calculations for that concrete mix design (until a new strength-maturity relationship curve is determined) calculate equivalent age maturity using the "first" apparent activation energy (as established in Step 6) whenever the internal concrete temperature is below the reference temperature and using the "second" apparent activation energy (as established in Step 6) whenever the internal concrete temperature is above the reference temperature. This will ensure conservatism in all maturity calculations irrespective of the "true" apparent activation energy for the mix and irrespective of the internal curing temperatures of the concrete.

Figure 15:
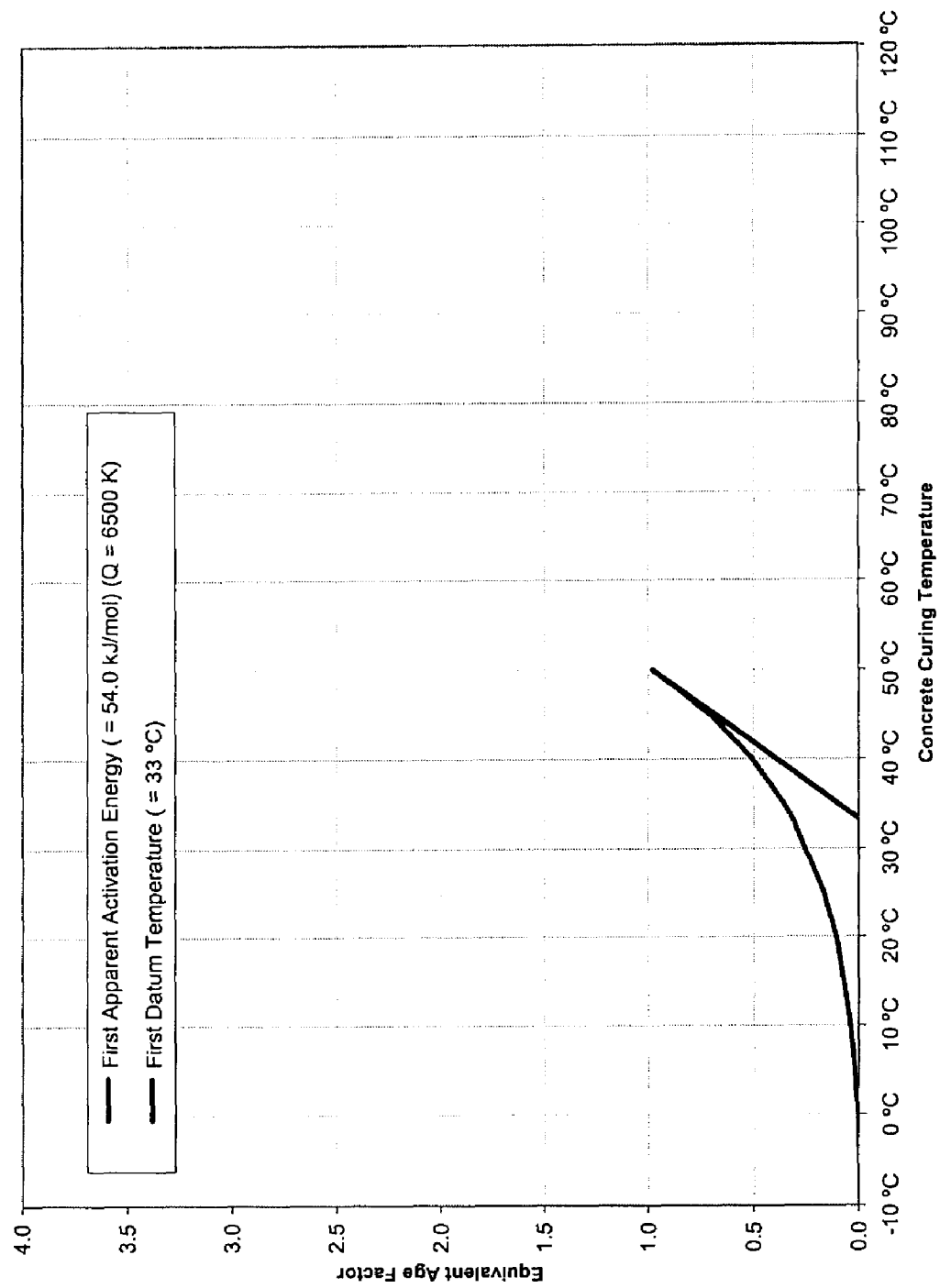
FIG. 15—Shows the graphical determination of the First Datum Temperature for the Improved Nurse-Saul method (using a reference temperature of 50° C.).
Figure 16:
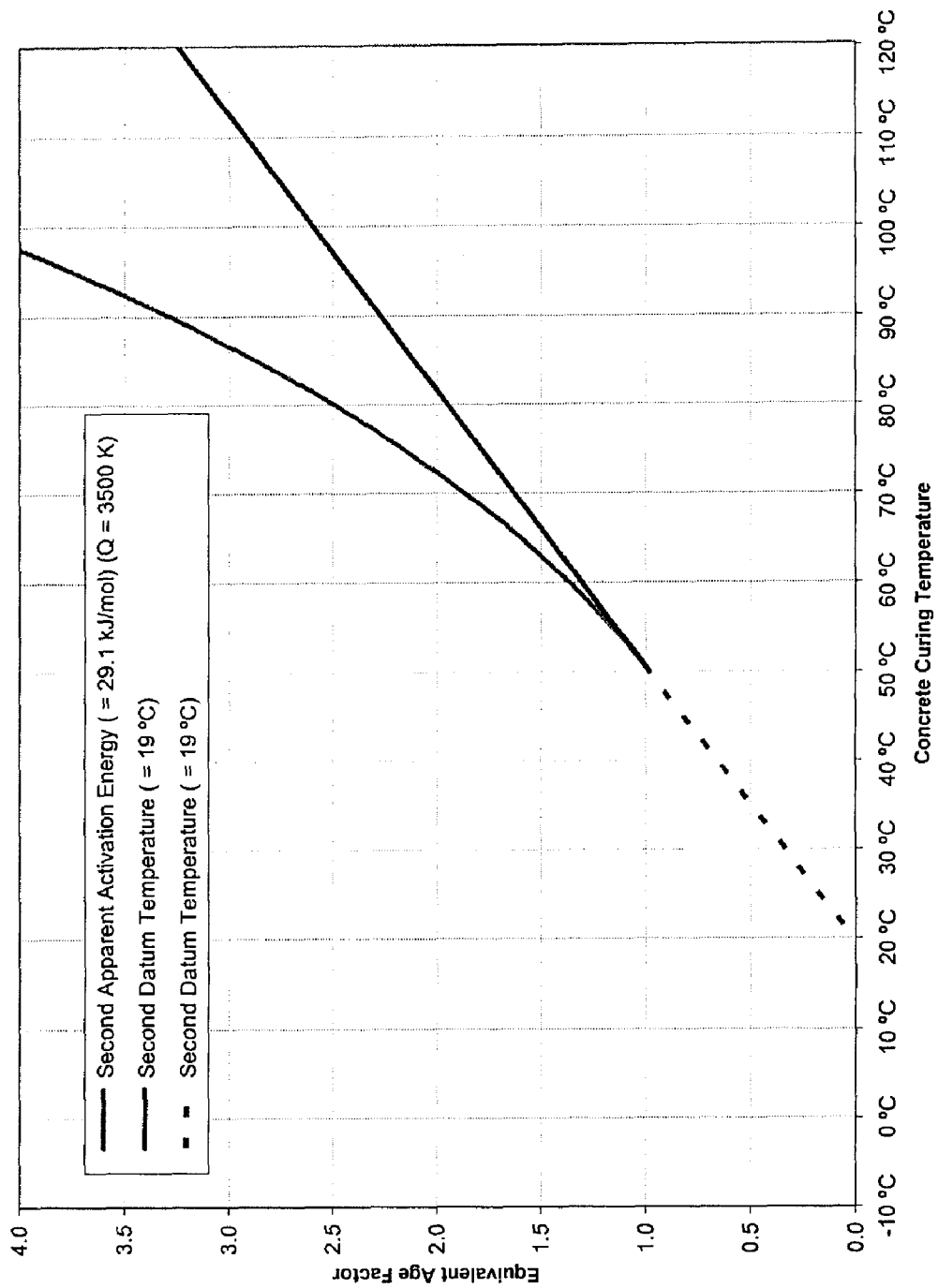
FIG. 16—Shows the graphical determination of the Second Datum Temperature for the Improved Nurse-Saul method (using a reference temperature of 50° C.).
Figure 17:
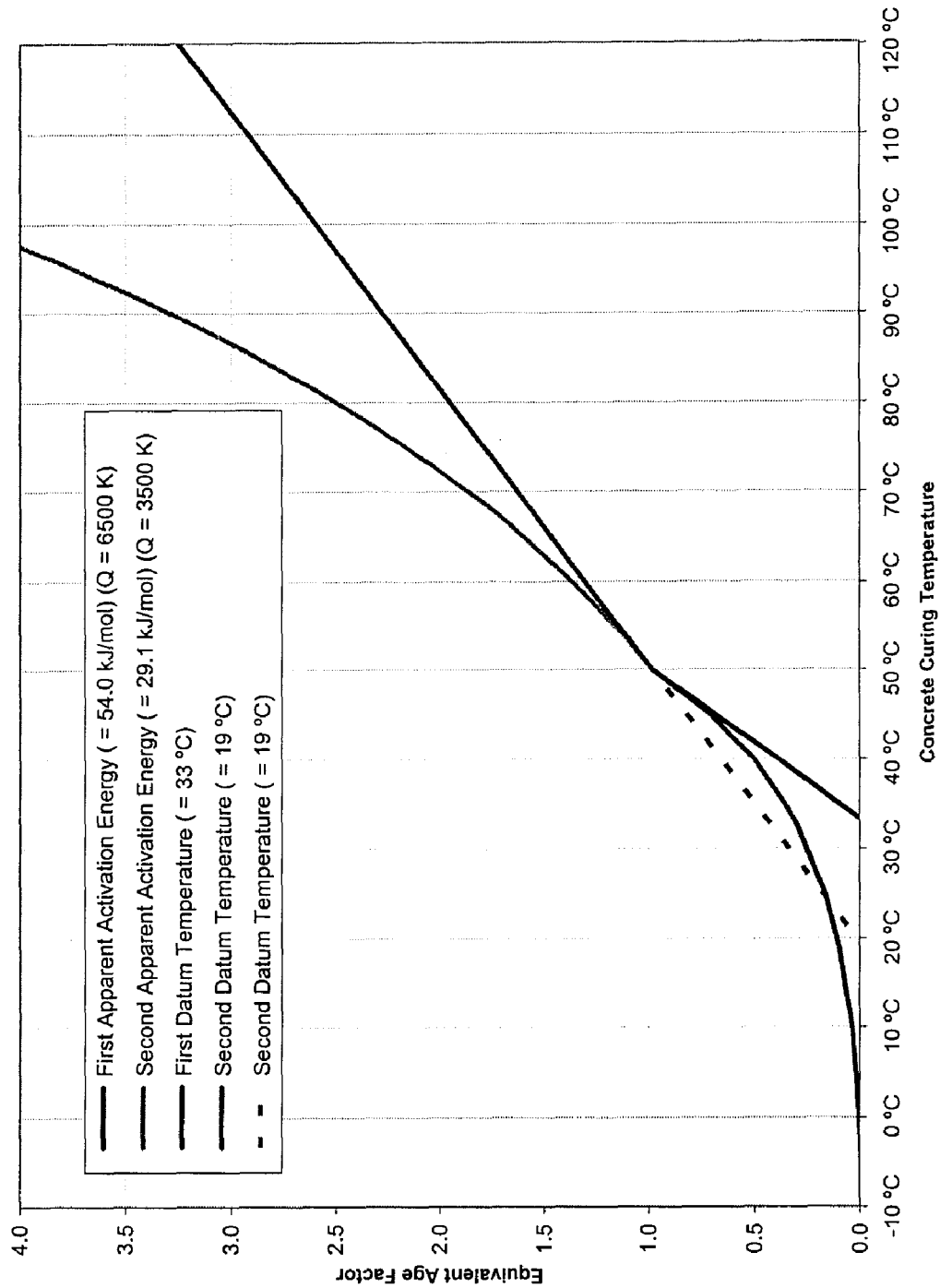
FIG. 17—Shows the graphical determination of both the First and Second Datum Temperatures for the Improved Nurse-Saul method (using a reference temperature of 50° C.).
Figure 18:
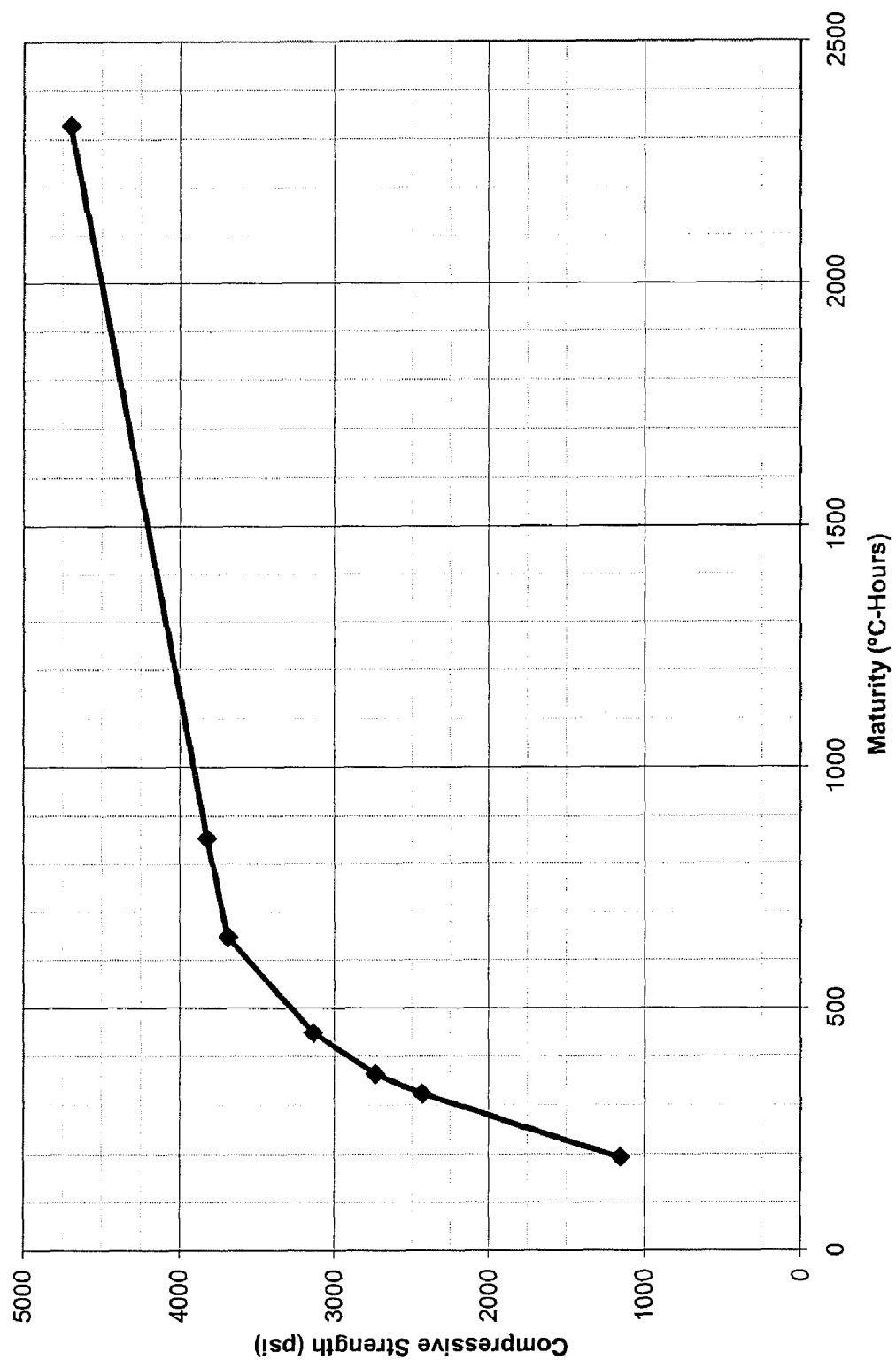
FIG. 18—Shows an example strength-maturity relationship curve based on Nurse-Saul maturity calculations (i.e. maturity is expressed as temperature-time factor, or TTF).

The following is an example of the Improved Nurse-Saul protocol:

1. Complete Steps 1-6 as detailed in the Improved Arrhenius protocol.
2. Determine the "first" and "second" datum temperatures corresponding to the "first" and "second" apparent activation energy values (as established in Step 6 of the Improved Arrhenius protocol) as follows:
    a. Plot the line of Arrhenius EAF values on a graph using the "first" apparent activation energy value (with temperature, in ° C., on the x-axis and EAF on the y-axis) from a low temperature value (e.g. −10° C.) up through the reference temperature. (At the reference temperature, EAF will, of course, equal one.)
    b. Draw a line tangential to the "first" apparent activation energy value's EAF line and extending down until it intersects the x-axis. The point of intersection with the x-axis is the "first" datum temperature. (An example of Steps a and b is shown in FIG. 15.)
    c. Plot the line of Arrhenius EAF values on a graph using the "second" apparent activation energy value (with temperature, in ° C., on the x-axis and EAF on the y-axis) from the reference temperature up through a relatively high temperature value (e.g. 120° C.). (At the reference temperature, EAF will, of course, equal one.)
    d. Draw a line tangential to the "second" apparent activation energy value's EAF line and extending down until it intersects the x-axis. The point of intersection with the x-axis is the "second" datum temperature. (An example of Steps c and d is shown in FIG. 16. An example of the combined results of Steps a, b, c and d is shown in FIG. 17.)
3. Retroactively calculate the maturity (using the Nurse-Saul equation) for each of the instrumented specimens by using the "first" datum temperature (as established in Step 2b) whenever the internal concrete temperature was below the reference temperature and using the "second" datum temperature (as established in Step 2d) whenever the internal concrete temperature was above the reference temperature.
4. Tabulate and graph the strength-maturity relationship data as temperature-time-factor (TTF) maturity (as calculated by the Nurse-Saul equation for each test age) versus strength (where the maturity for each time interval is the average of the TTF maturity for the specimens instrumented with temperature probes at each test age; and strength is the average strength of the specimens destructively tested for strength at each test age). FIG. 18 provides an example strength-maturity curve using this protocol.
5. For all future maturity calculations for that concrete mix design (until a new strength-maturity relationship curve is determined) calculate Nurse-Saul maturity (i.e. TTF) using the "first" datum temperature (as established in Step 2b) whenever the internal concrete temperature is below the reference temperature and using the "second" datum temperature (as established in Step 2d) whenever the internal concrete temperature is above the reference temperature. This will ensure conservatism in all maturity calculations irrespective of the "true" apparent activation energy for the mix and irrespective of the internal curing temperatures of the concrete.

The "first" and "second" datum temperatures determined by the above Improved Nurse-Saul protocol have no theoretical relationship to the "datum temperature" as described in ASTM C1074. As such, the procedures outlined in ASTM C1074 for experimentally determining the theoretical datum temperature for a given concrete mix design should not be used in conjunction with the above protocol.

In addition, Step 2 can be performed computationally rather than graphically to ensure more precise determinations of the "first" and "second" datum temperatures. The "first" and "second" datum temperatures can be calculated from the following equation:

$$T_o = (T_{ref} + 273) - \frac{R}{E_a} \cdot (T_{ref} + 273)^2 - 273$$

where
$T_o$="first" or "second" datum temperature (depending upon whether the apparent activation energy value used in the calculation is the "first" or "second" apparent activation energy) (in ° C.)
$T_{ref}$=reference temperature (in ° C.)
R=universal gas constant (=8.3144 J/(molexK))
$E_a$="first" or "second" apparent activation energy (in J/mole)

Figure 19:
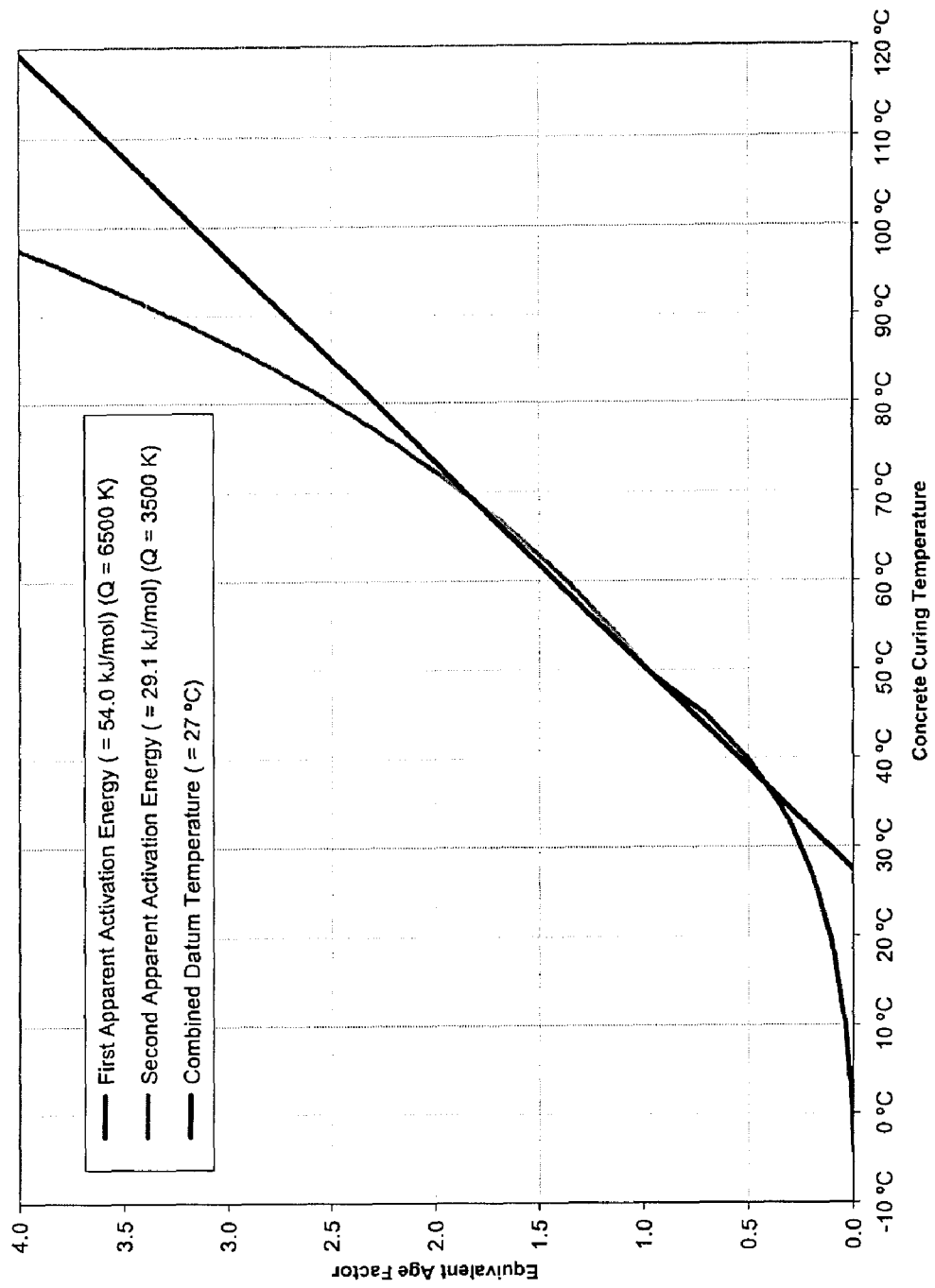
FIG. 19—Shows the graphical determination of the Combined Datum Temperature for the Improved Nurse-Saul method (using a reference temperature of 50° C.).

An alternative to the above Improved Nurse-Saul protocol (hereafter referred to as the First Alternative to the Improved Nurse-Saul protocol) can be used that does not ensure absolute conservatism, but simplifies the end use of the Improved Nurse-Saul method. This alternative example protocol is as follows:

1. Complete Steps 1-6 as detailed in the Improved Arrhenius protocol.
2. Determine the "combined" datum temperature using the "first" and "second" apparent activation energy values (as established in Step 6 of the Arrhenius protocol) using one of the following two alternatives:
    a. Alternative One
        i. Plot the line of Arrhenius EAF values on a graph using the "first" apparent activation energy value (with temperature, in ° C., on the x-axis and EAF on the y-axis) from a low temperature value (e.g. −10° C.) up through the reference temperature. (At the reference temperature, EAF will, of course, equal one.)
        ii. Plot the line of Arrhenius EAF values (on the same graph as Step 2a above) using the "second" apparent activation energy value (with temperature, in ° C., on the x-axis and EAF on the y-axis) from the reference temperature up through a relatively high temperature value (e.g. 130° C.). (At the reference temperature, EAF will, of course, equal one.)
        iii. Draw a line through the point of intersection of the lines plotted in Steps 2a and 2b above (which will be at EAF=1 and $T=T_{ref}$) such that a minimum amount of area lies between the lines plotted in Steps 2a and 2b above and the new line. The point of intersection of the new line with the x-axis is the "combined" datum temperature. (An example of the results of Steps a, b and c is shown in FIG. 19).

b. Alternative Two
   i. Determine the "first" and "second" datum temperatures as detailed in Step 2 of the Improved Nurse-Saul protocol.
   ii. Calculate the "combined" datum temperature as a simple or weighted average of the "first" and "second" datum temperatures. (For example, to calculate a "combined" datum temperature that is two-thirds the way between the "second" and "first" datum temperatures, calculate the "combined" datum temperature as:

$$T_C = \frac{2}{3} \cdot (T_S - T_F) + T_F$$

where
   $T_C$="combined" datum temperature (in ° C.)
   $T_F$="first" datum temperature (in ° C.)
   $T_S$="second" datum temperature (in ° C.)
   )
3. Retroactively calculate the maturity (using the Nurse-Saul equation) for each of the instrumented specimens by using the "combined" datum temperature irrespective of the reference temperature.
4. Complete Step 4 as detailed in the Improved Nurse-Saul protocol.
5. For all future maturity calculations for that concrete mix design (until a new strength-maturity relationship curve is determined) calculate Nurse-Saul maturity (i.e. TTF) using the "combined" datum temperature irrespective of the reference temperature. This will ensure respectable (though not absolute) conservatism in all maturity calculations irrespective of the "true" apparent activation energy for the mix and irrespective of the internal curing temperatures of the concrete.

The Improved Nurse-Saul protocol can be further simplified as follows (this protocol will hereafter be referred to as the Second Alternative to the Improved Nurse-Saul protocol):
1. Complete Steps 1-5 as detailed in the Improved Arrhenius protocol.
2. Determine the "combined" datum temperature using either of the following two alternatives (which are based on Step 2 of the above First Alternative to the Improved Nurse-Saul protocol assuming a "first" apparent activation energy value of 54 kJ/mol and a "second" apparent activation energy value of 29 kJ/mol):

a. Alternative One: Calculate or select the "combined" datum temperature from the following table (using the reference temperature established during Step 5 of the Improved Arrhenius protocol):

| Reference Temperature (° C.) | Combined Datum Temperature (° C.) |
| --- | --- |
| 10 | −8 |
| 20 | 0 |
| 30 | 10 |
| 40 | 18 |
| 50 | 27 |
| 60 | 36 |
| 70 | 44 |
| 80 | 52 |
| 90 | 61 | b. Alternative Two: Calculate the "combined" datum temperature ($T_o$, in ° C.) from the following equation (using the reference temperature, $T_{ref}$, in ° C., established during Step 5 of the Improved Arrhenius protocol):

$T_o$=0.85 times $T_{ref}$−16.5

3. Complete Steps 3-5 as detailed in the First Alternative to the Improved Nurse-Saul protocol.

The unconservative potential of conventional maturity calculations both for Arrhenius and Nurse-Saul methods at various reference temperatures are shown in Tables 7, 9, 11, 13, 15 and 17. By contrast, the conservative nature of the Improved Nurse-Saul, Second Alternative to the Improved Nurse-Saul and Improved Arrhenius protocols described above are presented in Tables 8, 10, 12, 14, 16 and 18. As can be seen, the maturity calculations are always conservative for the Improved Nurse-Saul and Improved Arrhenius methods and, when using the very simple-to-implement Second Alternative to the Improved Nurse-Saul protocol, the EAF values, even when unconservative, are still within 5% of the "true" EAF values.

As can further be seen, the Improved Arrhenius method represents the "best possible" model, by being at all times conservative, yet never too conservative. The Improved Nurse-Saul model, however, remains promising because of the simplicity of the calculations and the ease-of-understanding associated with the Nurse-Saul method in general.

TABLE 7

Unconservative Potential of Conventional Nurse-Saul and Arrhenius Maturity Methods at $T_{ref}$ = 10° C.

| Temperature | | To = −10° C. | | To = 0° C. | | Q = 3500 K | | Q = 5000 K | | Q = 6500 K | |
| --- | --- | --- | --- | --- | --- | --- | --- | --- | --- | --- | --- |
| (° C.) | (° F.) | EAF | % Error | EAF | % Error | EAF | % Error | EAF | % Error | EAF | % Error |
| | | | | | Equivalent Age Errors (if True Q = 3500 K) | | | | | | |
| −10 | 14 | 0.00 | N/A | N/A | N/A | 0.39 | 0.0% | 0.26 | −33.2% | 0.17 | −55.3% |
| −5 | 23 | 0.25 | −50.0% | N/A | N/A | 0.50 | 0.0% | 0.37 | −25.7% | 0.28 | −44.8% |
| 0 | 32 | 0.50 | −21.3% | 0.00 | N/A | 0.64 | 0.0% | 0.52 | −17.6% | 0.43 | −32.2% |
| 5 | 41 | 0.75 | −6.3% | 0.50 | −37.5% | 0.80 | 0.0% | 0.73 | −9.1% | 0.66 | −17.4% |
| 10 | 50 | 1.00 | 0.0% | 1.00 | 0.0% | 1.00 | 0.0% | 1.00 | 0.0% | 1.00 | 0.0% |
| 15 | 59 | 1.25 | 0.8% | 1.50 | 21.0% | 1.24 | 0.0% | 1.36 | 9.6% | 1.49 | 20.2% |
| 20 | 68 | 1.50 | −1.6% | 2.00 | 31.1% | 1.53 | 0.0% | 1.83 | 19.8% | 2.19 | 43.6% |
| 25 | 77 | 1.75 | −6.1% | 2.50 | 34.1% | 1.86 | 0.0% | 2.43 | 30.6% | 3.18 | 70.5% |
| 30 | 86 | 2.00 | −11.6% | 3.00 | 32.6% | 2.26 | 0.0% | 3.21 | 41.9% | 4.55 | 101.3% |
| 35 | 95 | 2.25 | −17.5% | 3.50 | 28.3% | 2.73 | 0.0% | 4.20 | 53.8% | 6.45 | 136.4% |
| 40 | 104 | 2.50 | −23.6% | 4.00 | 22.3% | 3.27 | 0.0% | 5.44 | 66.2% | 9.04 | 176.2% |

TABLE 7-continued

Unconservative Potential of Conventional Nurse-Saul and Arrhenius Maturity Methods at $T_{ref} = 10°$ C.

| Temperature | | To = −10° C. | | To = 0° C. | | Q = 3500 K | | Q = 5000 K | | Q = 6500 K | |
|---|---|---|---|---|---|---|---|---|---|---|---|
| (° C.) | (° F.) | EAF | % Error | EAF | % Error | EAF | % Error | EAF | % Error | EAF | % Error |
| 45 | 113 | 2.75 | −29.5% | 4.50 | 15.4% | 3.90 | 0.0% | 6.99 | 79.2% | 12.53 | 221.2% |
| 50 | 122 | 3.00 | −35.1% | 5.00 | 8.1% | 4.63 | 0.0% | 8.92 | 92.8% | 17.19 | 271.6% |
| 55 | 131 | 3.25 | −40.4% | 5.50 | 0.8% | 5.46 | 0.0% | 11.29 | 106.9% | 23.36 | 328.2% |
| 60 | 140 | 3.50 | −45.3% | 6.00 | −6.3% | 6.40 | 0.0% | 14.19 | 121.6% | 31.46 | 391.2% |
| 65 | 149 | 3.75 | −49.9% | 6.50 | −13.1% | 7.48 | 0.0% | 17.72 | 136.9% | 41.99 | 461.2% |
| 70 | 158 | 4.00 | −54.0% | 7.00 | −19.5% | 8.70 | 0.0% | 21.99 | 152.7% | 55.58 | 538.8% |
| 80 | 176 | 4.50 | −61.3% | 8.00 | −31.1% | 11.62 | 0.0% | 33.23 | 186.1% | 95.07 | 718.4% |
| 90 | 194 | 5.00 | −67.2% | 9.00 | −41.0% | 15.27 | 0.0% | 49.09 | 221.6% | 157.88 | 934.2% |
| 100 | 212 | 5.50 | −72.2% | 10.00 | −49.4% | 19.77 | 0.0% | 71.02 | 259.3% | 255.17 | 1190.8% |
| 110 | 230 | 6.00 | −76.2% | 11.00 | −56.4% | 25.26 | 0.0% | 100.79 | 299.0% | 402.19 | 1492.4% |
| 120 | 248 | 6.50 | −79.6% | 12.00 | −62.3% | 31.87 | 0.0% | 140.50 | 340.9% | 619.40 | 1843.6% |
| 130 | 266 | 7.00 | −82.4% | 13.00 | −67.3% | 39.75 | 0.0% | 192.65 | 384.7% | 933.71 | 2248.9% |
| Equivalent Age Errors (if True Q = 6500 K) | | | | | | | | | | | |
| −10 | 14 | 0.00 | N/A | N/A | N/A | 0.39 | 123.9% | 0.26 | 49.6% | 0.17 | 0.0% |
| −5 | 23 | 0.25 | −9.6% | N/A | N/A | 0.50 | 81.0% | 0.37 | 34.5% | 0.28 | 0.0% |
| 0 | 32 | 0.50 | 16.0% | 0.00 | N/A | 0.64 | 47.4% | 0.52 | 21.4% | 0.43 | 0.0% |
| 5 | 41 | 0.75 | 13.4% | 0.50 | −24.4% | 0.80 | 21.0% | 0.73 | 10.0% | 0.66 | 0.0% |
| 10 | 50 | 1.00 | 0.0% | 1.00 | 0.0% | 1.00 | 0.0% | 1.00 | 0.0% | 1.00 | 0.0% |
| 15 | 59 | 1.25 | −16.1% | 1.50 | 0.7% | 1.24 | −16.8% | 1.36 | −8.8% | 1.49 | 0.0% |
| 20 | 68 | 1.50 | −31.5% | 2.00 | −8.7% | 1.53 | −30.4% | 1.83 | −16.5% | 2.19 | 0.0% |
| 25 | 77 | 1.75 | −44.9% | 2.50 | −21.3% | 1.86 | −41.4% | 2.43 | −23.4% | 3.18 | 0.0% |
| 30 | 86 | 2.00 | −56.1% | 3.00 | −34.1% | 2.26 | −50.3% | 3.21 | −29.5% | 4.55 | 0.0% |
| 35 | 95 | 2.25 | −65.1% | 3.50 | −45.7% | 2.73 | −57.7% | 4.20 | −35.0% | 6.45 | 0.0% |
| 40 | 104 | 2.50 | −72.3% | 4.00 | −55.7% | 3.27 | −63.8% | 5.44 | −39.8% | 9.04 | 0.0% |
| 45 | 113 | 2.75 | −78.0% | 4.50 | −64.1% | 3.90 | −68.9% | 6.99 | −44.2% | 12.53 | 0.0% |
| 50 | 122 | 3.00 | −82.5% | 5.00 | −70.9% | 4.63 | −73.1% | 8.92 | −48.1% | 17.19 | 0.0% |
| 55 | 131 | 3.25 | −86.1% | 5.50 | −76.5% | 5.46 | −76.6% | 11.29 | −51.7% | 23.36 | 0.0% |
| 60 | 140 | 3.50 | −88.9% | 6.00 | −80.9% | 6.40 | −79.6% | 14.19 | −54.9% | 31.46 | 0.0% |
| 65 | 149 | 3.75 | −91.1% | 6.50 | −84.5% | 7.48 | −82.2% | 17.72 | −57.8% | 41.99 | 0.0% |
| 70 | 158 | 4.00 | −92.8% | 7.00 | −87.4% | 8.70 | −84.3% | 21.99 | −60.4% | 55.58 | 0.0% |
| 80 | 176 | 4.50 | −95.3% | 8.00 | −91.6% | 11.62 | −87.8% | 33.23 | −65.0% | 95.07 | 0.0% |
| 90 | 194 | 5.00 | −96.8% | 9.00 | −94.3% | 15.27 | −90.3% | 49.09 | −68.9% | 157.88 | 0.0% |
| 100 | 212 | 5.50 | −97.8% | 10.00 | −96.1% | 19.77 | −92.3% | 71.02 | −72.2% | 255.17 | 0.0% |
| 110 | 230 | 6.00 | −98.5% | 11.00 | −97.3% | 25.26 | −93.7% | 100.79 | −74.9% | 402.19 | 0.0% |
| 120 | 248 | 6.50 | −99.0% | 12.00 | −98.1% | 31.87 | −94.9% | 140.50 | −77.3% | 619.40 | 0.0% |
| 130 | 266 | 7.00 | −99.3% | 13.00 | −98.6% | 39.75 | −95.7% | 192.65 | −79.4% | 933.71 | 0.0% |

TABLE 8

Conservative Nature of Improved Nurse-Saul (and First Alternative) and Improved Arrhenius Maturity Methods at $T_{ref} = 10°$ C.

| Temperature | | Equivalent Age Errors (if True Q = 3500 K) | | | | | |
|---|---|---|---|---|---|---|---|
| | | Improved Nurse-Saul | | Improved Nurse-Saul (Second Alternative) (To = −8.0 C.) | | Improved Arrhenius | |
| (° C.) | (° F.) | EAF | % Error | EAF | % Error | EAF | % Error |
| −10 | 14 | N/A | N/A | N/A | N/A | 0.17 | −55.3% |
| −5 | 23 | N/A | N/A | 0.17 | −66.7% | 0.28 | −44.8% |
| 0 | 32 | 0.19 | −70.4% | 0.44 | −30.1% | 0.43 | −32.2% |
| 5 | 41 | 0.59 | −25.8% | 0.72 | −9.8% | 0.66 | −17.4% |
| 10 | 50 | 1.00 | 0.0% | 1.00 | 0.0% | 1.00 | 0.0% |
| 15 | 59 | 1.22 | −1.7% | 1.28 | 3.1% | 1.24 | 0.0% |
| 20 | 60 | 1.44 | −5.8% | 1.56 | 2.0% | 1.50 | 0.0% |
| 25 | 77 | 1.66 | −11.2% | 1.83 | −1.6% | 1.86 | 0.0% |
| 30 | 86 | 1.87 | −17.2% | 2.11 | −6.7% | 2.26 | 0.0% |
| 35 | 95 | 2.09 | −23.3% | 2.39 | −12.5% | 2.73 | 0.0% |
| 40 | 104 | 2.31 | −29.4% | 2.67 | −18.5% | 3.27 | 0.0% |
| 45 | 113 | 2.53 | −35.2% | 2.94 | −24.5% | 3.90 | 0.0% |
| 50 | 122 | 2.75 | −40.6% | 3.22 | −30.3% | 4.63 | 0.0% |
| 55 | 131 | 2.97 | −45.6% | 3.50 | −35.9% | 5.46 | 0.0% |
| 60 | 140 | 3.19 | −50.3% | 3.78 | −41.0% | 6.40 | 0.0% |
| 65 | 149 | 3.40 | −54.5% | 4.06 | −45.8% | 7.48 | 0.0% |
| 70 | 158 | 3.62 | −58.4% | 4.33 | −50.2% | 8.70 | 0.0% |
| 80 | 176 | 4.06 | −65.1% | 4.89 | −57.9% | 11.62 | 0.0% |
| 90 | 194 | 4.50 | −70.5% | 5.44 | −64.3% | 15.27 | 0.0% |
| 100 | 212 | 4.93 | −75.0% | 6.00 | −69.6% | 19.77 | 0.0% |
| 110 | 230 | 5.37 | −78.7% | 6.56 | −74.0% | 25.26 | 0.0% |
| 120 | 248 | 5.81 | −81.8% | 7.11 | −77.7% | 31.87 | 0.0% |
| 130 | 266 | 6.24 | −84.3% | 7.67 | −80.7% | 39.75 | 0.0% |
| Equivalent Age Errors (if True Q = 6500 K) | | | | | | | |
| | | Improved Nurse-Saul | | Improved Nurse-Saul (Second Alternative) (To = −8.0 C.) | | Arrhenius | |
| (° C.) | (° F.) | EAF | % Error | EAF | % Error | EAF | % Error |
| −10 | 14 | N/A | N/A | N/A | N/A | 0.17 | 0.0% |
| −5 | 23 | N/A | N/A | 0.17 | −66.7% | 0.28 | 0.0% |
| 0 | 32 | 0.19 | −70.4% | 0.44 | −30.1% | 0.43 | 0.0% |
| 5 | 41 | 0.59 | −25.8% | 0.72 | −9.8% | 0.66 | 0.0% |
| 10 | 50 | 1.00 | 0.0% | 1.00 | 0.0% | 1.00 | 0.0% |
| 15 | 59 | 1.22 | −1.7% | 1.28 | 3.1% | 1.24 | −16.8% |
| 20 | 68 | 1.44 | −5.8% | 1.56 | 2.0% | 1.53 | −30.4% |
| 25 | 77 | 1.66 | −11.2% | 1.83 | −1.6% | 1.86 | −41.4% |

TABLE 8-continued

Conservative Nature of Improved Nurse-Saul (and First Alternative) and Improved Arrhenius Maturity Methods at $T_{ref} = 10°$ C.

| | | | | | | | |
|---|---|---|---|---|---|---|---|
| 30 | 86 | 1.87 | −17.2% | 2.11 | −6.7% | 2.26 | −50.3% |
| 35 | 95 | 2.09 | −23.3% | 2.39 | −12.5% | 2.73 | −57.7% |
| 40 | 104 | 2.31 | −29.4% | 2.67 | −18.5% | 3.27 | −63.8% |
| 45 | 113 | 2.53 | −35.2% | 2.94 | −24.5% | 3.90 | −68.9% |
| 50 | 122 | 2.75 | −40.6% | 3.22 | −30.3% | 4.63 | −73.1% |
| 55 | 131 | 2.97 | −45.6% | 3.50 | −35.9% | 5.46 | −76.6% |
| 60 | 140 | 3.19 | −50.3% | 3.78 | −41.0% | 6.40 | −79.6% |
| 65 | 149 | 3.40 | −54.5% | 4.06 | −45.8% | 7.48 | −82.2% |
| 70 | 158 | 3.62 | −58.4% | 4.33 | −50.2% | 8.70 | −84.3% |
| 80 | 176 | 4.06 | −65.1% | 4.89 | −57.9% | 11.62 | −87.8% |
| 90 | 194 | 4.50 | −70.5% | 5.44 | −64.3% | 15.27 | −90.3% |
| 100 | 212 | 4.93 | −75.0% | 6.00 | −69.6% | 19.77 | −92.3% |
| 110 | 230 | 5.37 | −78.7% | 6.56 | −74.0% | 25.26 | −93.7% |
| 120 | 248 | 5.81 | −81.8% | 7.11 | −77.7% | 31.87 | −94.9% |
| 130 | 266 | 6.24 | −84.3% | 7.67 | −80.7% | 39.75 | −95.7% |

TABLE 9

Unconservative Potential of Conventional Nurse-Saul and Arrhenius Maturity Methods at $T_{ref} = 20°$ C.

| Temperature | | To = −10° C. | | To = 0° C. | | Q = 3500 K | | Q = 5000 K | | Q = 6500 K | |
|---|---|---|---|---|---|---|---|---|---|---|---|
| (° C.) | (° F.) | EAF | % Error | EAF | % Error | EAF | % Error | EAF | % Error | EAF | % Error |
| Equivalent Age Errors (if True Q = 3500 K) | | | | | | | | | | | |
| −10 | 14 | 0.00 | N/A | N/A | N/A | 0.26 | 0.0% | 0.14 | −44.2% | 0.08 | −68.9% |
| −5 | 23 | 0.17 | −49.2% | N/A | N/A | 0.33 | 0.0% | 0.20 | −38.0% | 0.13 | −61.5% |
| 0 | 32 | 0.33 | −20.0% | 0.00 | N/A | 0.42 | 0.0% | 0.29 | −31.3% | 0.20 | −52.8% |
| 5 | 41 | 0.50 | −4.7% | 0.25 | −52.4% | 0.52 | 0.0% | 0.40 | −24.1% | 0.30 | −42.4% |
| 10 | 50 | 0.67 | 1.7% | 0.50 | −23.7% | 0.66 | 0.0% | 0.55 | −16.5% | 0.46 | −30.4% |
| 15 | 59 | 0.83 | 2.5% | 0.75 | −7.7% | 0.81 | 0.0% | 0.74 | −8.5% | 0.68 | −16.3% |
| 20 | 68 | 1.00 | 0.0% | 1.00 | 0.0% | 1.00 | 0.0% | 1.00 | 0.0% | 1.00 | 0.0% |
| 25 | 77 | 1.17 | −4.5% | 1.25 | 2.3% | 1.22 | 0.0% | 1.33 | 9.0% | 1.45 | 18.7% |
| 30 | 86 | 1.33 | −10.1% | 1.50 | 1.1% | 1.48 | 0.0% | 1.76 | 18.4% | 2.08 | 40.2% |
| 35 | 95 | 1.50 | −16.2% | 1.75 | −2.2% | 1.79 | 0.0% | 2.30 | 28.3% | 2.95 | 64.6% |
| 40 | 104 | 1.67 | −22.3% | 2.00 | −6.8% | 2.15 | 0.0% | 2.98 | 38.7% | 4.13 | 92.4% |
| 45 | 113 | 1.83 | −28.3% | 2.25 | −12.0% | 2.56 | 0.0% | 3.83 | 49.6% | 5.72 | 123.7% |
| 50 | 122 | 2.00 | −34.1% | 2.50 | −17.6% | 3.03 | 0.0% | 4.88 | 60.9% | 7.85 | 158.8% |
| 55 | 131 | 2.17 | −39.4% | 2.75 | −23.1% | 3.58 | 0.0% | 6.18 | 72.7% | 10.67 | 198.2% |
| 60 | 140 | 2.33 | −44.4% | 3.00 | −28.6% | 4.20 | 0.0% | 7.77 | 85.0% | 14.36 | 242.1% |
| 65 | 149 | 2.50 | −49.0% | 3.25 | −33.7% | 4.91 | 0.0% | 9.70 | 97.7% | 19.17 | 290.9% |
| 70 | 158 | 2.67 | −53.3% | 3.50 | −38.6% | 5.70 | 0.0% | 12.03 | 110.9% | 25.38 | 344.8% |
| 80 | 176 | 3.00 | −60.6% | 4.00 | −47.5% | 7.62 | 0.0% | 18.18 | 138.7% | 43.41 | 469.9% |
| 90 | 194 | 3.33 | −66.7% | 4.50 | −55.0% | 10.01 | 0.0% | 26.86 | 168.4% | 72.09 | 620.3% |
| 100 | 212 | 3.67 | −71.7% | 5.00 | −61.4% | 12.96 | 0.0% | 38.86 | 199.8% | 116.52 | 798.9% |
| 110 | 230 | 4.00 | −75.8% | 5.50 | −66.8% | 16.56 | 0.0% | 55.15 | 233.0% | 183.65 | 1009.0% |
| 120 | 248 | 4.33 | −79.3% | 6.00 | −71.3% | 20.90 | 0.0% | 76.88 | 267.9% | 282.83 | 1253.6% |
| 130 | 266 | 4.67 | −82.1% | 6.50 | −75.1% | 26.06 | 0.0% | 105.41 | 304.5% | 426.35 | 1535.8% |
| Equivalent Age Errors (if True Q = 6500 K) | | | | | | | | | | | |
| −10 | 14 | 0.00 | N/A | N/A | N/A | 0.26 | 221.5% | 0.14 | 79.3% | 0.08 | 0.0% |
| −5 | 23 | 0.17 | 32.0% | N/A | N/A | 0.33 | 159.9% | 0.20 | 61.2% | 0.13 | 0.0% |
| 0 | 32 | 0.33 | 69.3% | 0.00 | N/A | 0.42 | 111.7% | 0.29 | 45.5% | 0.20 | 0.0% |
| 5 | 41 | 0.50 | 65.5% | 0.25 | −17.2% | 0.52 | 73.8% | 0.40 | 31.8% | 0.30 | 0.0% |
| 10 | 50 | 0.67 | 46.0% | 0.50 | 9.5% | 0.66 | 43.6% | 0.55 | 19.8% | 0.46 | 0.0% |
| 15 | 59 | 0.83 | 22.5% | 0.75 | 10.2% | 0.81 | 19.5% | 0.74 | 9.3% | 0.68 | 0.0% |
| 20 | 68 | 1.00 | 0.0% | 1.00 | 0.0% | 1.00 | 0.0% | 1.00 | 0.0% | 1.00 | 0.0% |
| 25 | 77 | 1.17 | −19.6% | 1.25 | −13.8% | 1.22 | −15.8% | 1.33 | −8.2% | 1.45 | 0.0% |
| 30 | 86 | 1.33 | −35.9% | 1.50 | −27.9% | 1.48 | −28.7% | 1.76 | −15.5% | 2.08 | 0.0% |
| 35 | 95 | 1.50 | −49.1% | 1.75 | −40.6% | 1.79 | −39.3% | 2.30 | −22.1% | 2.95 | 0.0% |
| 40 | 104 | 1.67 | −59.6% | 2.00 | −51.5% | 2.15 | −48.0% | 2.98 | −27.9% | 4.13 | 0.0% |
| 45 | 113 | 1.83 | −68.0% | 2.25 | −60.7% | 2.56 | −55.3% | 3.83 | −33.1% | 5.72 | 0.0% |
| 50 | 122 | 2.00 | −74.5% | 2.50 | −68.2% | 3.03 | −61.4% | 4.88 | −37.8% | 7.85 | 0.0% |
| 55 | 131 | 2.17 | −79.7% | 2.75 | −74.2% | 3.58 | −66.5% | 6.18 | −42.1% | 10.67 | 0.0% |
| 60 | 140 | 2.33 | −83.8% | 3.00 | −79.1% | 4.20 | −70.8% | 7.77 | −45.9% | 14.36 | 0.0% |
| 65 | 149 | 2.50 | −87.0% | 3.25 | −83.0% | 4.91 | −74.4% | 9.70 | −49.4% | 19.17 | 0.0% |
| 70 | 158 | 2.67 | −89.5% | 3.50 | −86.2% | 5.70 | −77.5% | 12.03 | −52.6% | 25.38 | 0.0% |
| 80 | 176 | 3.00 | −93.1% | 4.00 | −90.8% | 7.62 | −82.5% | 18.18 | −58.1% | 43.41 | 0.0% |
| 90 | 194 | 3.33 | −95.4% | 4.50 | −93.8% | 10.01 | −86.1% | 26.86 | −62.7% | 72.09 | 0.0% |
| 100 | 212 | 3.67 | −96.9% | 5.00 | −95.7% | 12.96 | −88.9% | 38.86 | −66.6% | 116.52 | 0.0% |
| 110 | 230 | 4.00 | −97.8% | 5.50 | −97.0% | 16.56 | −91.0% | 55.15 | −70.0% | 183.65 | 0.0% |
| 120 | 248 | 4.33 | −98.5% | 6.00 | −97.9% | 20.90 | −92.6% | 76.88 | −72.8% | 282.83 | 0.0% |
| 130 | 266 | 4.67 | −98.9% | 6.50 | −98.5% | 26.06 | −93.9% | 105.41 | −75.3% | 426.35 | 0.0% |

TABLE 10

Conservative Nature of Improved Nurse-Saul (and First Alternative) and Improved Arrhenius Maturity Methods at $T_{ref} = 20°$ C.

| Temperature | | Equivalent Age Errors (if True Q = 3500 K) | | | | | | Equivalent Age Errors (if True Q = 6500 K) | | | | | |
|---|---|---|---|---|---|---|---|---|---|---|---|---|---|
| | | Improved Nurse-Saul | | Improved Nurse-Saul (Second Alternative) (To = 0.5 C.) | | Improved Arrhenius | | Improved Nurse-Saul | | Improved Nurse-Saul (Second Alternative) (To = 0.5 C.) | | Arrhenius | |
| (° C.) | (° F.) | EAF | % Error | EAF | % Error | EAF | % Error | EAF | % Error | EAF | % Error | EAF | % Error |
| −10 | 14 | N/A | N/A | N/A | N/A | 0.08 | −68.9% | N/A | N/A | N/A | N/A | 0.08 | 0.0% |
| −5 | 23 | N/A | N/A | N/A | N/A | 0.13 | −61.5% | N/A | N/A | N/A | N/A | 0.13 | 0.0% |
| 0 | 32 | N/A | N/A | N/A | N/A | 0.20 | −52.8% | N/A | N/A | N/A | N/A | 0.20 | 0.0% |
| 5 | 41 | N/A | N/A | 0.23 | 56.0% | 0.30 | 42.4% | N/A | N/A | 0.23 | −56.0% | 0.30 | 0.0% |
| 10 | 50 | 0.24 | −63.0% | 0.49 | −25.7% | 0.46 | −30.4% | 0.24 | −63.0% | 0.49 | −25.7% | 0.46 | 0.0% |
| 15 | 59 | 0.62 | −23.5% | 0.74 | −8.5% | 0.68 | −16.3% | 0.62 | −23.5% | 0.74 | −8.5% | 0.68 | 0.0% |
| 20 | 68 | 1.00 | 0.0% | 1.00 | 0.0% | 1.00 | 0.0% | 1.00 | 0.0% | 1.00 | 0.0% | 1.00 | 0.0% |
| 25 | 77 | 1.20 | −1.5% | 1.26 | 2.8% | 1.22 | 0.0% | 1.20 | −1.5% | 1.26 | 2.8% | 1.22 | −15.8% |
| 30 | 86 | 1.41 | −5.1% | 1.51 | 2.0% | 1.48 | 0.0% | 1.41 | −5.1% | 1.51 | 2.0% | 1.48 | −28.7% |
| 35 | 95 | 1.61 | −9.9% | 1.77 | −1.1% | 1.79 | 0.0% | 1.61 | −9.9% | 1.77 | −1.1% | 1.79 | −39.3% |
| 40 | 104 | 1.82 | −15.4% | 2.03 | −5.6% | 2.15 | 0.0% | 1.02 | −15.4% | 2.00 | −5.6% | 2.15 | −40.0% |
| 45 | 113 | 2.02 | −21.1% | 2.28 | −10.8% | 2.56 | 0.0% | 2.02 | −21.1% | 2.28 | −10.8% | 2.56 | −55.3% |
| 50 | 122 | 2.22 | −26.7% | 2.54 | −16.3% | 3.03 | 0.0% | 2.22 | −20.7% | 2.54 | −16.3% | 3.03 | −61.4% |
| 55 | 131 | 2.43 | −32.2% | 2.79 | −21.9% | 3.58 | 0.0% | 2.43 | −32.2% | 2.79 | −21.9% | 3.58 | −66.5% |
| 60 | 140 | 2.63 | −37.3% | 3.05 | −27.3% | 4.20 | 0.0% | 2.63 | −37.3% | 3.05 | −27.3% | 4.20 | −70.8% |
| 65 | 149 | 2.83 | −42.2% | 3.31 | −32.6% | 4.91 | 0.0% | 2.83 | −42.2% | 3.31 | −32.6% | 4.91 | −74.4% |
| 70 | 158 | 3.04 | −46.7% | 3.56 | −37.5% | 5.70 | 0.0% | 3.04 | −46.7% | 3.56 | −37.5% | 5.70 | −77.5% |
| 80 | 176 | 3.45 | −54.8% | 4.08 | −46.5% | 7.62 | 0.0% | 3.45 | −54.8% | 4.08 | −46.5% | 7.62 | −82.5% |
| 90 | 194 | 0.05 | −61.5% | 4.59 | −54.1% | 10.01 | 0.0% | 3.85 | −61.5% | 4.59 | −54.1% | 10.01 | −86.1% |
| 100 | 212 | 4.26 | −67.1% | 5.10 | −60.6% | 12.96 | 0.0% | 4.26 | −67.1% | 5.10 | −60.6% | 12.96 | −88.9% |
| 110 | 230 | 4.67 | −71.8% | 5.62 | −66.1% | 16.56 | 0.0% | 4.67 | −71.8% | 5.62 | −66.1% | 16.56 | −91.0% |
| 120 | 248 | 5.08 | −75.7% | 6.13 | −70.7% | 20.90 | 0.0% | 5.08 | −75.7% | 6.13 | −70.7% | 20.90 | −92.6% |
| 130 | 266 | 5.48 | −79.0% | 6.64 | −74.5% | 26.06 | 0.0% | 5.48 | −79.0% | 6.64 | −74.5% | 26.06 | −93.9% |

TABLE 11

Unconservative Potential of Conventional Nurse-Saul and Arrhenius Maturity Methods at $T_{ref} = 30°$ C.

| Temperature | | To = −10° C. | | To = 0° C. | | Q = 3500 K | | Q = 5000 K | | Q = 6500 K | |
|---|---|---|---|---|---|---|---|---|---|---|---|
| (° C.) | (° F.) | EAF | % Error | EAF | % Error | EAF | % Error | EAF | % Error | EAF | % Error |
| | | | | | | Equivalent Age Errors (if True Q = 3500 K) | | | | | |
| −10 | 14 | 0.00 | N/A | N/A | N/A | 0.17 | 0.0% | 0.08 | −52.9% | 0.04 | −77.8% |
| −5 | 23 | 0.13 | −43.5% | N/A | N/A | 0.22 | 0.0% | 0.12 | −47.6% | 0.06 | −72.6% |
| 0 | 32 | 0.25 | −11.0% | 0.00 | N/A | 0.28 | 0.0% | 0.16 | −42.0% | 0.09 | −66.3% |
| 5 | 41 | 0.38 | 6.0% | 0.17 | −52.9% | 0.35 | 0.0% | 0.23 | −35.9% | 0.15 | −58.9% |
| 10 | 50 | 0.50 | 13.1% | 0.33 | −24.6% | 0.44 | 0.0% | 0.31 | −29.5% | 0.22 | −50.3% |
| 15 | 59 | 0.63 | 14.1% | 0.50 | −8.7% | 0.55 | 0.0% | 0.42 | −22.7% | 0.33 | −40.3% |
| 20 | 68 | 0.75 | 11.2% | 0.67 | −1.1% | 0.67 | 0.0% | 0.57 | −15.5% | 0.48 | −28.7% |
| 25 | 77 | 0.88 | 6.2% | 0.83 | 1.2% | 0.82 | 0.0% | 0.76 | −8.0% | 0.70 | −15.3% |
| 30 | 86 | 1.00 | 0.0% | 1.00 | 0.0% | 1.00 | 0.0% | 1.00 | 0.0% | 1.00 | 0.0% |
| 35 | 95 | 1.13 | −6.7% | 1.17 | −3.3% | 1.21 | 0.0% | 1.31 | 8.4% | 1.42 | 17.4% |
| 40 | 104 | 1.25 | −13.6% | 1.33 | −7.8% | 1.45 | 0.0% | 1.69 | 17.1% | 1.98 | 37.2% |
| 45 | 113 | 1.38 | −20.3% | 1.50 | −13.0% | 1.72 | 0.0% | 2.18 | 26.3% | 2.75 | 59.5% |
| 50 | 122 | 1.50 | −26.6% | 1.67 | −18.5% | 2.04 | 0.0% | 2.78 | 35.9% | 3.77 | 84.6% |
| 55 | 131 | 1.63 | −32.6% | 1.83 | −24.0% | 2.41 | 0.0% | 3.52 | 45.8% | 5.13 | 112.7% |
| 60 | 140 | 1.75 | −38.2% | 2.00 | −29.4% | 2.83 | 0.0% | 4.42 | 56.2% | 6.91 | 144.0% |
| 65 | 149 | 1.88 | −43.3% | 2.17 | −34.5% | 3.31 | 0.0% | 5.52 | 67.0% | 9.22 | 178.8% |
| 70 | 158 | 2.00 | −48.0% | 2.33 | −39.3% | 3.85 | 0.0% | 6.85 | 78.1% | 12.20 | 217.3% |
| 80 | 176 | 2.25 | −56.2% | 2.67 | −48.1% | 5.14 | 0.0% | 10.35 | 101.6% | 20.87 | 306.5% |
| 90 | 194 | 2.50 | −63.0% | 3.00 | −55.5% | 6.75 | 0.0% | 15.30 | 126.7% | 34.67 | 413.7% |
| 100 | 212 | 2.75 | −68.5% | 3.33 | −61.9% | 8.74 | 0.0% | 22.13 | 153.2% | 56.03 | 541.2% |
| 110 | 230 | 3.00 | −73.1% | 3.67 | −67.2% | 11.16 | 0.0% | 31.40 | 181.2% | 88.31 | 691.0% |
| 120 | 248 | 3.25 | −76.9% | 4.00 | −71.6% | 14.09 | 0.0% | 43.77 | 210.7% | 136.01 | 865.4% |
| 130 | 266 | 3.50 | −80.1% | 4.33 | −75.3% | 17.57 | 0.0% | 60.02 | 241.6% | 205.02 | 1066.8% |

TABLE 11-continued

Unconservative Potential of Conventional Nurse-Saul and Arrhenius Maturity Methods at $T_{ref} = 30°$ C.

| Temperature | | To = −10° C. | | To = 0° C. | | Q = 3500 K | | Q = 5000 K | | Q = 6500 K | |
|---|---|---|---|---|---|---|---|---|---|---|---|
| (° C.) | (° F.) | EAF | % Error | EAF | % Error | EAF | % Error | EAF | % Error | EAF | % Error |
| | | | | | Equivalent Age Errors (if True Q = 6500 K) | | | | | | |
| −10 | 14 | 0.00 | N/A | N/A | N/A | 0.17 | 350.8% | 0.08 | 112.3% | 0.04 | 0.0% |
| −5 | 23 | 0.13 | 105.9% | N/A | N/A | 0.22 | 264.4% | 0.12 | 90.9% | 0.06 | 0.0% |
| 0 | 32 | 0.25 | 164.1% | 0.00 | N/A | 0.28 | 196.8% | 0.16 | 72.3% | 0.09 | 0.0% |
| 5 | 41 | 0.38 | 158.1% | 0.17 | 14.7% | 0.35 | 143.6% | 0.23 | 56.1% | 0.15 | 0.0% |
| 10 | 50 | 0.50 | 127.7% | 0.33 | 51.8% | 0.44 | 101.3% | 0.31 | 41.9% | 0.22 | 0.0% |
| 15 | 59 | 0.63 | 91.0% | 0.50 | 52.8% | 0.55 | 67.5% | 0.42 | 29.4% | 0.33 | 0.0% |
| 20 | 68 | 0.75 | 56.0% | 0.67 | 38.6% | 0.67 | 40.2% | 0.57 | 18.4% | 0.48 | 0.0% |
| 25 | 77 | 0.88 | 25.4% | 0.83 | 19.4% | 0.82 | 18.1% | 0.76 | 8.7% | 0.70 | 0.0% |
| 30 | 86 | 1.00 | 0.0% | 1.00 | 0.0% | 1.00 | 0.0% | 1.00 | 0.0% | 1.00 | 0.0% |
| 35 | 95 | 1.13 | −20.6% | 1.17 | −17.6% | 1.21 | −14.8% | 1.31 | −7.7% | 1.42 | 0.0% |
| 40 | 104 | 1.25 | −37.0% | 1.33 | −32.8% | 1.45 | −27.1% | 1.69 | −14.6% | 1.98 | 0.0% |
| 45 | 113 | 1.38 | −50.0% | 1.50 | −45.5% | 1.72 | −37.3% | 2.18 | −20.8% | 2.75 | 0.0% |
| 50 | 122 | 1.50 | −60.3% | 1.67 | −55.8% | 2.04 | −45.8% | 2.78 | −26.4% | 3.77 | 0.0% |
| 55 | 131 | 1.63 | −68.3% | 1.83 | −64.3% | 2.41 | −53.0% | 3.52 | −31.4% | 5.13 | 0.0% |
| 60 | 140 | 1.75 | −74.7% | 2.00 | −71.0% | 2.83 | −59.0% | 4.42 | −36.0% | 6.91 | 0.0% |
| 65 | 149 | 1.88 | −79.7% | 2.17 | −76.5% | 3.31 | −64.1% | 5.52 | −40.1% | 9.22 | 0.0% |
| 70 | 158 | 2.00 | −83.6% | 2.33 | −80.9% | 3.85 | −68.5% | 6.85 | −43.9% | 12.20 | 0.0% |
| 80 | 176 | 2.25 | −89.2% | 2.67 | −87.2% | 5.14 | −75.4% | 10.35 | −50.4% | 20.87 | 0.0% |
| 90 | 194 | 2.50 | −92.8% | 3.00 | −91.3% | 6.75 | −80.5% | 15.30 | −55.9% | 34.67 | 0.0% |
| 100 | 212 | 2.75 | −95.1% | 3.33 | 94.1% | 8.74 | −84.4% | 22.13 | −60.5% | 56.03 | 0.0% |
| 110 | 230 | 3.00 | −96.6% | 3.67 | −95.8% | 11.16 | −87.4% | 31.40 | −64.4% | 88.31 | 0.0% |
| 120 | 248 | 3.25 | −97.6% | 4.00 | −97.1% | 14.09 | −89.6% | 43.77 | −67.8% | 136.01 | 0.0% |
| 130 | 266 | 3.50 | −98.3% | 4.33 | −97.9% | 17.57 | −91.4% | 60.02 | −70.7% | 205.02 | 0.0% |

TABLE 12

Conservative Nature of Improved Nurse-Saul (and First Alternative) and Improved Arrhenius Maturity Methods at $T_{ref} = 30°$ C.

| | | Equivalent Age Errors (if True Q = 3500 K) | | | | | | Equivalent Age Errors (if True Q = 6500 K) | | | | | |
|---|---|---|---|---|---|---|---|---|---|---|---|---|---|
| Temperature | | Improved Nurse-Saul | | Improved Nurse-Saul (Second Alternative) ($T_D = 9.0$ C.) | | Improved Arrhenius | | Improved Nurse-Saul | | Improved Nurse-Saul (Second Alternative) ($T_D = 9.0$ C.) | | Improved Arrhenius | |
| (° C.) | (° F.) | EAF | % Error | EAF | % Error | EAF | % Error | EAF | % Error | EAF | % Error | EAF | % Error |
| −10 | 14 | N/A | N/A | N/A | N/A | 0.04 | −77.8% | N/A | N/A | N/A | N/A | 0.04 | 0.0% |
| −5 | 23 | N/A | N/A | N/A | N/A | 0.06 | −72.6% | N/A | N/A | N/A | N/A | 0.06 | 0.0% |
| 0 | 32 | N/A | N/A | N/A | N/A | 0.09 | −66.3% | N/A | N/A | N/A | N/A | 0.09 | 0.0% |
| 5 | 41 | N/A | N/A | N/A | N/A | 0.15 | −58.9% | N/A | N/A | N/A | N/A | 0.15 | 0.0% |
| 10 | 50 | N/A | N/A | 0.05 | −89.2% | 0.22 | −50.3% | N/A | N/A | 0.05 | −89.2% | 0.22 | 0.0% |
| 15 | 59 | N/A | N/A | 0.29 | −47.9% | 0.33 | −40.3% | N/A | N/A | 0.29 | −47.9% | 0.33 | 0.0% |
| 20 | 68 | 0.29 | −56.7% | 0.52 | −22.3% | 0.48 | −28.7% | 0.29 | −56.7% | 0.52 | −22.3% | 0.48 | 0.0% |
| 25 | 77 | 0.65 | −21.6% | 0.76 | −7.5% | 0.70 | −15.3% | 0.65 | −21.6% | 0.76 | −7.5% | 0.70 | 0.0% |
| 30 | 86 | 1.00 | 0.0% | 1.00 | 0.0% | 1.00 | 0.0% | 1.00 | 0.0% | 1.00 | 0.0% | 1.00 | 0.0% |
| 35 | 95 | 1.19 | −1.3% | 1.24 | 2.6% | 1.21 | 0.0% | 1.19 | −1.3% | 1.24 | 2.6% | 1.21 | −14.8% |
| 40 | 104 | 1.38 | −4.5% | 1.48 | 2.1% | 1.45 | 0.0% | 1.38 | −4.5% | 1.48 | 2.1% | 1.45 | −27.1% |
| 45 | 113 | 1.57 | −8.8% | 1.71 | −0.6% | 1.72 | 0.0% | 1.57 | −8.8% | 1.71 | −0.6% | 1.72 | −37.3% |
| 50 | 122 | 1.76 | −13.8% | 1.95 | −4.5% | 2.04 | 0.0% | 1.76 | −13.8% | 1.95 | −4.5% | 2.04 | −45.8% |
| 55 | 131 | 1.95 | −19.0% | 2.19 | −9.2% | 2.41 | 0.0% | 1.95 | −19.0% | 2.19 | −9.2% | 2.41 | −53.0% |
| 60 | 140 | 2.14 | −24.3% | 2.43 | −14.2% | 2.83 | 0.0% | 2.14 | −24.3% | 2.43 | −14.2% | 2.83 | −59.0% |
| 65 | 149 | 2.33 | −29.4% | 2.67 | −19.4% | 3.31 | 0.0% | 2.33 | −29.4% | 2.67 | −19.4% | 3.31 | −64.1% |
| 70 | 158 | 2.52 | −34.4% | 2.90 | −24.5% | 3.85 | 0.0% | 2.52 | −34.4% | 2.90 | −24.5% | 3.85 | −68.5% |
| 80 | 176 | 2.91 | −43.4% | 3.38 | −34.2% | 5.14 | 0.0% | 2.91 | −43.4% | 3.38 | −34.2% | 5.14 | −75.4% |
| 90 | 194 | 3.29 | −51.3% | 3.86 | −42.8% | 6.75 | 0.0% | 3.29 | −51.3% | 3.86 | −42.8% | 6.75 | −80.5% |
| 100 | 212 | 3.67 | −58.0% | 4.33 | −50.4% | 8.74 | 0.0% | 3.67 | −58.0% | 4.33 | −50.4% | 8.74 | −84.4% |
| 110 | 230 | 4.05 | −63.7% | 4.81 | −56.9% | 11.16 | 0.0% | 4.05 | −63.7% | 4.81 | −56.9% | 11.16 | −87.4% |
| 120 | 248 | 4.43 | −68.5% | 5.29 | −62.5% | 14.09 | 0.0% | 4.43 | −68.5% | 5.29 | −62.5% | 14.09 | −89.6% |
| 130 | 266 | 4.81 | −72.6% | 5.76 | −67.2% | 17.57 | 0.0% | 4.81 | −72.6% | 5.76 | −67.2% | 17.57 | −91.4% |

TABLE 13

Unconservative Potential of Conventional Nurse-Saul and Arrhenius Maturity Methods at $T_{ref}$ = 50° C.

| Temperature | | To = −10° C. | | To = 0° C. | | Q = 3500 K | | Q = 5000 K | | Q = 6500 K | |
|---|---|---|---|---|---|---|---|---|---|---|---|
| (° C.) | (° F.) | EAF | % Error | EAF | % Error | EAF | % Error | EAF | % Error | EAF | % Error |
| Equivalent Age Errors (if True Q = 3500 K) | | | | | | | | | | | |
| −10 | 14 | 0.00 | N/A | N/A | N/A | 0.08 | 0.0% | 0.03 | −65.3% | 0.01 | −88.0% |
| −5 | 23 | 0.08 | −23.0% | N/A | N/A | 0.11 | 0.0% | 0.04 | −61.4% | 0.02 | −85.1% |
| 0 | 32 | 0.17 | 21.3% | 0.00 | N/A | 0.14 | 0.0% | 0.06 | −57.0% | 0.03 | −81.0% |
| 5 | 41 | 0.25 | 44.4% | 0.10 | −42.2% | 0.17 | 0.0% | 0.08 | −52.8% | 0.04 | −77.8% |
| 10 | 50 | 0.33 | 54.2% | 0.20 | −7.5% | 0.22 | 0.0% | 0.11 | −48.1% | 0.06 | −73.1% |
| 15 | 59 | 0.42 | 55.5% | 0.30 | 12.0% | 0.27 | 0.0% | 0.15 | −43.1% | 0.09 | −67.7% |
| 20 | 68 | 0.50 | 51.6% | 0.40 | 21.3% | 0.33 | 0.0% | 0.20 | −37.8% | 0.13 | −61.4% |
| 25 | 77 | 0.58 | 44.8% | 0.50 | 24.1% | 0.40 | 0.0% | 0.27 | −32.3% | 0.18 | −54.1% |
| 30 | 86 | 0.67 | 36.3% | 0.60 | 22.7% | 0.49 | 0.0% | 0.36 | −26.4% | 0.26 | −45.8% |
| 35 | 95 | 0.75 | 27.1% | 0.70 | 18.7% | 0.59 | 0.0% | 0.47 | −20.2% | 0.38 | −36.4% |
| 40 | 104 | 0.83 | 17.8% | 0.80 | 13.1% | 0.71 | 0.0% | 0.61 | −13.8% | 0.53 | −25.7% |
| 45 | 113 | 0.92 | 8.7% | 0.90 | 6.7% | 0.84 | 0.0% | 0.78 | −7.0% | 0.73 | −13.6% |
| 50 | 122 | 1.00 | 0.0% | 1.00 | 0.0% | 1.00 | 0.0% | 1.00 | 0.0% | 1.00 | 0.0% |
| 55 | 131 | 1.08 | −8.2% | 1.10 | −6.7% | 1.18 | 0.0% | 1.27 | 7.3% | 1.36 | 15.2% |
| 60 | 140 | 1.17 | −15.7% | 1.20 | −13.3% | 1.38 | 0.0% | 1.59 | 15.0% | 1.83 | 32.2% |
| 65 | 149 | 1.25 | −22.7% | 1.30 | −19.6% | 1.62 | 0.0% | 1.99 | 22.9% | 2.44 | 51.0% |
| 70 | 158 | 1.33 | −29.1% | 1.40 | −25.6% | 1.88 | 0.0% | 2.47 | 31.1% | 3.23 | 71.9% |
| 80 | 176 | 1.50 | −40.3% | 1.60 | −36.3% | 2.51 | 0.0% | 3.73 | 48.4% | 5.53 | 120.2% |
| 90 | 194 | 1.67 | −49.5% | 1.80 | −45.5% | 3.30 | 0.0% | 5.51 | 66.8% | 9.18 | 178.3% |
| 100 | 212 | 1.83 | −57.1% | 2.00 | −53.2% | 4.27 | 0.0% | 7.96 | 86.4% | 14.84 | 247.3% |
| 110 | 230 | 2.00 | −63.4% | 2.20 | −59.7% | 5.46 | 0.0% | 11.30 | 107.0% | 23.40 | 328.5% |
| 120 | 248 | 2.17 | −68.6% | 2.40 | −65.2% | 6.89 | 0.0% | 15.76 | 128.7% | 36.03 | 423.0% |
| 130 | 266 | 2.33 | −72.8% | 2.60 | −69.7% | 8.59 | 0.0% | 21.61 | 151.4% | 54.32 | 532.0% |
| Equivalent Age Errors (if True Q = 6500 K) | | | | | | | | | | | |
| −10 | 14 | 0.00 | N/A | N/A | N/A | 0.08 | 732.2% | 0.03 | 188.5% | 0.01 | 0.0% |
| −5 | 23 | 0.08 | 418.1% | N/A | N/A | 0.11 | 572.7% | 0.04 | 159.4% | 0.02 | 0.0% |
| 0 | 32 | 0.17 | 564.5% | 0.00 | N/A | 0.14 | 448.0% | 0.06 | 134.1% | 0.03 | 0.0% |
| 5 | 41 | 0.25 | 549.6% | 0.10 | 159.8% | 0.17 | 349.7% | 0.08 | 112.1% | 0.04 | 0.0% |
| 10 | 50 | 0.33 | 473.0% | 0.20 | 243.8% | 0.22 | 271.6% | 0.11 | 92.8% | 0.06 | 0.0% |
| 15 | 59 | 0.42 | 380.7% | 0.30 | 246.1% | 0.27 | 209.2% | 0.15 | 75.8% | 0.09 | 0.0% |
| 20 | 68 | 0.50 | 292.5% | 0.40 | 214.0% | 0.33 | 158.8% | 0.20 | 60.9% | 0.13 | 0.0% |
| 25 | 77 | 0.58 | 215.6% | 0.50 | 170.5% | 0.40 | 118.0% | 0.27 | 47.6% | 0.18 | 0.0% |
| 30 | 86 | 0.67 | 151.6% | 0.60 | 126.5% | 0.49 | 84.6% | 0.36 | 35.9% | 0.26 | 0.0% |
| 35 | 95 | 0.75 | 99.8% | 0.70 | 86.5% | 0.59 | 57.2% | 0.47 | 25.4% | 0.38 | 0.0% |
| 40 | 104 | 0.83 | 58.5% | 0.80 | 52.2% | 0.71 | 34.5% | 0.61 | 16.0% | 0.53 | 0.0% |
| 45 | 113 | 0.92 | 25.8% | 0.90 | 23.5% | 0.84 | 15.7% | 0.78 | 7.6% | 0.73 | 0.0% |
| 50 | 122 | 1.00 | 0.0% | 1.00 | 0.0% | 1.00 | 0.0% | 1.00 | 0.0% | 1.00 | 0.0% |
| 55 | 131 | 1.08 | −20.3% | 1.10 | −19.1% | 1.18 | −13.2% | 1.27 | −6.8% | 1.36 | 0.0% |
| 60 | 140 | 1.17 | −36.2% | 1.20 | −34.4% | 1.38 | −24.3% | 1.59 | −13.0% | 1.83 | 0.0% |
| 65 | 149 | 1.25 | −48.6% | 1.30 | −46.8% | 1.62 | −33.8% | 1.99 | −18.6% | 2.44 | 0.0% |
| 70 | 158 | 1.33 | −58.8% | 1.40 | −56.7% | 1.88 | −41.8% | 2.47 | −23.7% | 3.23 | 0.0% |
| 80 | 176 | 1.50 | −72.9% | 1.60 | −71.1% | 2.51 | −54.6% | 3.73 | −32.6% | 5.53 | 0.0% |
| 90 | 194 | 1.67 | −81.9% | 1.80 | −80.4% | 3.30 | −64.1% | 5.51 | −40.1% | 9.18 | 0.0% |
| 100 | 212 | 1.83 | −87.6% | 2.00 | −86.5% | 4.27 | −71.2% | 7.96 | −46.3% | 14.84 | 0.0% |
| 110 | 230 | 2.00 | −91.5% | 2.20 | −90.6% | 5.46 | −76.7% | 11.30 | −51.7% | 23.40 | 0.0% |
| 120 | 248 | 2.17 | −94.0% | 2.40 | −93.3% | 6.89 | −80.9% | 15.76 | −56.3% | 36.03 | 0.0% |
| 130 | 266 | 2.33 | −95.7% | 2.60 | −95.2% | 8.59 | −84.2% | 21.61 | −60.2% | 54.32 | 0.0% |

TABLE 14

Conservative Nature of Improved Nurse-Saul (and First Alternative) and Improved Arrhenius Maturity Methods at $T_{ref}$ = 50° C.

| | | Equivalent Age Errors (if True Q = 3500 K) | | | | | |
|---|---|---|---|---|---|---|---|
| Temperature | | Improved Nurse-Saul | | Improved Nurse-Saul (Second Alternative) (To = 26.0 C.) | | Improved Arrhenius | |
| (° C.) | (° F.) | EAF | % Error | EAF | % Error | EAF | % Error |
| −10 | 14 | N/A | N/A | N/A | N/A | 0.01 | −88.0% |
| −5 | 23 | N/A | N/A | N/A | N/A | 0.02 | −85.1% |
| 0 | 32 | N/A | N/A | N/A | N/A | 0.03 | −81.8% |
| 5 | 41 | N/A | N/A | N/A | N/A | 0.04 | −77.8% |
| 10 | 50 | N/A | N/A | N/A | N/A | 0.06 | −73.1% |
| 15 | 59 | N/A | N/A | N/A | N/A | 0.09 | −67.7% |
| 20 | 68 | N/A | N/A | N/A | N/A | 0.13 | −61.4% |
| 25 | 77 | N/A | N/A | N/A | N/A | 0.18 | −54.1% |
| 30 | 86 | N/A | N/A | 0.17 | −65.9% | 0.26 | −45.8% |
| 35 | 95 | 0.07 | −88.9% | 0.38 | −36.4% | 0.38 | −36.4% |
| 40 | 104 | 0.38 | −46.7% | 0.58 | −17.5% | 0.53 | −25.7% |
| 45 | 113 | 0.69 | −18.4% | 0.79 | −6.1% | 0.73 | −13.6% |
| 50 | 122 | 1.00 | 0.0% | 1.00 | 0.0% | 1.00 | 0.0% |
| 55 | 131 | 1.17 | −1.0% | 1.21 | 2.4% | 1.18 | 0.0% |
| 60 | 140 | 1.34 | −3.5% | 1.42 | 2.3% | 1.38 | 0.0% |
| 65 | 149 | 1.50 | 7.1% | 1.63 | 0.5% | 1.62 | 0.0% |

TABLE 14-continued

Conservative Nature of Improved Nurse-Saul (and First Alternative) and Improved Arrhenius Maturity Methods at $T_{ref}$ = 50° C.

| | | | | | | | |
|---|---|---|---|---|---|---|---|
| 70 | 158 | 1.67 | −11.2% | 1.83 | −2.5% | 1.88 | 0.0% |
| 80 | 176 | 2.01 | −20.1% | 2.25 | −10.4% | 2.51 | 0.0% |
| 90 | 194 | 2.34 | −29.0% | 2.67 | −19.2% | 3.30 | 0.0% |
| 100 | 212 | 2.68 | −37.4% | 3.08 | −27.9% | 4.27 | 0.0% |
| 110 | 230 | 3.01 | −44.8% | 3.50 | −35.9% | 5.46 | 0.0% |
| 120 | 248 | 3.35 | −51.4% | 3.92 | −43.2% | 6.89 | 0.0% |
| 130 | 266 | 3.68 | −57.1% | 4.33 | −49.6% | 8.59 | 0.0% |

Equivalent Age Errors (if True Q = 6500 K)

| Temperature | | Improved Nurse-Saul | | Improved Nurse-Saul (Second Alternative) (To = 26.0 C.) | | Arrhenius | |
|---|---|---|---|---|---|---|---|
| (° C.) | (° F.) | EAF | % Error | EAF | % Error | EAF | % Error |
| −10 | 14 | N/A | N/A | N/A | N/A | 0.01 | 0.0% |
| −5 | 23 | N/A | N/A | N/A | N/A | 0.02 | 0.0% |
| 0 | 32 | N/A | N/A | N/A | N/A | 0.03 | 0.0% |
| 5 | 41 | N/A | N/A | N/A | N/A | 0.04 | 0.0% |
| 10 | 50 | N/A | N/A | N/A | N/A | 0.06 | 0.0% |
| 15 | 59 | N/A | N/A | N/A | N/A | 0.09 | 0.0% |
| 20 | 68 | N/A | N/A | N/A | N/A | 0.13 | 0.0% |
| 25 | 77 | N/A | N/A | N/A | N/A | 0.18 | 0.0% |
| 30 | 86 | N/A | N/A | 0.17 | −65.9% | 0.26 | 0.0% |
| 35 | 95 | 0.07 | −88.9% | 0.38 | −36.4% | 0.38 | 0.0% |
| 40 | 104 | 0.38 | −46.7% | 0.58 | −17.5% | 0.53 | 0.0% |
| 45 | 113 | 0.60 | −18.4% | 0.79 | −6.1% | 0.73 | 0.0% |
| 50 | 122 | 1.00 | 0.0% | 1.00 | 0.0% | 1.00 | 0.0% |
| 55 | 131 | 1.17 | −1.0% | 1.21 | 2.4% | 1.18 | −13.2% |
| 60 | 140 | 1.34 | −3.5% | 1.42 | 2.3% | 1.38 | −24.3% |
| 65 | 149 | 1.50 | −7.1% | 1.63 | 0.5% | 1.62 | −33.8% |
| 70 | 158 | 1.67 | −11.2% | 1.83 | −2.5% | 1.88 | −41.8% |
| 80 | 176 | 2.01 | −20.1% | 2.25 | −10.4% | 2.51 | −54.6% |
| 90 | 194 | 2.34 | −29.0% | 2.67 | −19.2% | 3.30 | −64.1% |
| 100 | 212 | 2.68 | −37.4% | 3.08 | −27.9% | 4.27 | −71.2% |
| 110 | 230 | 3.01 | −44.8% | 3.50 | −35.9% | 5.46 | −76.7% |
| 120 | 248 | 3.35 | −51.4% | 3.92 | −43.2% | 6.89 | −80.9% |
| 130 | 266 | 3.68 | −57.1% | 4.33 | −49.6% | 8.59 | −84.2% |

TABLE 15

Unconservative Potential of Conventional Nurse-Saul and Arrhenius Maturity Methods at $T_{ref}$ = 70° C.

| Temperature | | To = −10° C. | | To = 0° C. | | Q = 3500 K | | Q = 5000 K | | Q = 6500 K | |
|---|---|---|---|---|---|---|---|---|---|---|---|
| (° C.) | (° F.) | EAF | % Error | EAF | % Error | EAF | % Error | EAF | % Error | EAF | % Error |
| Equivalent Age Errors (if True Q = 3500 K) | | | | | | | | | | | |
| −10 | 14 | 0.00 | N/A | N/A | N/A | 0.04 | 0.0% | 0.01 | −73.6% | 0.00 | −93.0% |
| −5 | 23 | 0.06 | 8.7% | N/A | N/A | 0.06 | 0.0% | 0.02 | −70.6% | 0.00 | −91.4% |
| 0 | 32 | 0.13 | 71.1% | 0.00 | N/A | 0.07 | 0.0% | 0.02 | −67.4% | 0.01 | −89.4% |
| 5 | 41 | 0.19 | 103.8% | 0.07 | −22.4% | 0.09 | 0.0% | 0.03 | −64.0% | 0.01 | −87.1% |
| 10 | 50 | 0.25 | 117.5% | 0.14 | 24.3% | 0.11 | 0.0% | 0.05 | −60.4% | 0.02 | −84.3% |
| 15 | 59 | 0.31 | 119.4% | 0.21 | 50.4% | 0.14 | 0.0% | 0.06 | −56.6% | 0.03 | −81.2% |
| 20 | 68 | 0.38 | 113.9% | 0.29 | 63.0% | 0.18 | 0.0% | 0.08 | −52.6% | 0.04 | −77.5% |
| 25 | 77 | 0.44 | 104.3% | 0.36 | 66.7% | 0.21 | 0.0% | 0.11 | −48.3% | 0.06 | −73.3% |
| 30 | 86 | 0.50 | 92.3% | 0.43 | 64.8% | 0.26 | 0.0% | 0.15 | −43.9% | 0.08 | −68.5% |
| 35 | 95 | 0.56 | 79.4% | 0.50 | 59.4% | 0.31 | 0.0% | 0.19 | −39.2% | 0.12 | −63.0% |
| 40 | 104 | 0.63 | 66.2% | 0.57 | 52.0% | 0.38 | 0.0% | 0.25 | −34.2% | 0.16 | −56.8% |
| 45 | 113 | 0.69 | 53.3% | 0.64 | 43.4% | 0.45 | 0.0% | 0.32 | −29.1% | 0.23 | −49.7% |
| 50 | 122 | 0.75 | 41.1% | 0.71 | 34.4% | 0.53 | 0.0% | 0.41 | −23.7% | 0.31 | −41.8% |
| 55 | 131 | 0.81 | 29.6% | 0.79 | 25.3% | 0.63 | 0.0% | 0.51 | −18.1% | 0.42 | −33.0% |
| 60 | 140 | 0.88 | 18.9% | 0.86 | 16.4% | 0.74 | 0.0% | 0.65 | −12.3% | 0.57 | −23.1% |
| 65 | 149 | 0.94 | 9.0% | 0.93 | 8.0% | 0.86 | 0.0% | 0.81 | −6.3% | 0.76 | −12.1% |
| 70 | 158 | 1.00 | 0.0% | 1.00 | 0.0% | 1.00 | 0.0% | 1.00 | 0.0% | 1.00 | 0.0% |
| 80 | 176 | 1.13 | −15.7% | 1.14 | −14.4% | 1.34 | 0.0% | 1.51 | 13.2% | 1.71 | 28.1% |
| 90 | 194 | 1.25 | −28.8% | 1.29 | −26.7% | 1.75 | 0.0% | 2.23 | 27.2% | 2.84 | 61.9% |
| 100 | 212 | 1.38 | −39.5% | 1.43 | −37.1% | 2.27 | 0.0% | 3.23 | 42.2% | 4.59 | 102.1% |
| 110 | 230 | 1.50 | −48.3% | 1.57 | −45.9% | 2.90 | 0.0% | 4.58 | 57.9% | 7.24 | 149.3% |
| 120 | 248 | 1.63 | −55.6% | 1.71 | −53.2% | 3.66 | 0.0% | 6.39 | 74.4% | 11.15 | 204.3% |
| 130 | 266 | 1.75 | −61.7% | 1.86 | −59.4% | 4.57 | 0.0% | 8.76 | 91.8% | 16.80 | 267.7% |
| Equivalent Age Errors (if True Q = 6500 K) | | | | | | | | | | | |
| −10 | 14 | 0.00 | N/A | N/A | N/A | 0.04 | 1330.3% | 0.01 | 278.2% | 0.00 | 0.0% |
| −5 | 23 | 0.06 | 1156.2% | N/A | N/A | 0.06 | 1056.1% | 0.02 | 240.0% | 0.00 | 0.0% |
| 0 | 32 | 0.13 | 1511.3% | 0.00 | N/A | 0.07 | 841.8% | 0.02 | 206.9% | 0.01 | 0.0% |
| 5 | 41 | 0.19 | 1475.1% | 0.07 | 500.0% | 0.09 | 672.9% | 0.03 | 178.0% | 0.01 | 0.0% |
| 10 | 50 | 0.25 | 1289.4% | 0.14 | 694.0% | 0.11 | 538.8% | 0.05 | 152.7% | 0.02 | 0.0% |
| 15 | 59 | 0.31 | 1065.6% | 0.21 | 699.3% | 0.14 | 431.4% | 0.06 | 130.5% | 0.03 | 0.0% |
| 20 | 68 | 0.38 | 851.7% | 0.29 | 625.1% | 0.18 | 344.8% | 0.08 | 110.9% | 0.04 | 0.0% |
| 25 | 77 | 0.44 | 665.2% | 0.36 | 524.7% | 0.21 | 274.6% | 0.11 | 93.6% | 0.06 | 0.0% |
| 30 | 86 | 0.50 | 510.2% | 0.43 | 423.0% | 0.26 | 217.3% | 0.15 | 78.1% | 0.08 | 0.0% |
| 35 | 95 | 0.56 | 384.6% | 0.50 | 330.7% | 0.31 | 170.2% | 0.19 | 64.4% | 0.12 | 0.0% |
| 40 | 104 | 0.63 | 284.3% | 0.57 | 251.4% | 0.38 | 131.2% | 0.25 | 52.1% | 0.16 | 0.0% |
| 45 | 113 | 0.69 | 205.0% | 0.64 | 185.2% | 0.45 | 98.9% | 0.32 | 41.0% | 0.23 | 0.0% |
| 50 | 122 | 0.75 | 142.5% | 0.71 | 130.9% | 0.53 | 71.9% | 0.41 | 31.1% | 0.31 | 0.0% |
| 55 | 131 | 0.81 | 93.3% | 0.79 | 86.9% | 0.63 | 49.2% | 0.51 | 22.1% | 0.42 | 0.0% |
| 60 | 140 | 0.88 | 54.6% | 0.86 | 51.4% | 0.74 | 30.0% | 0.65 | 14.0% | 0.57 | 0.0% |
| 65 | 149 | 0.94 | 24.1% | 0.93 | 22.9% | 0.86 | 13.8% | 0.81 | 6.7% | 0.76 | 0.0% |

TABLE 15-continued

Unconservative Potential of Conventional Nurse-Saul and
Arrhenius Maturity Methods at $T_{ref} = 70°$ C.

| Temperature | | To = −10° C. | | To = 0° C. | | Q = 3500 K | | Q = 5000 K | | Q = 6500 K | |
|---|---|---|---|---|---|---|---|---|---|---|---|
| (° C.) | (° F.) | EAF | % Error | EAF | % Error | EAF | % Error | EAF | % Error | EAF | % Error |
| 70 | 158 | 1.00 | 0.0% | 1.00 | 0.0% | 1.00 | 0.0% | 1.00 | 0.0% | 1.00 | 0.0% |
| 80 | 176 | 1.13 | −34.2% | 1.14 | −33.2% | 1.34 | −21.9% | 1.51 | −11.7% | 1.71 | 0.0% |
| 90 | 194 | 1.25 | −56.0% | 1.29 | −54.7% | 1.75 | −38.2% | 2.23 | −21.4% | 2.84 | 0.0% |
| 100 | 212 | 1.38 | −70.1% | 1.43 | −68.9% | 2.27 | −50.5% | 3.23 | −29.7% | 4.59 | 0.0% |
| 110 | 230 | 1.50 | −79.3% | 1.57 | −78.3% | 2.90 | −59.9% | 4.58 | −36.7% | 7.24 | 0.0% |
| 120 | 248 | 1.63 | −85.4% | 1.71 | −84.6% | 3.66 | −67.1% | 6.39 | −42.7% | 11.15 | 0.0% |
| 130 | 266 | 1.75 | −89.6% | 1.86 | −88.3% | 4.57 | −72.8% | 8.76 | −47.9% | 16.80 | 0.0% |

TABLE 16

Conservative Nature of Improved Nurse-Saul (and First Alternative) and
Improved Arrhenius Maturity Methods at $T_{ref} = 70°$ C.

| | | Equivalent Age Errors (if True Q = 3500 K) | | | | | | Equivalent Age Errors (if True Q = 6500 K) | | | | | |
|---|---|---|---|---|---|---|---|---|---|---|---|---|---|
| Temperature | | Improved Nurse-Saul | | Improved Nurse-Saul (Second Alternative) (To = 43.0 C.) | | Improved Arrhenius | | Temperature | | Improved Nurse-Saul | | Improved Nurse-Saul (Second Alternative) (To = 43.0 C.) | | Arrhenius | |
| (° C.) | (° F.) | EAF | % Error | EAF | % Error | EAF | % Error | (° C.) | (° F.) | EAF | % Error | EAF | % Error | EAF | % Error |
| −10 | 14 | N/A | N/A | N/A | N/A | 0.00 | −93.0% | −10 | 14 | N/A | N/A | N/A | N/A | 0.00 | 0.0% |
| −5 | 23 | N/A | N/A | N/A | N/A | 0.00 | −91.4% | −5 | 23 | N/A | N/A | N/A | N/A | 0.00 | 0.0% |
| 0 | 32 | N/A | N/A | N/A | N/A | 0.01 | −89.4% | 0 | 32 | N/A | N/A | N/A | N/A | 0.01 | 0.0% |
| 5 | 41 | N/A | N/A | N/A | N/A | 0.01 | −87.1% | 5 | 41 | N/A | N/A | N/A | N/A | 0.01 | 0.0% |
| 10 | 50 | N/A | N/A | N/A | N/A | 0.02 | 84.3% | 10 | 50 | N/A | N/A | N/A | N/A | 0.02 | 0.0% |
| 15 | 59 | N/A | N/A | N/A | N/A | 0.03 | −81.2% | 15 | 59 | N/A | N/A | N/A | N/A | 0.03 | 0.0% |
| 20 | 68 | N/A | N/A | N/A | N/A | 0.04 | −77.5% | 20 | 68 | N/A | N/A | N/A | N/A | 0.04 | 0.0% |
| 25 | 77 | N/A | N/A | N/A | N/A | 0.06 | −73.3% | 25 | 77 | N/A | N/A | N/A | N/A | 0.06 | 0.0% |
| 30 | 86 | N/A | N/A | N/A | N/A | 0.08 | −68.5% | 30 | 86 | N/A | N/A | N/A | N/A | 0.08 | 0.0% |
| 35 | 95 | N/A | N/A | N/A | N/A | 0.12 | −63.0% | 35 | 95 | N/A | N/A | N/A | N/A | 0.12 | 0.0% |
| 40 | 104 | N/A | N/A | N/A | N/A | 0.16 | −56.8% | 40 | 104 | N/A | N/A | N/A | N/A | 0.16 | 0.0% |
| 45 | 113 | N/A | N/A | 0.07 | −83.5% | 0.23 | −49.7% | 45 | 113 | N/A | N/A | 0.07 | −83.5% | 0.23 | 0.0% |
| 50 | 122 | N/A | N/A | 0.26 | −51.2% | 0.31 | −41.8% | 50 | 122 | N/A | N/A | 0.26 | −51.2% | 0.31 | 0.0% |
| 55 | 131 | 0.17 | −72.7% | 0.44 | −29.1% | 0.42 | −33.0% | 55 | 131 | 0.17 | −72.7% | 0.44 | −29.1% | 0.42 | 0.0% |
| 60 | 140 | 0.45 | −39.2% | 0.63 | −14.5% | 0.57 | −20.1% | 60 | 140 | 0.45 | −39.2% | 0.63 | −14.5% | 0.57 | 0.0% |
| 65 | 149 | 0.72 | −15.8% | 0.81 | −5.2% | 0.76 | −12.1% | 65 | 149 | 0.72 | −15.8% | 0.81 | −5.2% | 0.76 | 0.0% |
| 70 | 158 | 1.00 | 0.0% | 1.00 | 0.0% | 1.00 | 0.0% | 70 | 158 | 1.00 | 0.0% | 1.00 | 0.0% | 1.00 | 0.0% |
| 80 | 176 | 1.30 | −2.8% | 1.37 | 2.6% | 1.34 | 0.0% | 80 | 176 | 1.30 | −2.8% | 1.37 | 2.6% | 1.34 | −21.9% |
| 90 | 194 | 1.59 | −9.1% | 1.74 | −0.8% | 1.75 | 0.0% | 90 | 194 | 1.59 | −9.1% | 1.74 | −0.8% | 1.75 | −38.2% |
| 100 | 212 | 1.89 | −16.7% | 2.11 | −7.1% | 2.27 | 0.0% | 100 | 212 | 1.89 | −16.7% | 2.11 | −7.1% | 2.27 | −50.5% |
| 110 | 230 | 2.19 | −24.6% | 2.48 | −14.5% | 2.90 | 0.0% | 110 | 230 | 2.19 | −24.6% | 2.48 | −14.5% | 2.90 | −59.9% |
| 120 | 240 | 2.49 | −32.1% | 2.05 | −22.1% | 3.66 | 0.0% | 120 | 248 | 2.49 | −32.1% | 2.85 | −22.1% | 3.66 | −67.1% |
| 130 | 256 | 2.78 | −39.0% | 3.22 | −29.5% | 4.57 | 0.0% | 130 | 256 | 2.78 | −39.0% | 3.22 | −29.5% | 4.57 | −72.8% |

TABLE 17

Unconservative Potential of Conventional Nurse-Saul and
Arrhenius Maturity Methods at $T_{ref} = 90°$ C.

| Temperature | | To = −10° C. | | To = 0° C. | | Q = 3500 K | | Q = 5000 K | | Q = 6500 K | |
|---|---|---|---|---|---|---|---|---|---|---|---|
| (° C.) | (° F.) | EAF | % Error | EAF | % Error | EAF | % Error | EAF | % Error | EAF | % Error |
| | | | | | | Equivalent Age Errors (if True Q = 3500 K) | | | | | |
| −10 | 14 | 0.00 | N/A | N/A | N/A | 0.03 | 0.0% | 0.01 | −79.2% | 0.00 | −95.7% |
| −5 | 23 | 0.05 | 52.5% | N/A | N/A | 0.03 | 0.0% | 0.01 | −76.9% | 0.00 | −94.7% |
| 0 | 32 | 0.10 | 140.1% | 0.00 | N/A | 0.04 | 0.0% | 0.01 | −74.4% | 0.00 | −93.4% |
| 5 | 41 | 0.15 | 186.0% | 0.06 | 5.9% | 0.05 | 0.0% | 0.01 | −71.7% | 0.00 | −92.0% |
| 10 | 50 | 0.20 | 206.3% | 0.11 | 69.6% | 0.07 | 0.0% | 0.02 | −68.9% | 0.01 | −90.3% |
| 15 | 59 | 0.25 | 207.9% | 0.17 | 105.3% | 0.08 | 0.0% | 0.03 | −65.9% | 0.01 | −88.4% |
| 20 | 68 | 0.30 | 200.3% | 0.22 | 122.4% | 0.10 | 0.0% | 0.04 | −62.7% | 0.01 | −86.1% |
| 25 | 77 | 0.35 | 186.7% | 0.28 | 127.5% | 0.12 | 0.0% | 0.05 | −59.4% | 0.02 | −83.5% |
| 30 | 86 | 0.40 | 169.9% | 0.33 | 124.9% | 0.15 | 0.0% | 0.07 | −55.9% | 0.03 | −80.5% |

TABLE 17-continued

Unconservative Potential of Conventional Nurse-Saul and
Arrhenius Maturity Methods at $T_{ref} = 90°$ C.

| Temperature | | To = −10° C. | | To = 0° C. | | Q = 3500 K | | Q = 5000 K | | Q = 6500 K | |
|---|---|---|---|---|---|---|---|---|---|---|---|
| (° C.) | (° F.) | EAF | % Error | EAF | % Error | EAF | % Error | EAF | % Error | EAF | % Error |
| 35 | 95 | 0.45 | 151.7% | 0.39 | 117.6% | 0.18 | 0.0% | 0.09 | −52.2% | 0.04 | −77.1% |
| 40 | 104 | 0.50 | 133.3% | 0.44 | 107.4% | 0.21 | 0.0% | 0.11 | −48.3% | 0.06 | −73.3% |
| 45 | 110 | 0.55 | 115.2% | 0.50 | 95.7% | 0.26 | 0.0% | 0.14 | −44.0% | 0.00 | −68.9% |
| 50 | 122 | 0.60 | 98.0% | 0.56 | 83.4% | 0.30 | 0.0% | 0.18 | −40.1% | 0.11 | −64.1% |
| 55 | 131 | 0.65 | 81.9% | 0.61 | 71.0% | 0.36 | 0.0% | 0.23 | −35.7% | 0.15 | −58.6% |
| 60 | 140 | 0.70 | 66.9% | 0.67 | 58.9% | 0.42 | 0.0% | 0.29 | −31.1% | 0.20 | −52.5% |
| 65 | 149 | 0.75 | 53.0% | 0.72 | 47.4% | 0.49 | 0.0% | 0.36 | −26.3% | 0.27 | −45.7% |
| 70 | 158 | 0.80 | 40.4% | 0.78 | 36.5% | 0.57 | 0.0% | 0.45 | −21.4% | 0.35 | −38.2% |
| 80 | 176 | 0.90 | 18.3% | 0.89 | 16.8% | 0.76 | 0.0% | 0.68 | −11.0% | 0.30 | −20.9% |
| 90 | 194 | 1.00 | 0.0% | 1.00 | 0.0% | 1.00 | 0.0% | 1.00 | 0.0% | 1.00 | 0.0% |
| 100 | 212 | 1.10 | −15.1% | 1.11 | −14.2% | 1.29 | 0.0% | 1.45 | 11.7% | 1.52 | 24.8% |
| 110 | 230 | 1.20 | −27.5% | 1.22 | −26.1% | 1.65 | 0.0% | 2.05 | 24.1% | 2.55 | 54.0% |
| 120 | 248 | 1.30 | −37.7% | 1.33 | −36.1% | 2.09 | 0.0% | 2.86 | 37.1% | 3.32 | 87.9% |
| 130 | 266 | 1.40 | −46.2% | 1.44 | −44.5% | 2.60 | 0.0% | 3.92 | 50.7% | 5.31 | 127.1% |
| Equivalent Age Errors (if True Q = 6500 K) | | | | | | | | | | | |
| −10 | 14 | 0.00 | N/A | N/A | N/A | 0.03 | 2215.0% | 0.01 | 381.2% | 0.00 | 0.0% |
| −5 | 20 | 0.05 | 2755.0% | N/A | N/A | 0.00 | 1772.0% | 0.01 | 332.7% | 0.00 | 0.0% |
| 0 | 32 | 0.10 | 3562.0% | 0.00 | N/A | 0.04 | 1425.0% | 0.01 | 290.5% | 0.00 | 0.0% |
| 5 | 41 | 0.15 | 3479.6% | 0.06 | 1225.8% | 0.05 | 1151.5% | 0.01 | 253.8% | 0.01 | 0.0% |
| 10 | 50 | 0.20 | 3057.7% | 0.11 | 1654.3% | 0.07 | 934.2% | 0.02 | 221.6% | 0.01 | 0.0% |
| 15 | 59 | 0.25 | 2549.1% | 0.17 | 1666.1% | 0.08 | 760.4% | 0.03 | 193.3% | 0.01 | 0.0% |
| 20 | 68 | 0.30 | 2062.8% | 0.22 | 1502.1% | 0.10 | 620.3% | 0.04 | 168.4% | 0.01 | 0.0% |
| 25 | 77 | 0.35 | 1639.0% | 0.28 | 1280.2% | 0.12 | 506.6% | 0.05 | 146.3% | 0.02 | 0.0% |
| 30 | 86 | 0.40 | 1286.7% | 0.33 | 1055.6% | 0.15 | 413.7% | 0.07 | 126.7% | 0.03 | 0.0% |
| 35 | 95 | 0.45 | 1001.3% | 0.39 | 851.7% | 0.18 | 337.5% | 0.09 | 109.2% | 0.04 | 0.0% |
| 40 | 104 | 0.50 | 773.5% | 0.44 | 676.4% | 0.21 | 274.4% | 0.11 | 93.5% | 0.06 | 0.0% |
| 45 | 113 | 0.55 | 593.2% | 0.50 | 530.1% | 0.26 | 222.0% | 0.14 | 79.5% | 0.08 | 0.0% |
| 50 | 122 | 0.60 | 451.1% | 0.56 | 410.2% | 0.30 | 178.3% | 0.18 | 66.8% | 0.11 | 0.0% |
| 55 | 131 | 0.65 | 339.3% | 0.61 | 313.0% | 0.36 | 141.5% | 0.23 | 55.4% | 0.15 | 0.0% |
| 60 | 140 | 0.70 | 251.3% | 0.67 | 234.6% | 0.42 | 110.5% | 0.29 | 45.1% | 0.20 | 0.0% |
| 65 | 149 | 0.75 | 182.0% | 0.72 | 171.6% | 0.49 | 84.3% | 0.36 | 35.7% | 0.27 | 0.0% |
| 70 | 158 | 0.80 | 127.3% | 0.78 | 121.0% | 0.57 | 61.9% | 0.45 | 27.2% | 0.35 | 0.0% |
| 80 | 176 | 0.90 | 49.5% | 0.89 | 47.6% | 0.76 | 26.4% | 0.68 | 12.4% | 0.60 | 0.0% |
| 90 | 194 | 1.00 | 0.0% | 1.00 | 0.0% | 1.00 | 0.0% | 1.00 | 0.0% | 1.00 | 0.0% |
| 100 | 212 | 1.10 | −31.9% | 1.11 | −31.3% | 1.29 | −19.9% | 1.45 | −10.5% | 1.32 | 0.0% |
| 110 | 230 | 1.20 | −52.9% | 1.22 | −52.3% | 1.65 | −35.1% | 2.05 | −19.4% | 2.55 | 0.0% |
| 120 | 248 | 1.30 | −66.9% | 1.33 | −66.3% | 2.09 | −46.8% | 2.86 | −27.1% | 3.92 | 0.0% |
| 130 | 266 | 1.40 | −76.3% | 1.44 | −75.6% | 2.60 | −56.0% | 3.92 | −33.6% | 5.91 | 0.0% |

TABLE 18

Conservative Nature of Improved Nurse-Saul (and First Alternative) and
Improved Arrhenius Maturity Methods at $T_{ref} = 90°$ C.

| | | Equivalent Age Errors (if True Q = 3500 K) | | | | | |
|---|---|---|---|---|---|---|---|
| Temperature | | Improved Nurse-Saul | | Improved Nurse-Saul (Second Alternative) (To = 60.0 C.) | | Improved Arrhenius | |
| (° C.) | (° F.) | EAF | % Error | EAF | % Error | EAF | % Error |
| −10 | 14 | N/A | N/A | N/A | N/A | 0.00 | −95.7% |
| −5 | 23 | N/A | N/A | N/A | N/A | 0.00 | −94.7% |
| 0 | 32 | N/A | N/A | N/A | N/A | 0.00 | −93.4% |
| 5 | 41 | N/A | N/A | N/A | N/A | 0.00 | −92.0% |
| 10 | 50 | N/A | N/A | N/A | N/A | 0.01 | −90.3% |
| 15 | 59 | N/A | N/A | N/A | N/A | 0.01 | −88.4% |
| 20 | 68 | N/A | N/A | N/A | N/A | 0.01 | −86.1% |
| 25 | 77 | N/A | N/A | N/A | N/A | 0.02 | −83.5% |
| 30 | 86 | N/A | N/A | N/A | N/A | 0.03 | −80.5% |
| 35 | 95 | N/A | N/A | N/A | N/A | 0.04 | −77.1% |
| 40 | 104 | N/A | N/A | N/A | N/A | 0.06 | −73.3% |
| 45 | 113 | N/A | N/A | N/A | N/A | 0.08 | −68.9% |
| 50 | 122 | N/A | N/A | N/A | N/A | 0.11 | −64.1% |
| 55 | 131 | N/A | N/A | N/A | N/A | 0.15 | −58.6% |
| 60 | 140 | N/A | N/A | 0.00 | N/A | 0.20 | −52.5% |
| 65 | 149 | N/A | N/A | 0.17 | −66.0% | 0.27 | −45.7% |
| 70 | 158 | 0.01 | −97.6% | 0.33 | −41.5% | 0.35 | −38.2% |
| 80 | 176 | 0.51 | −33.4% | 0.67 | −12.4% | 0.60 | −20.9% |
| 90 | 194 | 1.00 | 0.0% | 1.00 | 0.0% | 1.00 | 0.0% |
| 100 | 212 | 1.27 | −2.3% | 1.33 | 3.0% | 1.29 | 0.0% |
| 110 | 230 | 1.53 | −7.4 | 1.67 | 0.7% | 1.65 | 0.0% |
| 120 | 248 | 1.80 | −13.9% | 2.00 | −4.2% | 2.09 | 0.0% |
| 130 | 266 | 2.06 | −20.8% | 2.33 | −10.4% | 2.60 | 0.0% |
| Equivalent Age Errors (if True Q = 6500 K) | | | | | | | |
| Temperature | | Improved Nurse-Saul | | Improved Nurse-Saul (Second Alternative) (To = 60.0 C.) | | Arrhenius | |
| (° C.) | (° F.) | EAF | % Error | EAF | % Error | EAF | % Error |
| −10 | 14 | N/A | N/A | N/A | N/A | 0.00 | 0.0% |
| −5 | 23 | N/A | N/A | N/A | N/A | 0.00 | 0.0% |
| 0 | 32 | N/A | N/A | N/A | N/A | 0.00 | 0.0% |
| 5 | 41 | N/A | N/A | N/A | N/A | 0.00 | 0.0% |

TABLE 18-continued

Conservative Nature of Improved Nurse-Saul (and First Alternative) and Improved Arrhenius Maturity Methods at $T_{ref}= 90°$ C.

| | | | | | | | |
|---|---|---|---|---|---|---|---|
| 10 | 50 | N/A | N/A | N/A | N/A | 0.01 | 0.0% |
| 15 | 59 | N/A | N/A | N/A | N/A | 0.01 | 0.0% |
| 20 | 68 | N/A | N/A | N/A | N/A | 0.01 | 0.0% |
| 25 | 77 | N/A | N/A | N/A | N/A | 0.02 | 0.0% |
| 30 | 86 | N/A | N/A | N/A | N/A | 0.03 | 0.0% |
| 35 | 95 | N/A | N/A | N/A | N/A | 0.04 | 0.0% |
| 40 | 104 | N/A | N/A | N/A | N/A | 0.06 | 0.0% |
| 45 | 113 | N/A | N/A | N/A | N/A | 0.08 | 0.0% |
| 50 | 122 | N/A | N/A | N/A | N/A | 0.11 | 0.0% |
| 55 | 131 | N/A | N/A | N/A | N/A | 0.15 | 0.0% |
| 60 | 140 | N/A | N/A | 0.00 | N/A | 0.20 | 0.0% |
| 65 | 149 | N/A | N/A | 0.17 | −66.0% | 0.27 | 0.0% |
| 70 | 158 | 0.01 | −97.6% | 0.33 | −41.5% | 0.35 | 0.0% |
| 80 | 176 | 0.51 | −33.4% | 0.67 | −12.4% | 0.60 | 0.0% |
| 90 | 194 | 1.00 | 0.0% | 1.00 | 0.0% | 1.00 | 0.0% |
| 100 | 212 | 1.27 | −2.3% | 1.33 | 3.0% | 1.29 | −19.9% |
| 110 | 230 | 1.53 | −7.4 | 1.67 | 0.7% | 1.65 | −35.1% |
| 120 | 248 | 1.80 | −13.9% | 2.00 | −4.2% | 2.09 | −46.8% |
| 130 | 266 | 2.06 | −20.8% | 2.33 | −10.4% | 2.60 | −56.0% |

SPC Maturity

Conventional methods for concrete quality control rely upon various actions taken during concrete production and/or placement (e.g. casting test specimens; measuring slump, air content, temperature, unit weight; visual observation) followed by other actions taken several days or weeks later (e.g. breaking test specimens for strength determination). Strength acceptance for concrete typically relies upon the results of 28-day-old test specimens broken under controlled loading conditions.

The components in the concrete mix most responsible for the overall strength of the mix, the cementitious materials such as portland cement and fly ash, are rarely tested at the concrete plant. Instead, quality control personnel at the concrete plant typically rely upon certification testing performed at the point of production for the cementitious materials.

The chemical composition for a given source of cementitious material can change over time as the constituent raw materials and manufacturing conditions change. As such, concrete producers sometimes experience "unexplainable" changes in the strengths produced by a given concrete mix design, even when the material sources have remained "unchanged." The present invention overcomes the problems associated with unexpected or unknown changes to the raw materials of concrete by setting forth a method whereby statistical process control (SPC) charting is used to track the residual errors associated with an early-strength prediction model. Whenever the residual errors are "in control," the concrete producer can rest assured that the constituents going into the concrete mix have not changed appreciably. "In control" refers to the condition wherein all observed variation can be explained as variation inherent in the process rather than special-cause variation (i.e. variation caused by something "outside" the process, such as a change in raw material properties). A series of SPC rules are applied to establish whether or not the process is "in control." For example, if a single observation falls outside the outer control limits (typically plus-or-minus three standard deviations based on historical data), the process is considered "not in control."

Figure 20:
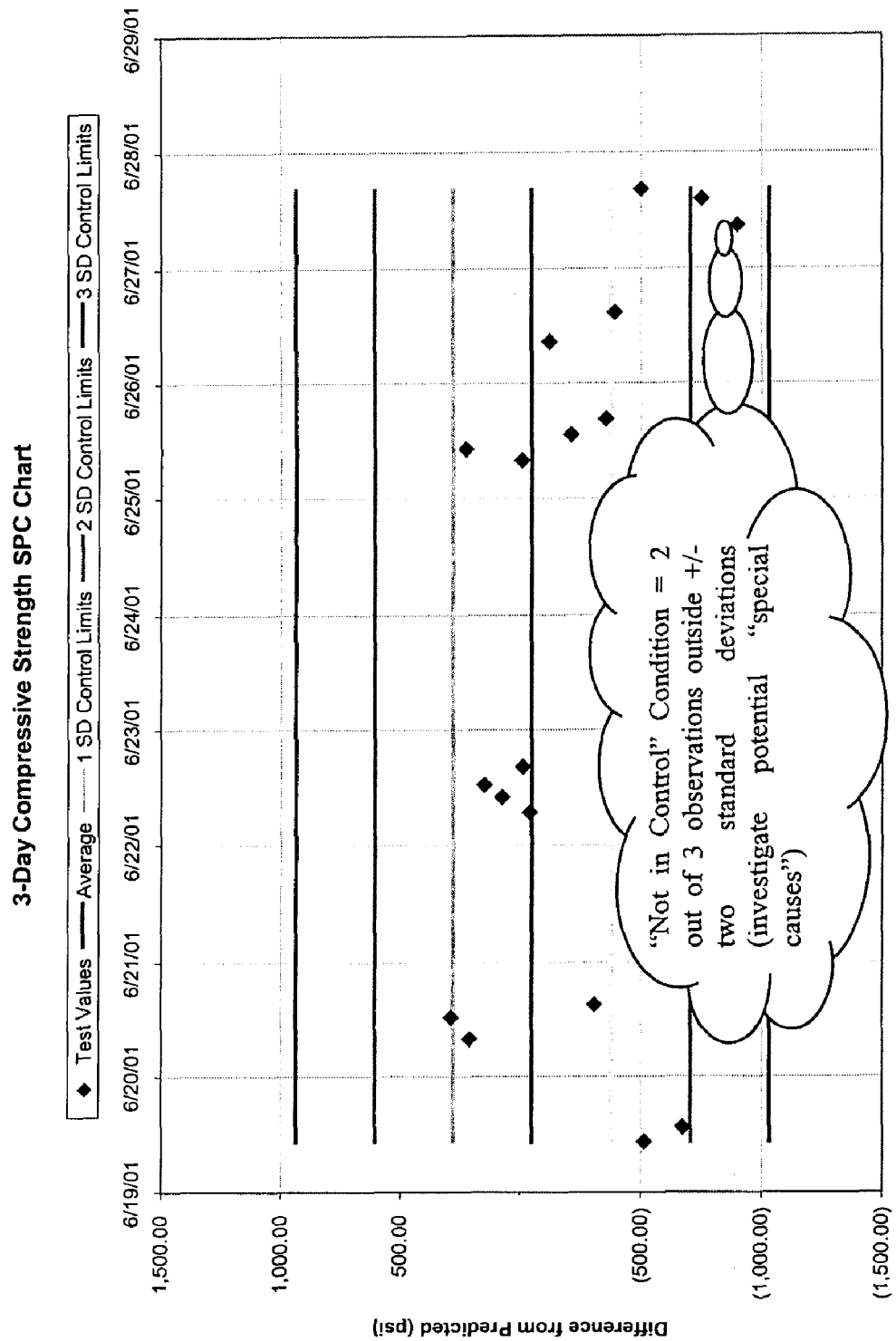
FIG. 20—Shows a sample Statistical Process Control (SPC) chart to quickly identify special-cause variations with the concrete mix proportioning and/or characteristics of the raw materials.

A typical application of this invention would involve breaking a set of test specimens that are 2- or 3-days-old, then subtracting the observed strength values from the predicted strength values. This difference, known as the "residual," would then be entered onto the SPC chart. FIG. 20 provides an example of an SPC chart wherein a "not in control" condition has occurred (two out of three observations are outside the plus-or-minus two-standard-deviation control limits).

It should be understood that various methods for establishing a strength-prediction equation are available. The present invention will work regardless of the precision and accuracy of the strength-prediction method utilized. However, greater precision in the strength-prediction equation will result in greater capability for the present invention to determine special-cause variation. A lack of precision in strength prediction may cause special-cause variations to be "masked" or go unnoticed, particularly if the effects of the special cause are relatively small compared to the precision of the prediction equation.)

The preferred embodiment of the present invention involves the use of maturity or Enhanced Maturity as the means for developing a strength-prediction equation. Maturity methods enable a prediction equation that effectively compensates for the temperature-time history of the specimen. Enhanced maturity takes this compensation a step further by compensating for changes to air content and water-to-cementitious-materials ratio, thus providing increased prediction precision when compared to conventional maturity methods. The preferred embodiment can be accomplished using maturity measured as a temperature-time factor (i.e. the Nurse-Saul or Improved Nurse-Saul method) or equivalent age (i.e. the Arrhenius or Improved Arrhenius method) or any other suitable means for measuring concrete maturity.

Loggers, Readers, and Software

The present invention also involves a system to automate and simplify the implementation of the aforementioned methods and protocols. The preferred embodiment of the system involves a sacrificial maturity and/or temperature logging device (i.e. logger) in conjunction with a handheld reader and software. One example of a system having a suitable logging device, handheld reader and software is described and shown in detail in our co-pending patent application Ser. No. 10/351,856, entitled "CONCRETE STRENGTH METERING SENSOR", filed on Jan. 24, 2003, the entire content of which is hereby expressly incorporated herein by reference. Particular attention is directed to pages 7-31 of the Specification and FIGS. 1-12 of U.S. Ser. No. 10/351,856.

The logger is provided with a microprocessor, memory means, temperature sensor and battery. The microprocessor and memory means contain firmware source code controlling the function and operation of the logger as well as communication with the handheld reader.

Two types of loggers are involved with the preferred embodiment. The first logger is used during the calibration process, while the second logger uses the calibration information to enable future strength measurements of concrete masses comprised of the same mix design as the concrete used for the calibration. The calibration logger calculates the reference temperature as the average curing temperature or the weighted-average curing temperature of the calibration specimens. This data can then be displayed on the handheld reader. The calibration logger also has the capability to receive and store the strength data corresponding to the companion specimens that are destructively tested for strength via a communication link with the handheld reader, in addition to other batch-specific information about the concrete, such as air content, water-to-cementitious-materials ratio, gross unit weight, etc.

After a maturity calibration procedure has been completed, the strength, maturity and temperature data can be uploaded to the handheld reader and further processed into final strength-maturity relationship data. The handheld reader can then download the processed data to a personal computer and/or store the strength-maturity relationship data, including the reference temperature and maturity calculation method, onto the field loggers.

The field loggers can then calculate maturity in real-time (according to the calculation method used during calibration). This is made possible by the fact that, for the Improved Arrhenius method, the reference temperature and the "first" and "second" apparent activation energy values are stored within the field logger (with those values being either pre-loaded or input by the user at time of placement into the concrete mass). Similarly, for the Improved Nurse-Saul method, the reference temperature and the "first" and "second" datum temperatures are stored within the field logger. For the First and Second Alternatives to the Improved Nurse-Saul method, only the "combined" datum temperature need be stored in the field logger.

For Enhanced Maturity applications, the Enhanced Maturity equations can be stored in the logger or, the appropriate batch-specific information can be input, with only the Enhanced Maturity equation or curve specific to that batch being stored in the logger.

Using the Loggers and Readers, the user can then, at any subsequent time, obtain current, precise measurements of the concrete's strength or degree of hydration using one or more of the following inventive concepts described herein, such as Enhanced Maturity, Improved Maturity, and/or Moisture-Loss Maturity. For example, if the Enhanced Maturity and the Moisture-Loss Maturity are installed on the logger and the reader, then the user can obtain either or both of strength measurements based on the Enhanced Maturity and degree of hydration measurements based on the Moisture-Loss Maturity.

The software automates and simplifies the calibration procedures by stepping the user through each step of the calibration (including the multiple batches required for Enhanced Maturity). The software also automates the SPC Maturity procedure by automatically applying the various SPC "alarm" conditions, then informing the user concerning the most likely causes of the "special-cause" variation thusly identified.

Changes may be made in the embodiments of the invention described herein, or in the parts or the elements of the embodiments described herein or in the step or sequence of steps of the methods described herein, without departing from the spirit and/or the scope of the invention as defined in the following claims.

REFERENCES

The following references, to the extent that they provide exemplary procedural or other details supplementary to those set forth herein, are specifically incorporated herein by reference in their entirety as though set forth herein in particular.

ASTM C 31-00. (2002). "Standard Practice for Making and Curing Concrete Test Specimens in the Field." 2002 *ASTM Standards Vol.* 04.02. West Conshohocken, Pa.: ASTM International.

ASTM C 138-01a. (2002). "Standard Test Method for Density (Unit Weight), Yield, and Air Content (Gravimetric) of Concrete." 2002 *ASTM Standards* Vol. 04.02. West Conshohocken, Pa.: ASTM International.

ASTM C 173-01. (2002). "Standard Test Method for Air Content of Freshly Mixed Concrete by the Volumetric Method." 2002 *ASTM Standards Vol.* 04.02. West Conshohocken, Pa.: ASTM International.

ASTM C 192-00. (2002). "Standard Practice for Making and Curing Concrete Test Specimens in the Laboratory." 2002 *ASTM Standards Vol.* 04.02. West Conshohocken, Pa.: ASTM International.

ASTM C 231-01. (2002). "Standard Test Method for Air Content of Freshly Mixed Concrete by the Pressure Method." 2002 *ASTM Standards Vol.* 04.02. West Conshohocken, Pa.: ASTM International.

ASTM C 666-97. (2002). "Standard Test Method for Resistance of Concrete to Rapid Freezing and Thawing." 2002 *ASTM Standards Vol.* 04.02. West Conshohocken, Pa.: ASTM International.

ASTM C 1074-98. (2002). "Standard Practice for Estimating Concrete Strength by the Maturity Method." 2002 *ASTM Standards Vol.* 04.02. West Conshohocken, Pa.: ASTM International.

ASTM C 1202-97. (2002). "Standard Test Method for Electrical Indication of Concrete's Ability to Resist Chloride Ion Penetration." 2002 *ASTM Standards Vol.* 04.02. West Conshohocken, Pa.: ASTM International.

Bentz, D. P. (1997). "Three-dimensional computer simulation of portland cement hydration and microstructure development." *Journal of the American Ceramic Society.* Westerville, Ohio: The American Ceramic Society, Vol. 80, No. 1, pp. 3-21.

Carino, N. J. and Lew, H. S. (2001). *The Maturity Method: From Theory to Application*. Gaithersburg, Md.: Building and Fire Research Laboratory, National Institute of Standards and Technology.

Crawford, G. I. (1997). *Guide to Nondestructive Testing of Concrete*. (FHWA-SA-97-105). Washington, D.C.: Federal Highway Administration.

Dowell, A. and Cramer, S. (2002). *Field Measurement of Water-Cement Ratio for Portland Cement Concrete—Phase II Field Evaluation and Development*. (WHRP 02-002). Madison, Wis.: Wisconsin Department of Transportation.

Federal Highway Administration (FHWA) (1988). *Early Strength Gain and Concrete Maturity*. Demonstration Project No. 75, Field Management of Concrete Mixes. Iowa Demonstration Project US-20, between Waterloo and Dubuque. Washington, D.C.: Federal Highway Administration.

Hossain, M. and Wojakowski, J. (1994). "Construction and performance of a fast-track concrete pavement in Kansas." *Transportation Research Board* 1465. Washington, D.C.: Transportation Research Board, National Research Council.

Constantino-Obon, C. A. (1998). *Investigation of the Maturity Concept as New Quality Control/Quality Assurance Measure for Concrete*. Austin, Tex.: University of Texas at Austin (Ph.D. Dissertation).

Okamoto, P. A. et al (1994). *Guidelines for Timing Contraction Joint Sawing and Earliest Loading for Concrete Pavements*. McLean, Va.: Turner-Fairbank Highway Research Center, Federal Highway Administration.

Tikalsky, P. J. et al (2001). *Using the Concrete Maturity Meter for QA/QC*. University Park, Pa.: The Pennsylvania State University.

What is claimed is:

1. A method for determining critical times for protecting a concrete mass from moisture loss, comprising the steps of:
    determining a desired degree of hydration of the concrete mass;
    placing at least one temperature sensor in thermal communication with the concrete mass to generate sensor data indicative of the temperature of the concrete mass;

establishing a mix-specific hydration-temperature relationship for the concrete mass indicative of the maturity of the concrete mass;

determining a threshold maturity value corresponding to the desired degree of hydration of the concrete mass;

monitoring the sensor data to determine when the threshold maturity value is reached; and providing protection from moisture loss of the concrete mass until at least the threshold maturity value is reached.

2. The method of claim 1, wherein the step of placing the temperature sensor is defined further as placing a maturity sensor within the concrete mass with the maturity sensor including the temperature sensor.

3. The method of claim 1, wherein the desired degree of hydration is determined via a correlation between a measured degree of hydration and a durability property of interest of multiple specimens.

4. The method of claim 3, wherein the durability property of interest is permeability of the multiple specimens.

5. The method of claim 3, wherein the durability property of interest is a durability factor of the multiple specimens.

* * * * *